US008802932B2

(12) United States Patent
Altier et al.

(10) Patent No.: US 8,802,932 B2
(45) Date of Patent: Aug. 12, 2014

(54) ANTIPATHOGENIC PROTEINS AND METHODS OF USE

(75) Inventors: Daniel J. Altier, Granger, IA (US); Jacob T. Gilliam, Norwalk, IA (US); Eric J. Schepers, Port Deposit, MD (US); Nasser Yalpani, Johnston, IA (US)

(73) Assignees: Pioneer Hi Bred International Inc, Johnston, IA (US); E I Du Pont De Nemours and Company, Wilmington, DE (US)

( * ) Notice: Subject to any disclaimer, the term of this patent is extended or adjusted under 35 U.S.C. 154(b) by 170 days.

(21) Appl. No.: 13/205,731

(22) Filed: Aug. 9, 2011

(65) Prior Publication Data

US 2012/0054910 A1 Mar. 1, 2012

Related U.S. Application Data

(60) Provisional application No. 61/373,042, filed on Aug. 12, 2010.

(51) Int. Cl.

| | |
|---|---|
| ***C12N 15/00*** | (2006.01) |
| ***A01N 63/00*** | (2006.01) |
| ***C12N 15/82*** | (2006.01) |
| ***C12N 15/87*** | (2006.01) |
| ***A01H 5/00*** | (2006.01) |
| ***A01H 5/10*** | (2006.01) |

(52) U.S. Cl.
USPC .......... 800/301; 424/93.2; 800/279; 800/288; 800/298; 435/320.1

(58) Field of Classification Search
None
See application file for complete search history.

(56) References Cited

U.S. PATENT DOCUMENTS 7,214,786 B2 5/2007 Kovalic et al.

OTHER PUBLICATIONS

Pozo et al. 2002. The antifungal protein of *Aspergillus giganteus* is an oligonucleotide/oligosaccharide binding (OB) fold-containing protein that produces condensation of DNA. J. Biological Chemistry. 277(48):46179-46183.*
GenBank Accession No. EGU89053 (2011).
GenBank Accession No. EFQ26236 (2010).

* cited by examiner

*Primary Examiner* — Anne Kubelik
*Assistant Examiner* — Jeffrey Bolland
(74) *Attorney, Agent, or Firm* — Pioneer Hi-Bred Int'l, Inc.

(57) ABSTRACT

Compositions and methods for protecting a plant from a pathogen, particularly a fungal pathogen, are provided. Compositions include amino acid sequences, and variants and fragments thereof, for family members of a novel family of antipathogenic polypeptides. Polynucleotides that encode the antipathogenic polypeptides are also provided. A method for inducing pathogen resistance in a plant using the polynucleotides disclosed herein is further provided. Compositions comprising an antipathogenic polypeptide or a microorganism comprising an antipathogenic polynucleotide of the invention in combination with a carrier and methods of using these compositions to protect a plant from a pathogen are further provided. Plants, plant cells, seeds, and microorganisms comprising an antipathogenic polnucleotide or polypeptide of the invention are also disclosed.

10 Claims, 4 Drawing Sheets

```
               SEQ
               ID
               NO:      1                                                          60
AclAFP1         17 (1) -----------------------MGAGDTGAPR--AGGSQSGDSFTRREAAQESLYIHEK
NfAFP1          75 (1) -----------------------MGEGDTGAPR--AGGVQSGDSFTRREAAQESMYIHEK
AtAFP1          29 (1) -----------------------MSEGDTGAPR--SGGSAQGDAFTRREAAQENLYIHEK
AnAFP1          21 (1) -----------------------MGAGDTGAPR--PGGSQHADSFTKREAAQENLYVREK
AoAFP1          25 (1) -----------------------MAAGDTGAPR--PGGSQHADQFTKREAAQENLYIHEK
ThaAFP1         93 (1) -----------------------MGAGDLGAPK--THGYQQDDQFHRREAAQESLYIREK
AcAFP1          13 (1) -----------------------MGEGDVGAPKS-TGKLSTTNSWSKKEAADEAMYIKQR
CiAFP1          49 (1) -----------------------MGEGDTGAVR--PGGVQSGDAWTKKESAQENMFIRQQ
PnAFP1          87 (1) -----------------------MAEGATGSGASRPTGSAGGDAFTKREAASEELYIRQE
PjAFP1          88 (1) ------------------------TAGATGATRQ-DGST---DAFEKREKAQEDLYIRQH
ScAFP1          89 (1) --MLPRSALARSLQLQRGVAARFYSEGSTGTPRG-SGSE---DSFVKRERATEDEFVRQR
YlAFP1         106 (1) --MLTRITTATVTRVPR-VAARFYSEGSTGSYRG-EGSG---DSFTKREKAQEDLYVKQQ
BcAFP1          37 (1) -----------------------MGEGDTGAARF-GGQQ---DAFTKREKANEDYTIRQR
BcAFP2          41 (1) -----------------------MGEGDTGAARF-GGQQ---DAFTKREKANEDYTIRQR
BfAFP1          33 (1) -----------------------MGEGDTGAARF-GGQQ---DAFTKREKANEDYTIRQR
GmAFP1          61 (1) -----------------------MGEGDTGAARF-GGQQ---DAFTKREKANEDFTIRQR
TaAFP1          97 (1) -----------------------MAAGDTGSPKV-GGSAS-ADAFTQREKSNEDEHIRSR
OnAFP1          83 (1) -----------------------MSEGATGAPPK-SGN---PDAFQRRERANEDYTIRQR
TrAFP1          95 (1) -----------------------MGEGDTGAPPK-TGGQ--GDAFQRREKAAEDYAIRQR
VvAFP1         105 (1) -----------------------MGAGDTGSPPK-TGGA--GDAFQKREKAAEDYAIRQR
FgAFP1          57 (1) -----------------------MTEGATGAPRP-TGGS--GDAFQRREKASEDYAIRQR
TaAFP2         101 (1) -----------------------MTEGATGAPRP-TGGS--GDAFQRREKASEDYAIRQR
FvAFP1           4 (1) -----------------------MTEGATGSVRP-TGGS--GDAFQRREKASEDYAIRQR
FvAFP1 Nt       5 (1) ------------------------TEGATGSVRP-TGGS--GDAFQRREKASXDYAI---
NhAFP1          71 (1) -----------------------MTEGATGAPPK-TGGP--GDAFQRREKANEDYAIRQR
MgAFP1          65 (1) -----------------------MAEGDLGSTPK-TGG---GDAFQKRERAQEDYAIRQR
CgAFP1          45 (1) -----------------------MAAGDTGAPPK-TGGA--GDAFQKRERASEDEAIRQR
CgrAFP1          9 (1) -----------------------MAEGDTGAPSK-YGG---GDAFQKREKANEDYAIRQR
DmAFP1          53 (1) -----------------------MAAGDTGAPPK-GLGQ--ADAFQKREKANEDFAIRLR
NcAFP1          77 (1) MLRTTVSKLARPTVSRAFATTSRALAGETGAPPK-TGGP--GDAFQRREKANEDFAIRQR
Consensus107(1)                               MGEGDTGAPR  TGG   GDAF KREKANEDY IRQR
```

FIG. 1A

```
               SEQ
               ID
               NO:      61                                        103
AclAFP1         17 (36) EKEKLESLRKKIKEQQAHLAELDKHLDDHTKNQG-KN------
NfAFP1          75 (36) EKEKLASLKRKIQEQQEHLNELDKHLKELSRNQGGENN-----
AtAFP1          29 (36) EMEKLEALRKKVNEQQKHLNELDQHLKDLQKEQGGEKN-----
AnAFP1          21 (36) EMEKLRALKAKLSEQRKHLDELDKHIDEFTKNQGGEQN-----
AoAFP1          25 (36) EREKLLALRNKVKEQRKHLDELDKHIEELTKNQGGEQN-----
ThaAFP1         93 (36) ELEKLRALKAKIQEQRKHLEELDKHIDELTREQGGEKN-----
AcAFP1          13 (37) EMEKLRTLREKLKQQRQHLDELDAHIEQLTREHGGEQN-----
CiAFP1          49 (36) EIEKLRALKEKLKQQRKHLDELDAHIDELTKQQGGEHH-----
PnAFP1          87 (38) EKAKLLAIKEKLRQQRQHIEDLDKHIDDVIKEGEASGQGEQK-
PjAFP1          88 (33) EKEQLEALKESLKKQKKSLDDLEBKIDDLTK------------
ScAFP1          89 (55) EKEQLRHLKEQLEKQRKKIDSLENKIDSMTK------------
YlAFP1         106 (54) EKEKLDALRKQLNKLKQDTADLEKHLDSKK-------------
BcAFP1          37 (34) ENEKLLELRKKITEQRDHLKKLEDHISEIEKQSGGEQK-----
BcAFP2          41 (34) ENEKLLELRKKITEQRDHLKKLEDHISEIEKQSGGEQN-----
BfAFP1          33 (34) ENEKLLELRKKITEQRDHLKKLEDHISEIEKQSGGEQN-----
GmAFP1          61 (34) ENEKLLELRKKIKEQREHLKKLEDHISEIERQSGGEQK-----
TaAFP1          97 (36) EREKLLELQKTYLKTHDHYVDXEEHLDELFNMDPGQGXGGKXS
OnAFP1          83 (34) EKEKLQQLKLKLKEQQAHLDQLAQHMFVANDQKN---------
TrAFP1          95 (35) EKEKLLELRKKLTRAAGAPRSPRQAIDEITKEQGGEQN-----
VvAFP1         105 (35) EKEKLLEMKKKIQGASRLT--CKQAL-----------------
FgAFP1          57 (35) EKEKLIELKKKLQEQQQHLDRLSKHIDEITKEQGGEQH-----
TaAFP2         101 (35) EKEKLIELKKKLQEQQQHLDRLSKHIDEITKEQGGEQH-----
FvAFP1           4 (35) EKEKLIELKKKLQEQQQHLDRLSKHIDEITREQGGEKN-----
FvAFP1 Nt       5 (31) -------------------------------------------
NhAFP1          71 (35) EKEKLIELKKKLQEQQQHLERLSKHIDEITKEQGGEQN-----
MgAFP1          65 (34) EKEKLLELKKKLAEQQAHLNKLSEHIDELTKSQGGEQN-----
CgAFP1          45 (35) EKQKLMELKKKLAEQQAHLQQLSDHIDEITQEQGGEQN-----
CgrAFP1          9 (34) EKEKLLELKKKLSEQQAHLQQLSDHIDEITKNQGGEHN-----
DmAFP1          53 (35) EKEKLLELKKKLAEQQAHLKQLSDHIDEITKEQGGEHN-----
NcAFP1          77 (58) EKEKLLELKKKLAEQQKHLKTLSDHIDEITREQGGERN-----
Consensus      107 (61) EKEKLLELKKKL EQ  HL  LD HIDEITK QGGEQN
```

FIG. 1B 0
1
2
3
4

ANTIPATHOGENIC PROTEINS AND METHODS OF USE

CROSS-REFERENCE TO RELATED APPLICATIONS

This application claims priority to U.S. Provisional Application No. 61/373,042, filed Aug. 12, 2010, which is hereby incorporated herein in its entirety by reference.

FIELD OF THE INVENTION

The present invention relates to polypeptides having antipathogenic activity and polynucleotides that encode the same. Methods of the invention utilize these antipathogenic polynucleotides and polypeptides to control plant pathogens and to increase pathogen resistance in plants.

BACKGROUND OF THE INVENTION

Plant diseases are often a serious limitation on agricultural productivity and therefore have influenced the history and development of agricultural practices. A variety of pathogens are responsible for plant diseases, including fungi, bacteria, and viruses. Among the causal agents of infectious diseases of crop plants, however, fungi are the most economically important group of plant pathogens and are responsible for huge annual losses of marketable food, fiber, and feed.

Incidence of plant diseases has traditionally been controlled by agronomic practices that include crop rotation, the use of agrochemicals, and conventional breeding techniques. The use of chemicals to control plant pathogens, however, increases costs to farmers and causes harmful effects on the ecosystem. Consumers and government regulators alike are becoming increasingly concerned with the environmental hazards associated with the production and use of synthetic agrochemicals for protecting plants from pathogens. Because of such concerns, regulators have banned or limited the use of some of the more hazardous chemicals. The incidence of fungal diseases has been controlled to some extent by breeding resistant crops. Traditional breeding methods, however, are time-consuming and require continuous effort to maintain disease resistance as pathogens evolve. See, for example, Grover and Gowthaman (2003) *Curr. Sci.* 84:330-340. Thus, there is a substantial interest in developing novel alternatives for the control of plant pathogens that possess a lower risk of pollution and environmental hazards than is characteristic of traditional agrochemical-based methods and that are less cumbersome than conventional breeding techniques.

Recently, agricultural scientists have developed crop plants with enhanced pathogen resistance by genetically engineering plants to express antipathogenic proteins. A continuing effort to identify antipathogenic agents and to genetically engineer disease-resistant plants is underway.

Thus, in light of the significant impact of plant pathogens, particularly fungal pathogens, on the yield and quality of crops, new compositions and methods for protecting plants from pathogens are needed.

BRIEF SUMMARY OF THE INVENTION

Compositions and methods for protecting a plant from a pathogen are provided. The compositions include novel nucleotide and amino acid sequences for antipathogenic, particularly antifungal, polypeptides. The presently disclosed polypeptides display antipathogenic activity against plant fungal pathogens. Polynucleotides comprising nucleotide sequences that encode the presently disclosed antipathogenic polypeptides are further provided. Compositions also include expression cassettes comprising a polynucleotide that encodes an antipathogenic polypeptide disclosed herein. Plants, plant cells, seeds, and microorganisms comprising the presently disclosed polynucleotides and polypeptides are further provided.

The compositions are useful in methods directed to inducing pathogen resistance, particularly fungal resistance, in plants. In particular embodiments, the methods comprise introducing into a plant at least one polynucleotide that encodes an antipathogenic polypeptide. As a result, the antipathogenic polypeptide is expressed in the plant, and the pathogen is exposed to the preferred protein at the site of pathogen attack, thereby leading to increased pathogen resistance. A tissue-preferred promoter may be used to drive expression of an antipathogenic protein in specific plant tissues that are particularly vulnerable to pathogen attack, such as, for example, the roots, leaves, stalks, vascular tissues, and seeds. Pathogen-inducible promoters may also be used to drive expression of an antipathogenic protein at or near the site of pathogen infection.

Further provided are antipathogenic compositions and formulations and methods for their use in protecting a plant from a pathogen, particularly a fungal pathogen. In some embodiments, compositions comprise an antipathogenic polypeptide or a microorganism comprising a polynucleotide encoding an antipathogenic polypeptide in combination with a carrier. Methods of using these compositions to protect a plant from a pathogen comprise applying the antipathogenic composition to the environment of a plant pathogen by, for example, spraying, dusting, broadcasting, or seed coating. The presently disclosed methods and compositions find use in protecting plants from pathogens, including fungal pathogens, viruses, bacteria, and the like.

The following embodiments are encompassed by the present invention:

1. An isolated polypeptide comprising an amino acid sequence selected from the group consisting of:
   (a) the amino acid sequence set forth in SEQ ID NO: 2, 4, 7, or 9; and
   (b) an amino acid sequence having at least 90% sequence identity to SEQ ID NO: 2, 4, 7, or 9, wherein said polypeptide has antipathogenic activity.

2. The isolated polypeptide of embodiment 1, wherein said polypeptide has antifungal activity.

3. An isolated polynucleotide comprising a nucleotide sequence selected from the group consisting of:
   (a) the nucleotide sequence set forth in SEQ ID NO: 6 or 8;
   (b) a nucleotide sequence encoding an amino acid sequence comprising SEQ ID NO: 7 or 9;
   (c) a nucleotide sequence having at least 90% sequence identity to SEQ ID NO: 6 or 8, wherein said polynucleotide encodes a polypeptide having antipathogenic activity;
   (d) a nucleotide sequence comprising at least 50 consecutive nucleotides of SEQ ID NO: 6 or 8, wherein said polynucleotide encodes a polypeptide having antipathogenic activity; and,
   (e) a nucleotide sequence encoding an amino acid sequence having at least 90% sequence identity to SEQ ID NO: 7 or 9, wherein said polynucleotide encodes a polypeptide having antipathogenic activity.

4. The isolated polynucleotide of embodiment 3, wherein said polynucleotide encodes a polypeptide having antifungal activity.

5. An expression cassette comprising the polynucleotide of embodiment 3.

6. The expression cassette of embodiment 5, wherein said polynucleotide is operably linked to a promoter that drives expression in a plant.

7. The expression cassette of embodiment 5, wherein said polynucleotide is operably linked to a promoter that drives expression in a microorganism.

8. A host cell comprising the polynucleotide of embodiment 3.

9. A host cell comprising the expression cassette of embodiment 5.

10. A plant comprising a heterologous polynucleotide operably linked to a promoter that drives expression in the plant, wherein said heterologous polynucleotide comprises a nucleotide sequence selected from the group consisting of:

(a) the nucleotide sequence set forth in SEQ ID NO: 1, 3, 6, or 8;

(b) a nucleotide sequence encoding the amino acid sequence comprising SEQ ID NO: 2, 4, 7, or 9;

(c) a nucleotide sequence having at least 90% sequence identity to SEQ ID NO: 1, 3, 6, or 8, wherein said polynucleotide encodes a polypeptide having antipathogenic activity;

(d) a nucleotide sequence comprising at least 50 consecutive nucleotides of SEQ ID NO: 1, 3, 6, or 8, wherein said polynucleotide encodes a polypeptide having antipathogenic activity; and, (e) a nucleotide sequence encoding an amino acid sequence having at least 90% sequence identity to SEQ ID NO: 2, 4, 7, or 9, wherein said polynucleotide encodes a polypeptide having antipathogenic activity.

11. The plant of embodiment 10, wherein said polynucleotide encodes a polypeptide having antifungal activity.

12. The plant of embodiment 10, wherein said nucleotide sequence is optimized for expression in a plant.

13. The plant of embodiment 10, wherein said plant is a plant part selected from the group consisting of a cell, a seed, and a grain.

14. The plant of embodiment 10, wherein said plant is a monocot.

15. The plant of embodiment 14, wherein said monocot is maize, sugarcane, wheat, rice, barley, sorghum, or rye.

16. The plant of embodiment 10, wherein said plant is a dicot.

17. The plant of embodiment 16, wherein the dicot is soybean, *Brassica*, sunflower, cotton, or alfalfa.

18. The plant of embodiment 10, wherein said polynucleotide is stably incorporated into the genome of the plant.

19. The plant of any one of embodiments 10-18, wherein said plant displays increased resistance to a plant pathogen.

20. The plant of embodiment 19, wherein said plant pathogen is a fungus.

21. The plant of embodiment 20, wherein said fungus is *Fusarium graminearum.*

22. The plant of embodiment 10, wherein said promoter is a tissue-preferred promoter.

23. The plant of embodiment 22, wherein said tissue-preferred promoter is selected from the group consisting of a leaf-preferred promoter, a root-preferred promoter, a seed-preferred promoter, a stalk-preferred promoter, and a vascular tissue-preferred promoter.

24. The plant of embodiment 10, wherein said promoter is a pathogen-inducible promoter.

25. A transformed seed of the plant of any one of embodiments 10-24.

26. A method of enhancing plant pathogen resistance in a plant, said method comprising providing to said plant a polypeptide selected from the group consisting of:

a) a polypeptide comprising the amino acid sequence set forth in SEQ ID NO: 2, 4, 7, or 9; and (b) a polypeptide comprising an amino acid sequence having at least 90% sequence identity to SEQ ID NO: 2, 4, 7, or 9, wherein said polypeptide has antipathogenic activity.

27. The method of embodiment 26, wherein said polypeptide has antifungal activity.

28. The method of embodiment 26, wherein said plant is a plant part selected from the group consisting of a cell, a seed, and a grain.

29. The method of embodiment 26, wherein said plant is a monocot.

30. The method of embodiment 29, wherein said monocot is maize, sugarcane, wheat, rice, barley, sorghum, or rye.

31. The method of embodiment 26, wherein said plant is a dicot.

32. The method of embodiment 31, wherein said dicot is soybean, *Brassica*, sunflower, cotton, or alfalfa.

33. The method of embodiment 26, wherein said plant pathogen is a fungus.

34. The method of embodiment 33, wherein said fungus is *Fusarium graminearum.*

35. The method of embodiment 26, wherein said plant is planted in an area of cultivation, wherein said area of cultivation comprises said plant pathogen, or wherein environmental conditions in said area of cultivation are conducive to the growth of said plant pathogen.

36. The method of embodiment 26, wherein providing the polypeptide comprises introducing into said plant a heterologous polynucleotide comprising a nucleotide sequence selected from the group consisting of:

(a) the nucleotide sequence set forth in SEQ ID NO: 1, 3, 6, or 8;

(b) a nucleotide sequence encoding the amino acid sequence comprising SEQ ID NO: 2, 4, 7, or 9;

(c) a nucleotide sequence having at least 90% sequence identity to SEQ ID NO: 1, 3, 6, or 8, wherein said polynucleotide encodes a polypeptide having antipathogenic activity; and (d) a nucleotide sequence encoding an amino acid sequence having at least 90% sequence identity to SEQ ID NO: 2, 4, 7, or 9, wherein said polynucleotide encodes a polypeptide having antipathogenic activity.

37. The method of embodiment 36, wherein said polynucleotide encodes a polypeptide having antifungal activity.

38. The method of embodiment 36, wherein said polynucleotide is stably integrated into the genome of the plant.

39. The method of embodiment 36, wherein said heterologous polynucleotide is operably linked to a promoter active in said plant.

40. The method of embodiment 39, wherein said promoter is a tissue-preferred promoter.

41. The method of embodiment 40, wherein said tissue-preferred promoter is selected from the group consisting of a leaf-preferred promoter, a root-preferred promoter, a seed-preferred promoter, a stalk-preferred promoter, and a vascular tissue-preferred promoter.

42. The method of embodiment 39, wherein said promoter is a pathogen-inducible promoter.

43. An antipathogenic composition comprising at least one polypeptide according to embodiment 1.

44. The composition of embodiment 43 further comprising a carrier.

45. A method for protecting a plant from a plant pathogen comprising applying the composition according to embodiment 43 to the environment of a plant pathogen.

46. The method of embodiment 45, wherein said composition is applied by a procedure selected from the group consisting of spraying, dusting, broadcasting, and seed coating.

47. The method of embodiment 45, wherein said plant pathogen is a fungus.

48. The method of embodiment 47, wherein said fungus is *Fusarium graminearum.*

49. A microorganism comprising at least one heterologous polynucleotide operably linked to a promoter that drives expression in the microorganism, wherein said polynucleotide comprises a nucleotide sequence selected from the group consisting of:

(a) the nucleotide sequence set forth in SEQ ID NO: 1, 3, 6, or 8;

(b) a nucleotide sequence encoding the amino acid sequence comprising SEQ ID NO: 2, 4, 7, or 9;

(c) a nucleotide sequence having at least 90% sequence identity to SEQ ID NO: 1, 3, 6, or 8, wherein said polynucleotide encodes a polypeptide having antipathogenic activity;

(d) a nucleotide sequence comprising at least 50 consecutive nucleotides of SEQ ID NO: 1, 3, 6, or 8, wherein said polynucleotide encodes a polypeptide having antipathogenic activity; and (e) a nucleotide sequence encoding an amino acid sequence having at least 90% sequence identity to SEQ ID NO: 2, 4, 7, or 9, wherein said polynucleotide encodes a polypeptide having antipathogenic activity.

50. The microorganism of embodiment 49, wherein said polynucleotide encodes a polypeptide having antifungal activity.

51. An antipathogenic composition comprising at least one microorganism according to embodiment 49.

52. The composition of embodiment 51 further comprising a carrier.

53. A method for protecting a plant from a pathogen comprising applying the composition according to embodiment 51 to the environment of a plant pathogen.

54. The method of embodiment 53, wherein said composition is applied by a procedure selected from the group consisting of spraying, dusting, broadcasting, and seed coating.

55. The method of embodiment 53, wherein said plant pathogen is a fungus.

56. The method of embodiment 55, wherein said fungus is *Fusarium graminearum.*

57. A method for controlling a pathogen in an area of cultivation, said method comprising:

a) evaluating environmental conditions in an area of cultivation for the presence of a pathogen or conditions conducive to the growth of a pathogen;

b) selecting an effective amount of an antipathogenic composition, wherein the antipathogenic composition is the composition according to embodiment 43 or embodiment 51; and c) applying said antipathogenic composition to a crop, crop part, seed, or an area of cultivation of said crop.

58. A method for controlling a pathogen in an area of cultivation, said method comprising:

a) evaluating environmental conditions in an area of cultivation for the presence of a pathogen or conditions conducive to the growth of a pathogen; and b) planting the area with crop seeds or plants comprising a heterologous polynucleotide operably linked to a promoter that drives expression in the plant, wherein said heterologous polynucleotide comprises a nucleotide sequence selected from the group consisting of:

(i) the nucleotide sequence set forth in SEQ ID NO: 1, 3, 6, or 8;

(ii) a nucleotide sequence encoding the amino acid sequence comprising SEQ ID NO: 2, 4, 7, or 9;

(iii) a nucleotide sequence having at least 90% sequence identity to SEQ ID NO: 1, 3, 6, or 8, wherein said polynucleotide encodes a polypeptide having antipathogenic activity;

(iv) a nucleotide sequence comprising at least 50 consecutive nucleotides of SEQ ID NO: 1, 3, 6, or 8, wherein said polynucleotide encodes a polypeptide having antipathogenic activity; and, (v) a nucleotide sequence encoding an amino acid sequence having at least 90% sequence identity to SEQ ID NO: 2, 4, 7, or 9, wherein said polynucleotide encodes a polypeptide having antipathogenic activity.

59. The method of embodiment 57 or embodiment 58, wherein said pathogen is a fungus.

60. The method of embodiment 59, wherein said fungus is *Fusarium graminearum.*

These and other aspects of the invention are disclosed in more detail in the description of the invention given below.

BRIEF DESCRIPTION OF THE FIGURES

FIG. 1 shows a sequence alignment of the amino acid sequences of the mature *Fusarium verticillioides* antifungal protein 1 (FvAFP1; SEQ ID NO: 4) and *Colletotrichum graminicola* AFP1 (CgrAFP1; SEQ ID NO: 9) antifungal polypeptides and the sequence of the FvAFP1 protein as determined by amino-terminal sequencing (FvAFP1 Nt; SEQ ID NO: 5) with the following homologues: *Aspergillus clavatus* AFP1 (Ac1AFP1; SEQ ID NO: 17), *Neosartorya fischeri* AFP1 (NfAFP1; SEQ ID NO: 75), *Aspergillus terreus* AFP1 (AtAFP1; SEQ ID NO: 29), *Aspergillus niger* AFP1 (AnAFP1; SEQ ID NO: 21), *Aspergillus oryzae* AFP1 (AoAFP1; SEQ ID NO: 25), *Thermoascus aurantiacus* AFP1 (ThaAFP1; SEQ ID NO: 94), *Ajellomyces capsulatus* AFP1 (AcAFP1; SEQ ID NO: 13), *Coccidioides immitis* AFP1 (CiAFP1; SEQ ID NO: 49), *Phaeosphaeria nodorum* AFP1 (PnAFP1; SEQ ID NO: 87), *Pichia jadinii* AFP1 (PjAFP1; SEQ ID NO: 88), *Saccharomyces cerevisiae* AFP1 (ScAFP1; SEQ ID NO: 90), *Yarrowia lipolytica* AFP1 (Y1AFP1; SEQ ID NO: 110), *Botrytis cinerea* AFP1 (BcAFP1; SEQ ID NO: 37), *Botrytis cinerea* AFP2 (BcAFP2; SEQ ID NO: 41), *Botryotinia fuckeliana* AFP1 (BfAFP1; SEQ ID NO: 33), *Glycine max* AFP1 (GmAFP1; SEQ ID NO: 61), *Triticum aestivum* AFP1 (TaAFP1; SEQ ID NO: 100), *Ophiostoma novo-ulmi* AFP1 (OnAFP1; SEQ ID NO: 83), *Trichoderma reseii* AFP1 (TrAFP1; SEQ ID NO: 96), *Vitis vinifera* AFP1 (VvAFP1; SEQ ID NO: 108), *Fusarium graminearum* AFP1 (FgAFP1; SEQ ID NO: 57), *Triticum aestivum* AFP2 (TaAFP2; SEQ ID NO: 104), *Nectria haematococca* AFP1 (NhAFP1; SEQ ID NO: 71), *Magnaporthe grisea* AFP1 (MgAFP1; SEQ ID NO: 65), *Chaetomium globosum* AFP1 (CgAFP1; SEQ ID NO: 45), *Diplodia maydis* AFP1 (DmAFP1; SEQ ID NO: 53), and *Neurospora crassa* AFP1 (NcAFP1; SEQ ID NO: 77). With a few exceptions (PjAFP1 and FvAFP1 Nt), each of the sequences of the mature polypeptides in the alignment include the starting methionine. A consensus sequence (SEQ ID NO: 111) derived from all the polypeptides appearing in the alignment is further provided.

DETAILED DESCRIPTION OF THE INVENTION

A novel family of antipathogenic polypeptides is provided. This protein family is particularly interesting as these polypeptides lack disulfide bonds and can therefore be targeted for extracellular accumulation or accumulation in various intracellular compartments such as the cytoplasm. Most previously identified antipathogenic polypeptides are rich in disulfides and hence, allow for only limited deployment.

Polypeptides were identified from the fungi *Fusarium verticillioides* and *Colletotrichum graminicola*. These polypeptides, set forth herein as SEQ ID NOs: 2 and 4, and 7 and 9, respectively, exhibit antifungal activity against fungal plant pathogens, such as, for example, *Fusarium graminearum.*

Figure 2:
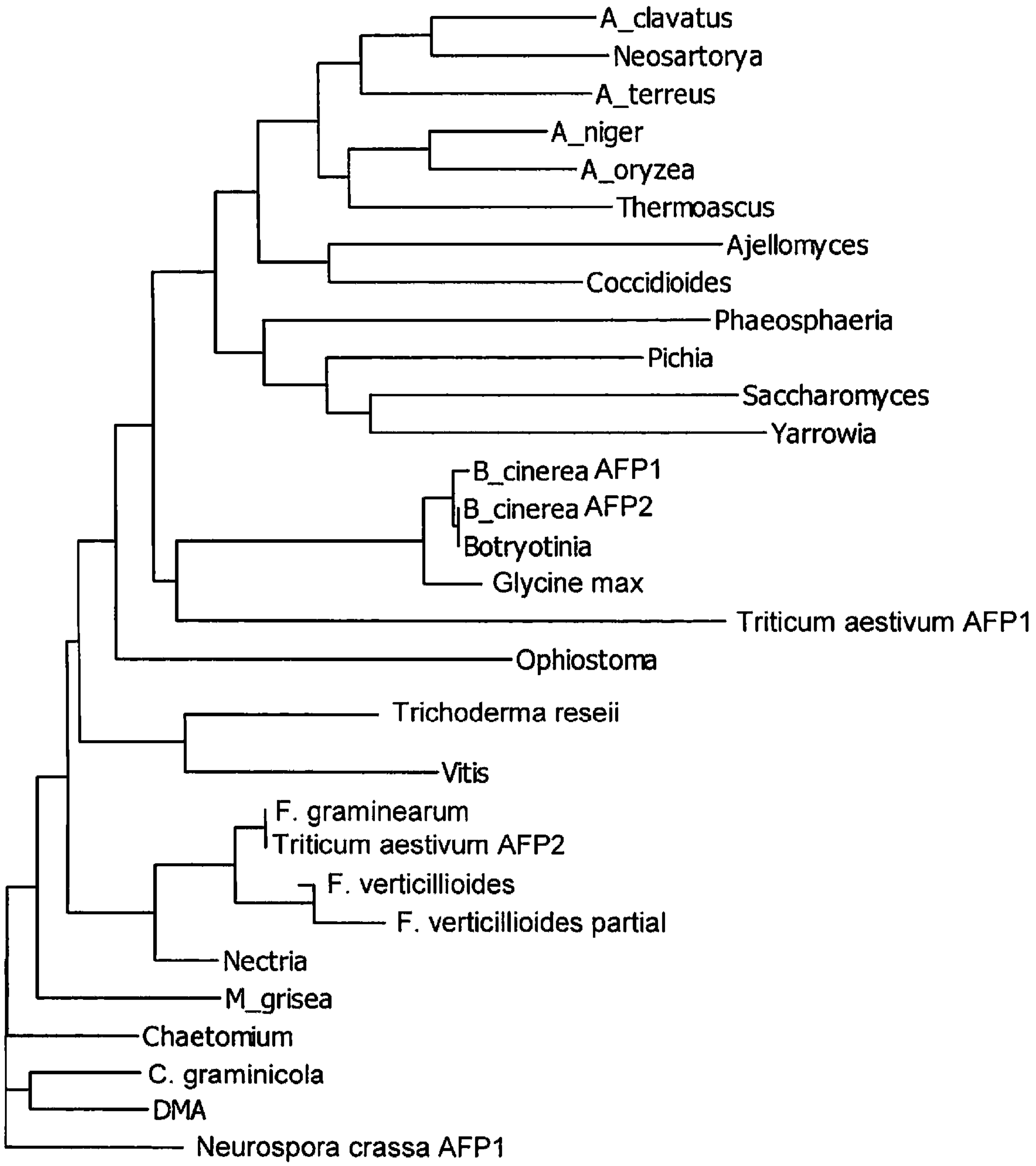
FIG. 2 shows a cladogram that depicts the phylogenetic relationships between the family members of the presently disclosed family of antipathogenic proteins.
Figure 3:
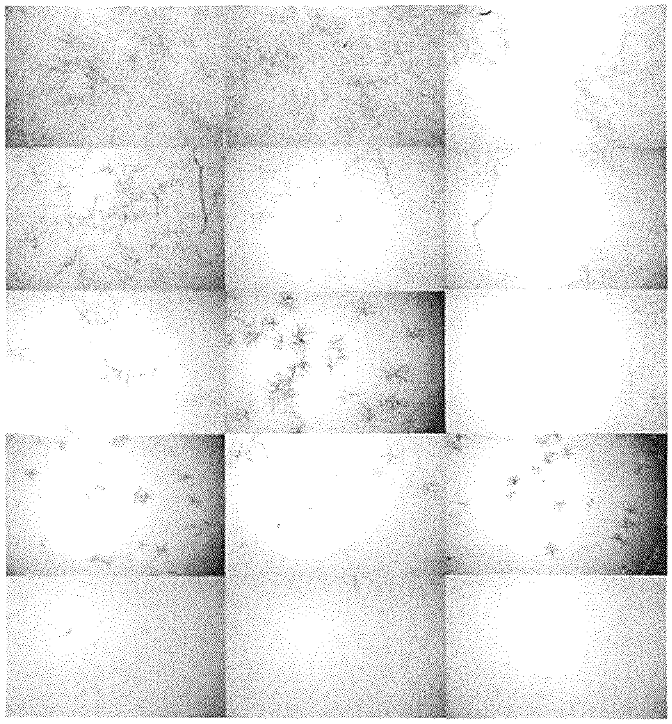
FIG. 3 shows photographic examples of the level of inhibition associated with each numerical score in the antifungal plate assay described in Example 2.

Additional polypeptides are provided that share homology with the amino acid sequences set forth in SEQ ID NOs: 2, 4, 7 and 9. In particular, the full-length (i.e. proprotein) and mature peptides (lacking an amino-terminal peptide present in the proprotein sequences) disclosed in Table 1 were identified using computer homology searches. An alignment of the mature polypeptide sequences that make up this novel family of antipathogenic proteins can be found in FIG. 1, along with a consensus sequence derived from all of the antipathogenic family members (SEQ ID NO: 111). FIG. 2 provides a phylogenetic analysis of the presently disclosed family of antipathogenic proteins.

TABLE 1

Predicted coding sequences (cds) and amino acid (aa) sequences for proprotein and mature polypeptides having homology to *Fusarium verticillioides* AFP1 (FvAFP1) and *Colletorichum graminicola* AFP1 (CgrAFP1).

| | | SEQ ID NO | | | |
|---|---|---|---|---|---|
| Name | Derivation of sequences | Proprotein cds | Proprotein aa sequence | Mature cds | Mature aa sequence |
| *Ajellomyces capsulatus* AFP1 (AcAFP1) | Acc. No. XM_001540636; predicted protein (Acc. No. XP_001540686.1) | 10 | 11 | 12 | 13 |
| *Aspergillus clavatus* AFP1 (AclAFP1) | Acc. No. XM_001272849; putative mitochondrial ATPase inhibitor (Acc. No. EAW11424) | 14 | 15 | 16 | 17 |
| *Aspergillus niger* AFP1 (AnAFP1) | Acc. No. XM_001391816; hypothetical protein (Acc. No. XP_001391853) | 18 | 19 | 20 | 21 |
| *Aspergillus oryzae* AFP1 (AoAFP1) | derived from genomic contig cDNA sequence (Acc. No. AB226129.1) | 22 | 23 | 24 | 25 |
| *Aspergillus terreus* AFP1 (AtAFP1) | Acc. No. XM_001218182.1; conserved hypothetical protein (Acc. No. XP_001218183) | 26 | 27 | 28 | 29 |
| *Botryotinia fuckeliana* AFP1 (BfAFP1) | Acc. No. XM_001548505; predicted protein (Acc. No. XP_001548555.1) | 30 | 31 | 32 | 33 |
| *Botrytis cinerea* AFP1 (BcAFP1) | derived from T4 cDNA library (Acc. No. AL116045.1) | 34 | 35 | 36 | 37 |
| *Botrytis cinerea* AFP2 (BcAFP2) | derived from T4 cDNA library clone (Acc. No. AL116267.1) | 38 | 39 | 40 | 41 |
| *Chaetomium globosum* AFP1 (CgAFP1) | Acc. No. XM_001548505; predicted protein (Acc. No. XP_001548555.1) | 42 | 43 | 44 | 45 |

TABLE 1-continued

Predicted coding sequences (cds) and amino acid (aa) sequences for proprotein and mature polypeptides having homology to *Fusarium verticillioides* AFP1 (FvAFP1) and *Colletorichum graminicola* AFP1 (CgrAFP1).

| Name | Derivation of sequences | SEQ ID NO Proprotein cds | Proprotein aa sequence | Mature cds | Mature aa sequence |
|---|---|---|---|---|---|
| *Coccidioides immitis* AFP1 (CiAFP1) | Acc. No. XM_001245094.1; predicted protein (Acc. No. XP_001245095.1) | 46 | 47 | 48 | 49 |
| *Diplodia maydis* AFP1 (DmAFP1) | Novel | 50 | 51 | 52 | 53 |
| *Fusarium graminearum* AFP1 (FgAFP1) | Acc. No. XM_387022; hypothetical protein (Acc. No. XP_387022.1) | 54 | 55 | 56 | 57 |
| *Glycine max* AFP1 (GmAFP1) | Novel | 58 | 59 | 60 | 61 |
| *Magnaporthe grisea* AFP1 (MgAFP1) | Acc. No. XM_363663; hypothetical protein (Acc. No. XP_363663.2) | 62 | 63 | 64 | 65 |
| *Magnaporthe grisea* AFP2 (MgAFP2) | Novel | 66 | 67 | 68 | 69 |
| *Nectria haematococca* AFP1 (NhAFP1) | Novel | 70 | 71 | ND | ND |
| *Neosartorya fischeri* AFP1 (NfAFP1) | Acc. No. XM_001265893.1; putative mitochondrial ATPase inhibitor (Acc. No. XP_001265894) | 72 | 73 | 74 | 75 |
| *Neurospora crassa* AFP1 (NcAFP1) | Acc. No. AABX02000007.1; hypothetical protein NCU02807 (Acc. No. EAA35227.2) | 76 | 77 | ND | ND |
| *Neurospora crassa* AFP2 (NcAFP2) | Novel | 78 | 79 | 80 | 81 |
| *Ophiostoma novo-ulmi* AFP1 (OnAFP1) | alternative translational reading frame of H+ transporting ATP synthase inhibitor-like protein mRNA (Acc. No. AF378547.1) | ND | ND | 82 | 83 |
| *Phaeosphaeria nodorum* AFP1 (PnAFP1) | Acc. No. CH445343.1; predicted protein (Acc. No. EAT81343.1) | 84 | 85 | 86 | 87 |
| *Pichia jadinii* AFP1 (PjAFP1) | Novel | ND | 88 | ND | ND |
| *Saccharomyces cerevisiae* AFP1 (ScAFP1) | Novel | 89 | 90 | ND | ND |
| *Thermoascus aurantiacus* AFP1 (ThaAFP1) | Novel | 91 | 92 | 93 | 94 |

TABLE 1-continued

Predicted coding sequences (cds) and amino acid (aa) sequences for proprotein and mature polypeptides having homology to *Fusarium verticillioides* AFP1 (FvAFP1) and *Colletorichum graminicola* AFP1 (CgrAFP1).

| | | SEQ ID NO | | | |
|---|---|---|---|---|---|
| Name | Derivation of sequences | Proprotein cds | Proprotein aa sequence | Mature cds | Mature aa sequence |
| *Trichoderma reseii* AFP1 (TrAFP1) | cds and aa derived from SEQ ID NO: 7640 from U.S. Pat. No. 7,186,513 (Acc. No. EA085380.1) and SEQ ID NO: 7640 from U.S. Pat. No. 6,902,887 (Acc. No. AR678139.1) | 95 | 96 | ND | ND |
| *Triticum aestivum* AFP1 (TaAFP1) | Novel | 97 | 98 | 99 | 100 |
| *Triticum aestivum* AFP2 (TaAFP2) | cds and aa derived from SEQ ID NO: 35473 from U.S. Pat. No. 7,214,786 (Acc. No. EA171158.1) | 101 | 102 | 103 | 104 |
| *Vitis vinifera* AFP1 (VvAFP1) | Novel | 105 | 106 | 107 | 108 |
| *Yarrowia lipolytica* AFP1 (YlAFP1) | chromosome C of strain CLIB122 of *Yarrowia lipolytica* (Swiss-Prot Acc. No. Q6CCY1) | 109 | 110 | ND | ND |

ND: Not Determined

Compositions include isolated polypeptides having the sequence set forth in SEQ ID NO: 2, 4, 7, or 9, and variants and fragments thereof. Further provided are compositions comprising polypeptides having the sequence set forth in SEQ ID NO: 51, 53, 59, 61, 67, 69, 71, 79, 81, 83, 88, 90, 92, 94, 96, 98, 100, 106, or 108, as well as variants and fragments thereof. In some embodiments, the antipathogenic protein has the consensus sequence set forth in SEQ ID NO: 111.

Isolated polynucleotides, and variants and fragments thereof, comprising nucleotide sequences that encode the amino acid sequences of SEQ ID NO: 2, 4, 7, 9, 51, 53, 59, 61, 67, 69, 71, 79, 81, 83, 88, 90, 92, 94, 98, 100, 106, 108, or 111 and variants and fragments thereof are also provided. Isolated polynucleotides having the sequence set forth in SEQ ID NO: 1, 3, 6, 8, 50, 52, 58, 60, 66, 68, 70, 78, 80, 91, 93, 95, 97, 99, 105, 107, or 109 as well as variants and fragments thereof are further provided. In those instances wherein complete nucleotide sequences are not available, methods are available in the art for obtaining the complete sequence.

Many of the polypeptides of Table 1 are putative proteins or proteins of unknown function. The *Pichia jadinii, Neosartorya fischeri, Ophiostoma novo-ulmi*, and *Aspergillus clavatus* sequences have been described as homologs to ATPase inhibitors (although the *Opiostoma novo-ulmi* sequence is derived from an alternate translational reading frame). Therefore, in some embodiments, the presently disclosed antipathogenic proteins function as ATPase inhibitors.

None of the polypeptides disclosed in Table 1 or the polypeptides having SEQ ID NO: 2, 4, 7, and 9 have been reported in the literature to possess antipathogenic activity. Thus, the amino acid sequences set forth in SEQ ID NOs: 2, 4, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 88, 90, 92, 94, 96, 98, 100, 102, 104, 106, 108, 110, and 111 and the nucleotide sequences set forth in SEQ ID NOs: 1, 3, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 91, 93, 95, 97, 99, 101, 103, 105, 107, and 109 can be used in the antipathogenic compositions and methods of the invention.

The polynucleotides and polypeptides of the present invention find use in methods for inducing pathogen resistance in a plant. Accordingly, the compositions and methods disclosed herein are useful in protecting plants against plant pathogens. By "plant pathogen" is intended any organism that can cause harm to a plant by inhibiting or slowing the growth of a plant, by damaging the tissues of a plant, by weakening the immune system of a plant, reducing the resistance of a plant to abiotic stresses, and/or by causing the premature death of the plant, etc. Plant pathogens include fungi, viruses, bacteria, and the like.

"Pathogen resistance" or "disease resistance" is intended to mean that the plant avoids the disease symptoms that are the outcome of plant-pathogen interactions. That is, pathogens are prevented from causing plant diseases and the associated disease symptoms, or alternatively, the disease symptoms caused by the pathogen are minimized or lessened, such as, for example, the reduction of stress and associated yield loss.

"Antipathogenic compositions" or "antipathogenic polypeptides" is intended to mean that the compositions of the invention have antipathogenic activity and thus are capable of suppressing, controlling, and/or killing the invading pathogenic organism. An antipathogenic polypeptide or composition of the invention will reduce the disease symptoms resulting from pathogen challenge by at least about 2%, including but not limited to, about 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater. In particular embodiments, the disease symptoms resulting from pathogen challenge are reduced by an antipathogenic polypeptide or composition of the invention by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens. In particular embodiments, the antipathogenic activity exhibited by the polypeptides of the invention is antifungal activity. As used herein, "antifungal activity" refers to the ability to suppress, control, and/or kill the invading fungal pathogen. Likewise, "fungal resistance" refers to enhanced tolerance to a fungal pathogen when compared to that of an untreated or wild type plant. Resistance may vary from a slight increase in tolerance to the effects of the fungal pathogen (e.g., partial inhibition) to total resistance such that the plant is unaffected by the presence of the fungal pathogen. An increased level of resistance against a particular fungal pathogen or against a wider spectrum of fungal pathogens may both constitute antifungal activity or improved fungal resistance.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antipathogenic polypeptide or having an antipathogenic composition applied to its surface or environment shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107-15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888-1892, herein incorporated by reference). Additionally, microspectrophotometrical analysis can be used to measure the in vitro antipathogenic properties of a composition (Hu et al. (1997) *Plant Mol. Biol.* 34:949-959 and Cammue et al. (1992) *J. Biol. Chem.* 267: 2228-2233, both of which are herein incorporated by reference). Assays that specifically measure antifungal activity are also well known in the art. See, for example, Duvick et al. (1992) *J. Biol. Chem.* 267: 18814-18820; Lacadena et al. (1995) *Arch. Biochem. Biophys.* 324:273-281; Xu et al. (1997) *Plant Mol. Biol.* 34: 949-959; Lee et al. (1999) *Biochem. Biophys. Res. Comm.* 263:646-651; Vila et al. (2001) *Mol. Plant Microbe Interact.* 14:1327-1331; Moreno et al. (2003) *Phytpathol.* 93:1344-1353; Kaiserer et al. (2003) *Arch. Microbiol.* 180:204-210; and U.S. Pat. No. 6,015,941; each of which are herein incorporated by reference.

The compositions disclosed herein comprise isolated polynucleotides that encode antipathogenic polypeptides, expression cassettes comprising the presently disclosed antipathogenic polynucleotides, and isolated antipathogenic polypeptides. Antipathogenic compositions comprising a presently disclosed polypeptide in combination with a carrier are also provided. The invention further discloses plants and microorganisms comprising polynucleotides that encode antipathogenic proteins.

As used herein, "polynucleotide" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The presently disclosed polynucleotides also encompass all forms of sequences including, but not limited to, single-stranded forms, double-stranded forms, hairpins, stem-and-loop structures, and the like.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. Polypeptides of the invention can be produced either from a polynucleotide disclosed herein, or by the use of standard molecular biology or biochemical techniques. For example, a truncated protein of the invention can be produced by expression of a recombinant polynucleotide of the invention in an appropriate host cell, or alternatively by a combination of ex vivo procedures, such as protease digestion and purification.

As used herein, the terms "encoding" or "encoded" when used in the context of a specified polynucleotide mean that the polynucleotide comprises the requisite information to direct translation of the nucleotide sequence into a specified protein. The information by which a protein is encoded is specified by the use of codons. A polynucleotide encoding a protein may comprise non-translated sequences (e.g., introns) within translated regions of the polynucleotide or may lack such intervening non-translated sequences (e.g., as in cDNA).

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an “isolated” polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the presently disclosed antipathogenic protein or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed polynucleotides and proteins encoded thereby are also encompassed by the present invention. By “fragment” is intended a portion of the polynucleotide or a portion of the amino acid sequence and hence protein encoded thereby. Fragments of a polynucleotide may encode protein fragments that retain the biological activity of the native protein and hence have antipathogenic activity. Alternatively, fragments of a polynucleotide that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length polynucleotide encoding the presently disclosed proteins.

A fragment of a polynucleotide that encodes a biologically active portion of a presently disclosed antipathogenic protein will encode at least 15, 25, 30, or 50 contiguous amino acids, or up to the total number of amino acids present in a full-length antipathogenic protein of the invention (for example, 96 amino acids for SEQ ID NO:2, 71 amino acids for SEQ ID NO:4, 99 amino acids for SEQ ID NO:7, and 70 amino acids for SEQ ID NO: 9, respectively). Fragments of a polynucleotide that are useful as hybridization probes or PCR primers generally need not encode a biologically active portion of an antipathogenic protein.

Thus, a fragment of a presently disclosed polynucleotide may encode a biologically active portion of an antipathogenic polypeptide, or it may be a fragment that can be used as a hybridization probe or PCR primer using methods disclosed below. A biologically active portion of an antipathogenic polypeptide can be prepared by isolating a portion of one of the polynucleotides of the invention, expressing the encoded portion of the antipathogenic protein (e.g., by recombinant expression in vitro), and assessing the activity of the encoded portion of the antipathogenic protein. Polynucleotides that are fragments of a nucleotide sequence of the invention comprise at least 16, 20, 50, 75, 100, 150, 200, or 250 contiguous nucleotides, or up to the number of nucleotides present in a full-length polynucleotide disclosed herein (for example, 291 nucleotides for SEQ ID NO: 1, 216 nucleotides for SEQ ID NO: 3, 299 nucleotides for SEQ ID NO: 6, and 212 nucleotides for SEQ ID NO: 8, respectively).

“Variants” is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a “native” polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the antipathogenic polypeptides of the invention. Naturally occurring allelic variants such as these can be identified with the use of well-known molecular biology techniques, as, for example, with polymerase chain reaction (PCR) and hybridization techniques as outlined elsewhere herein. Variant polynucleotides also include synthetically derived polynucleotides, such as those generated, for example, by using site-directed mutagenesis but which still encode an antipathogenic protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO: 2, 4, 7, 9, 51, 53, 59, 61, 67, 69, 71, 79, 81, 83, 88, 90, 92, 94, 98, 100, 106, 108, or 111 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

“Variant” protein is intended to mean a protein derived from the native protein by deletion or addition of one or more amino acids at one or more internal sites in the native protein and/or substitution of one or more amino acids at one or more sites in the native protein. Variant proteins encompassed by the present invention are biologically active, that is they continue to possess the desired biological activity of the native protein, that is, antipathogenic activity as described herein. Such variants may result from, for example, genetic polymorphism or from human manipulation. Biologically active variants of a native antipathogenic protein of the invention will have at least about 40%, 45%, 50%, 55%, 60%, 65%, 70%, 75%, 80%, 85%, 90%, 91%, 92%, 93%, 94%, 95%, 96%, 97%, 98%, 99%, or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants and fragments of the antipathogenic proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:

367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant forms Likewise, the proteins of the invention encompass both naturally occurring proteins as well as variations and modified forms thereof. Such variants will continue to possess the desired antipathogenic activity. Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assays that measure antipathogenic activity such as antifungal plate assays. See, for example, Duvick et al. (1992) *J. Biol. Chem.* 267:18841-18820, herein incorporated by reference.

Variant polynucleotides and proteins also encompass sequences and proteins derived from a mutagenic and recombinogenic procedure such as DNA shuffling. With such a procedure, one or more different antipathogenic protein coding sequences can be manipulated to create a new antipathogenic protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the *F. verticillioides* AFP1 gene and other known antipathogenic genes, such as, for example, other AFP family members, to obtain a new gene coding for a protein with an improved property of interest, such as increased antipathogenic activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the invention can be used to isolate corresponding sequences from other organisms, particularly other plants, more particularly other fungi. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that encode for an antipathogenic protein and which hybridize under stringent conditions to the sequences disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the polynucleotides of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire polynucleotide disclosed herein, or one or more portions thereof, may be used as a probe capable of specifically hybridizing to corresponding polynucleotides and messenger RNAs. To achieve specific hybridization under a variety of conditions, such probes include sequences that are unique among antipathogenic polynucleotide sequences and are optimally at least about 10 nucleotides in length, and most optimally at least about 20 nucleotides in length. Such probes may be used to amplify corresponding polynucleotides from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology-Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: (a) “reference sequence”, (b) “comparison window”, (c) “sequence identity”, and, (d) “percentage of sequence identity.”

(a) As used herein, “reference sequence” is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, “comparison window” makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) Gene 73:237-244 (1988); Higgins et al. (1989) CABIOS 5:151-153; Corpet et al. (1988) Nucleic Acids Res. 16:10881-90; Huang et al. (1992) CABIOS 8:155-65; and Pearson et al. (1994) Meth. Mol. Biol. 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) J. Mol. Biol. 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See ncbi.nlm.nih, which can be accessed on the World Wide Web using the "www" prefix. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

In particular aspects, methods for inducing pathogen resistance in a plant comprise introducing into a plant at least one polynucleotide, wherein the polynucleotide comprises a nucleotide sequence encoding an antipathogenic polypeptide of the invention. The polynucleotide is operably linked to a promoter that drives expression in the plant. The plant expresses the antipathogenic polypeptide, thereby exposing the pathogen to the polypeptide at the site of pathogen attack. In particular embodiments, the polypeptides have antifungal activity, and the pathogen is a fungus, such as, for example, *Fusarium graminearum*. Expression of an antipathogenic polypeptide of the invention may be targeted to specific plant tissues where pathogen resistance is particularly important, such as, for example, the leaves, roots, stalks, or vascular tissues. Such tissue-preferred expression may be accomplished by root-preferred, leaf-preferred, vascular tissue-preferred, stalk-preferred, or seed-preferred promoters. Moreover, the polypeptides of the invention may also be targeted to specific subcellular locations within a plant cell or, alternatively, secreted from the cell, as described herein below.

Just as expression of an antipathogenic polypeptide of the invention may be targeted to specific plant tissues or cell types through the use of appropriate promoters, it may also be targeted to different locations within the cell through the use of targeting information or "targeting labels." Unlike the promoter, which acts at the transcriptional level, such targeting information is part of the initial translation product. Depending on the mode of infection of the pathogen or the metabolic function of the tissue or cell type, the location of the protein in different compartments of the cell may make it more efficacious against a given pathogen or make it interfere less with the functions of the cell. For example, one may produce a protein preceded by a signal peptide, which directs the translation product into the endoplasmic reticulum, by including in the construct (i.e. expression cassette) sequences encoding a signal peptide (such sequences may also be called the "signal sequence"). The signal sequence used could be, for example, one associated with the gene encoding the polypeptide, or it may be taken from another gene.

There are many signal peptides described in the literature, and they are largely interchangeable (Raikhel and Chrispeels, "Protein sorting and vesicle traffic" in Buchanan et al., eds, (2000) *Biochemistry and Molecular Biology of Plants* (American Society of Plant Physiologists, Rockville, Md.), herein incorporated by reference). The addition of a signal peptide will result in the translation product entering the endoplasmic reticulum (in the process of which the signal peptide itself is removed from the polypeptide), but the final intracellular location of the protein depends on other factors, which may be manipulated to result in localization most appropriate for the pathogen and cell type. The default pathway, that is, the pathway taken by the polypeptide if no other targeting labels are included, results in secretion of the polypeptide across the cell membrane (Raikhel and Chrispeels, supra) into the apoplast. The apoplast is the region outside the plasma membrane system and includes cell walls, intercellular spaces, and the xylem vessels that form a continuous, permeable system through which water and solutes may move. This will often be a suitable location. In particular embodiments, a nucleotide sequence encoding a barley alpha-amylase (BAA) signal peptide is joined in frame with a polynucleotide of the invention. The nucleotide sequence encoding the BAA signal peptide and the amino acid sequence for the BAA signal peptide are set forth in SEQ ID NO:112 and SEQ ID NO:113, respectively.

Other pathogens may be more effectively combated by locating the peptide within the cell rather than outside the cell membrane. This can be accomplished, for example, by adding an endoplasmic reticulum retention signal encoding sequence to the sequence of the gene. Methods and sequences for doing this are described in Raikhel and Chrispeels, supra; for example, adding sequences encoding the amino acids K, D, E and L in that order, or variations thereof described in the literature, to the end of the protein coding portion of the polypeptide will accomplish this. ER retention sequences are well known in the art and include, for example, KDEL (SEQ ID NO:114), SEKDEL (SEQ ID NO:115), HDEL (SEQ ID NO:116), and HDEF (SEQ ID NO:117). See, for example, Denecke et al. (1992). *EMBO J.* 11:2345-2355; Wandelt et al. (1992) *Plant J.* 2:181-192; Denecke et al. (1993) *J. Exp. Bot.* 44:213-221; Vitale et al. (1993) *J. Exp. Bot.* 44:1417-1444; Gomord et al. (1996) *Plant Physiol. Biochem.* 34:165-181; Lehmann et al. (2001) *Plant Physiol.* 127 (2): 436-449.

Alternatively, the use of vacuolar targeting labels such as those described by Raikhel and Chrispeels, supra, in addition to a signal peptide will result in localization of the peptide in a vacuolar structure. As described in Raikhel and Chrispeels, supra, the vacuolar targeting label may be placed in different positions in the construct. Use of a plastid transit peptide encoding sequence instead of a signal peptide encoding sequence will result in localization of the polypeptide in the plastid of the cell type chosen (Raikhel and Chrispeels, supra). Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481. Chloroplast targeting sequences that encode such transit peptides are also known in the art and include the chloroplast small subunit of ribulose-1,5-bisphosphate carboxylase (Rubisco) (de Castro Silva Filho et al. (1996) *Plant Mol. Biol.* 30:769-780; Schnell et al. (1991) *J. Biol. Chem.* 266(5):3335-3342); 5-(enolpyruvyl)shikimate-3-phosphate synthase (EPSPS) (Archer et al. (1990) *J. Bioenerg. Biomemb.* 22(6):789-810); tryptophan synthase (Zhao et al. (1995) *J. Biol. Chem.* 270(11):6081-6087); plastocyanin (Lawrence et al. (1997) *J. Biol. Chem.* 272(33):20357-20363); chorismate synthase (Schmidt et al. (1993) *J. Biol. Chem.* 268(36):27447-27457); and the light harvesting chlorophyll a/b binding protein (LHBP) (Lamppa et al. (1988) *J. Biol. Chem.* 263:14996-14999). A person skilled in the art could also envision generating transgenic plants in which the chloroplasts have been transformed to overexpress a gene for an antipathogenic peptide. See, for example, Daniell (1999) *Nature Biotech* 17:855-856; and U.S. Pat. No. 6,338,168.

One could also envision localizing the antipathogenic polypeptide in other cellular compartments by addition of suitable targeting information. (Raikhel and Chrispeels, supra). A useful site available on the world wide web that provides information and references regarding recognition of the various targeting sequences can be found at: psort.nibb.ac.jp/mit. Other references regarding the state of the art of protein targeting include Silva-Filho (2003) *Curr. Opin. Plant Biol.* 6:589-595; Nicchitta (2002) *Curr. Opin. Cell Biol.* 14:412-416; Bruce (2001) *Biochim Biophys Acta* 1541: 2-21; Hadlington & Denecke (2000) *Curr. Opin. Plant Biol.* 3: 461-468; Emanuelsson et al. (2000) *J Mol. Biol.* 300: 1005-1016; Emanuelsson & von Heijne (2001) *Biochim Biophys Acta* 1541: 114-119, herein incorporated by reference.

In nature, some polypeptides are produced as complex precursors which, in addition to targeting labels such as the signal peptides discussed elsewhere in this application, also contain other fragments of peptides which are removed (processed) at some point during protein maturation, resulting in a mature form of the polypeptide that is different from the primary translation product (aside from the removal of the signal peptide). "Mature protein" refers to a post-translationally processed polypeptide; i.e., one from which any pre- or propeptides present in the primary translation product have been removed. "Precursor protein" or "prepropeptide" or "preproprotein" all refer to the primary product of translation of mRNA; i.e., with pre- and propeptides still present. Pre- and propeptides may include, but are not limited to, intracellular localization signals. "Pre" in this nomenclature generally refers to the signal peptide. The form of the translation product with only the signal peptide removed but no further processing yet is called a "propeptide" or "proprotein." The fragments or segments to be removed may themselves also be referred to as "propeptides." A proprotein or propeptide thus has had the signal peptide removed, but contains propeptides (here referring to propeptide segments) and the portions that will make up the mature protein. The skilled artisan is able to determine, depending on the species in which the proteins are being expressed and the desired intracellular location, if higher expression levels might be obtained by using a gene construct encoding just the mature form of the protein, the mature form with a signal peptide, or the proprotein (i.e., a form including propeptides) with a signal peptide. For optimal expression in plants or fungi, the pre- and propeptide sequences may be needed. The propeptide segments may play a role in aiding correct peptide folding.

The polynucleotides of the present invention can be expressed in a host cell, such as a bacterial, fungal, yeast, insect, mammalian, or preferably plant cells. By "host cell" is meant a cell which comprises a heterologous polynucleotide of the invention. Host cells may be prokaryotic cells, such as *E. coli*, or eukaryotic cells, such as yeast, insect, amphibian, or mammalian cells. In some embodiments, host cells are monocotyledonous or dicotyledonous plant cells. In particular embodiments, the monocotyledonous host cell is a maize host cell.

The antipathogenic polynucleotides of the invention can be provided in expression cassettes for expression in an organism of interest. The expression cassettes of the invention find use in generating transformed plants, plant cells, and microorganisms and in practicing the methods for inducing pathogen resistance disclosed herein. The cassette will include 5' and 3' regulatory sequences operably linked to an antipathogenic polynucleotide of the invention. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide that encodes an antipathogenic polypeptide to be under the transcriptional regulation of the regulatory regions.

The expression cassette will include in the 5'-3' direction of transcription, a transcriptional and translational initiation region (i.e., a promoter), a polynucleotide of the invention, and a transcriptional and translational termination region (i.e., termination region) functional in the host organism. The regulatory regions (i.e., promoters, transcriptional regulatory regions, and translational termination regions) and/or the polynucleotide of the invention may be native/analogous to the host cell or to each other. Alternatively, the regulatory regions and/or the polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The optionally included termination region may be native with the transcriptional initiation region, may be native with the operably linked polynucleotide of interest, may be native with the plant host, or may be derived from another source (i.e., foreign or heterologous) to the promoter, the polynucleotide of interest, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639. In particular embodiments, the potato proteinase inhibitor II gene (PinII) terminator is used. See, for example, Keil et al. (1986) *Nucl. Acids Res.* 14:5641-5650; and An et al. (1989) *Plant Cell* 1:115-122, herein incorporated by reference in their entirety.

Where appropriate, the polynucleotides may be optimized for increased expression in the transformed organism. For example, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (Virology 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention, including the native promoter of the polynucleotide sequence of interest. The promoters can be selected based on the desired outcome. A wide range of plant promoters are discussed in the review of Potenza et al. (2004) *In Vitro Cell Dev Biol—Plant* 40:1-22, herein incorporated by reference. For example, the nucleic acids can be combined with constitutive, tissue-preferred, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200) and the inducible maize promoters described in U.S. Pat. No. 6,429,362 (e.g., Zm-PR1-81 and Zm-PR1-83 promoters), all of which are herein incorporated by reference in their entirety. The promoters described in U.S. Pat. No. 6,720,480, such as the Zm-BB11 promoter, may also be used in the practice of the invention.

Additionally, as pathogens find entry into plants through wounds or insect damage, a wound-inducible promoter, which includes a pathogen-inducible promoter, may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzene-sulfonamide herbicide safeners, the maize GST promoter, which is activated by hydrophobic electrophilic compounds that are used as pre-emergent herbicides, and the tobacco PR-la promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of the antipathogenic polypeptides of the invention within a particular plant tissue. For example, a tissue-preferred promoter may be used to express an antipathogenic polypeptide in a plant tissue where disease resistance is particularly important, such as, for example, the roots or the leaves. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Vascular tissue-preferred promoters are known in the art and include those promoters that selectively drive protein expression in, for example, xylem and phloem tissue. Vascular tissue-preferred promoters include, but are not limited to, the *Prunus serotina* prunasin hydrolase gene promoter (see, e.g., International Publication No. WO 03/006651), and also those found in U.S. Pat. No. 6,921,815.

Stalk-preferred promoters may be used to drive expression of an antipathogenic polypeptide of the invention. Exemplary stalk-preferred promoters include the maize MS8-15 gene promoter (see, for example, U.S. Pat. No. 5,986,174 and International Publication No. WO 98/00533), and those found in Graham et al. (1997) *Plant Mol Biol* 33(4): 729-735. In certain embodiments of the invention, the Zm-419 promoter is used for tissue preferred-expression in maize stalk tissue. See, for example, International Publication No. WO 2007/050509 and U.S. Pat. No. 7,538,261.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is an endosperm-specific promoter. Globulin 1 (Glb-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, Globulin 1, etc. See also WO 00/12733, where seed-preferred promoters from end1 and end2 genes are disclosed; herein incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Bairn et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived PL promoter and N-gene ribosome binding site (Simatake and Rosenberg (1981) *Nature* 292:128). Examples of selection markers for *E. coli* include, for example, genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva et al. (1983) *Gene* 22:229-235 and Mosbach et al. (1983) *Nature* 302:543-545).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous nucleotide sequences in yeast is well known. Sherman, F., et al. (1982) *Methods in Yeast Genetics*, Cold Spring Harbor Laboratory is a well recognized work describing the various methods available to produce proteins in yeast. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like, as desired.

A protein of the present invention, once expressed, can be isolated from yeast by lysing the cells and applying standard protein isolation techniques to the lysates. The monitoring of the purification process can be accomplished by using Western blot techniques, radioimmunoassay, or other standard immunoassay techniques.

The sequences of the present invention can also be ligated to various expression vectors for use in transfecting cell cultures of, for instance, mammalian, insect, or plant origin. Illustrative cell cultures useful for the production of the peptides are mammalian cells. A number of suitable host cell lines capable of expressing intact proteins have been developed in the art, and include the HEK293, BHK21, and CHO cell lines. Expression vectors for these cells can include expression control sequences, such as an origin of replication, a promoter (e.g. the CMV promoter, a HSV tk promoter or pgk (phosphoglycerate kinase) promoter), an enhancer (Queen et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (See, Schneider (1987) *J. Embryol. Exp. Morphol.* 27:353-365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague, et al. (1983) *J. Virol.* 45:773-781). Additionally, gene sequences to control replication in the host cell may be incorporated into the vector such as those found in bovine papilloma virus type-vectors. Saveria-Campo, M., (1985) Bovine Papilloma Virus DNA a Eukaryotic Cloning Vector in *DNA Cloning Vol. II a Practical Approach*, D. M. Glover, Ed., IRL Press, Arlington, Va. pp. 213-238.

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics, and micro-injection of the DNA directly into the cells. The transfected cells are cultured by means well known in the art. Kuchler, R. J. (1997) *Biochemical Methods in Cell Culture and Virology*, Dowden, Hutchinson and Ross, Inc.

In certain embodiments, the polynucleotides of the present invention can be stacked with any combination of polynucleotide sequences of interest in order to create plants with a desired phenotype. For example, the polynucleotides of the present invention may be stacked with other antipathogenic genes and the like. The combinations generated can also include multiple copies of any one of the polynucleotides of interest. The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins (U.S. Pat. No. 6,858,778); and thioredoxins (U.S. Pat. No. 7,009,087)); the disclosures of which are herein incorporated by reference.

The polynucleotides of the present invention can also be stacked with traits desirable for insect, disease, or herbicide resistance (e.g., *Bacillus thuringiensis* toxic proteins (U.S. Pat. Nos. 5,366,892; 5,747,450; 5,737,514; 5,723,756; 5,593,881; Geiser et al. (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest.

This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods. Polypeptides can also be introduced to a plant in such a manner that they gain access to the interior of the plant cell or remain external to the cell but in close contact with it.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055 and U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. Nos. 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lecl transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the antipathogenic sequences of the invention can be provided to a plant using a variety of transient transformation methods. Such transient transformation methods include, but are not limited to, the introduction of the antipathogenic protein or variants and fragments thereof directly into the plant or the introduction of antipathogenic protein transcript into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which its released to become integrated into the genome is greatly reduced. Such methods include the use particles coated with polyethylimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. It is recognized that the antipathogenic polypeptide of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in a transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

Pedigree breeding starts with the crossing of two genotypes, such as an elite line of interest and one other elite inbred line having one or more desirable characteristics (i.e., having stably incorporated a polynucleotide of the invention, having a modulated activity and/or level of the polypeptide of the invention, etc) which complements the elite line of interest. If the two original parents do not provide all the desired characteristics, other sources can be included in the breeding population. In the pedigree method, superior plants are selfed and selected in successive filial generations. In the succeeding filial generations, the heterozygous condition gives way to homogeneous lines as a result of self-pollination and selection. Typically in the pedigree method of breeding, five or more successive filial generations of selfing and selection is practiced: F1→F2; F2→F3; F3÷F4; F4→$F_5$, etc. After a sufficient amount of inbreeding, successive filial generations will serve to increase seed of the developed inbred. In specific embodiments, the inbred line comprises homozygous alleles at about 95% or more of its loci.

In addition to being used to create a backcross conversion, backcrossing can also be used in combination with pedigree breeding to modify an elite line of interest and a hybrid that is made using the modified elite line. As discussed previously, backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, an embodiment of this invention is a method of making a backcross conversion of maize inbred line of interest, comprising the steps of crossing a plant of maize inbred line of interest with a donor plant comprising a mutant gene or transgene conferring a desired trait (i.e., increased pathogen resistance), selecting an F1 progeny plant comprising the mutant gene or transgene conferring the desired trait, and backcrossing the selected F1 progeny plant to the plant of maize inbred line of interest. This method may further comprise the step of obtaining a molecular marker profile of maize inbred line of interest and using the molecular marker profile to select for a progeny plant with the desired trait and the molecular marker profile of the inbred line of interest. In the same manner, this method may be used to produce an F1 hybrid seed by adding a final step of crossing the desired trait conversion of maize inbred line of interest with a different maize plant to make F1 hybrid maize seed comprising a mutant gene or transgene conferring the desired trait.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny, selfed progeny and toperossing. The selected progeny are cross-pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation breeding is one of many methods that could be used to introduce new traits into an elite line. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcros sing. Details of mutation breeding can be found in "Principals of Cultivar Development" Fehr, 1993 Macmillan Publishing Company the disclosure of which is incorporated herein by reference. In addition, mutations created in other lines may be used to produce a backcross conversion of elite lines that comprises such mutations.

As used herein, the term plant also includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used to induce pathogen resistance or protect from pathogen attack any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean and plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The compositions of the invention find further use in methods directed to protecting a plant from a pathogen. "Protecting a plant from a pathogen" is intended to mean killing the pathogen or preventing or limiting disease formation on a plant. In some embodiments, an antipathogenic composition comprising an antipathogenic polypeptide and a carrier is applied directly to the environment of a plant pathogen, such as, for example, on a plant or in the soil or other growth medium surrounding the roots of the plant, in order to protect the plant from pathogen attack. Microorganisms comprising a polynucleotide encoding an antipathogenic protein of the invention and methods of using them to protect a plant from a pathogen are further provided. In some embodiments, the transformed microorganism is applied directly to a plant or to the soil in which a plant grows.

Antipathogenic compositions, particularly antifungal compositions, are also encompassed by the present invention. Antipathogenic compositions may comprise antipathogenic polypeptides or microorganisms comprising a heterologous polynucleotide that encodes an antipathogenic polypeptide. The antipathogenic compositions of the invention may be applied to the environment of a plant pathogen, as described herein below, thereby protecting a plant from pathogen attack. Moreover, an antipathogenic composition can be formulated with an acceptable carrier that is, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

The antipathogenic compositions find further use in the decontamination of plant pathogens during the processing of grain for animal or human food consumption; during the processing of feedstuffs, and during the processing of plant material for silage. In this embodiment, the antipathogenic compositions of the invention are presented to grain, plant material for silage, or a contaminated food crop, or during an appropriate stage of the processing procedure, in amounts effective for antimicrobial activity.

A polynucleotide encoding an antipathogenic, particularly antifungal, polypeptide of the invention may be introduced into any suitable microbial host according to standard methods in the art. For example, microorganism hosts that are known to occupy the "phytosphere" (phylloplane, phyllosphere, rhizosphere, and/or rhizoplane) of one or more crops of interest may be selected. These microorganisms are selected so as to be capable of successfully competing in the particular environment with the wild-type microorganisms, and to provide for stable maintenance and expression of the gene expressing the antipathogenic protein.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinelandii* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

Other illustrative prokaryotes, both Gram-negative and gram-positive, include *Enterobacteriaceae*, such as *Escherichia, Erwinia, Shigella, Salmonella*, and *Proteus; Bacil-*

*laceae; Rhizobiaceae*, such as *Rhizobium; Spirillaceae*, such as photobacterium, *Zymomonas, Serratia, Aeromonas, Vibrio, Desulfovibrio, Spirillum; Lactobacillaceae; Pseudomonadaceae*, such as *Pseudomonas* and *Acetobacter; Azotobacteraceae* and *Nitrobacteraceae*. Among eukaryotes are fungi, such as *Phycomycetes* and *Ascomycetes*, which includes yeast, such as *Saccharomyces* and *Schizosaccharomyces*; and *Basidiomycetes* yeast, such as *Rhodotorula, Aureobasidium, Sporobolomyces*, and the like.

Microbial host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonas fluorescens, Saccharomyces cerevisiae, Bacillus thuringiensis, Escherichia coli, Bacillus subtilis*, and the like.

Polynucleotides encoding the antipathogenic proteins of the invention can be introduced into microorganisms that multiply on plants (epiphytes) to deliver antipathogenic proteins to potential target pests. Epiphytes, for example, can be gram-positive or gram-negative bacteria.

Root-colonizing bacteria, for example, can be isolated from the plant of interest by methods known in the art. Specifically, a *Bacillus cereus* strain that colonizes roots can be isolated from roots of a plant (see, for example, Handelsman et al. (1991) *Appl. Environ. Microbiol.* 56:713-718). Polynucleotides encoding the antipathogenic polypeptides of the invention can be introduced into a root-colonizing *Bacillus cereus* by standard methods known in the art.

Polynucleotides encoding antipathogenic proteins can be introduced, for example, into the root-colonizing *Bacillus* by means of electrotransformation. Specifically, polynucleotides encoding the antipathogenic proteins can be cloned into a shuttle vector, for example, pHT3101 (Lerecius et al. (1989) *FEMS Microbiol. Letts.* 60: 211-218. The shuttle vector pHT3101 containing the coding sequence for the particular antipathogenic protein can, for example, be transformed into the root-colonizing *Bacillus* by means of electroporation (Lerecius et al. (1989) *FEMS Microbiol. Letts.* 60: 211-218).

Methods are provided for protecting a plant from a pathogen comprising applying an effective amount of an antipathogenic protein or composition of the invention to the environment of the pathogen. "Effective amount" is intended to mean an amount of a protein or composition sufficient to control a pathogen. The antipathogenic proteins and compositions can be applied to the environment of the pathogen by methods known to those of ordinary skill in the art.

Prior to the application of an antipathogenic composition of the invention to an area of cultivation, the environment can be evaluated to determine if the pathogen of interest is present or if conditions are conducive to pathogen growth or infestation. As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc), a greenhouse, a growth chamber, etc. Evaluation of the environment can aid in determining the effective amount of the antipathogenic protein or composition of the invention needed to control a pathogen within an area of cultivation.

Environmental conditions that can be evaluated include, but are not limited to, ground and surface water pollution concerns, intended use of the crop, crop tolerance, soil residuals, weeds present in area of cultivation, humidity, soil texture, pH of soil, amount of organic matter in soil, water content of soil, application equipment, and tillage practices.

Following the evaluation of the environmental conditions, an effective amount of an antipathogenic composition of the invention can be applied to the crop, crop part, seed of the crop or area of cultivation.

The antipathogenic compositions of the invention may be obtained by the addition of a surface-active agent, an inert carrier, a preservative, a humectant, a feeding stimulant, an attractant, an encapsulating agent, a binder, an emulsifier, a dye, a UV protective, a buffer, a flow agent or fertilizers, micronutrient donors, or other preparations that influence plant growth. One or more agrochemicals including, but not limited to, herbicides, insecticides, fungicides, bactericides, nematicides, molluscicides, acaricides, plant growth regulators, harvest aids, and fertilizers, can be combined with carriers, surfactants or adjuvants customarily employed in the art of formulation or other components to facilitate product handling and application for particular target pathogens. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area, plant, or seed to be treated. For example, the compositions of the present invention may be applied to grain in preparation for or during storage in a grain bin or silo, etc. The compositions of the present invention may be applied simultaneously or in succession with other compounds. Methods of applying an active ingredient of the present invention or an agrochemical composition of the present invention that contains at least one of the antipathogenic proteins, more particularly antifungal proteins, of the present invention include, but are not limited to, foliar application, seed coating, and soil application. The number of applications and the rate of application depend on the intensity of infestation by the corresponding pest or pathogen.

Suitable surface-active agents include, but are not limited to, anionic compounds such as a carboxylate of, for example, a metal; carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The antipathogenic compositions of the present invention can be in a suitable form for direct application or as a concentrate of primary composition that requires dilution with a suitable quantity of water or other diluent before application. The concentration of the antipathogenic polypeptide will vary depending upon the nature of the particular formulation, specifically, whether it is a concentrate or to be used directly. The composition contains 1 to 98% of a solid or liquid inert carrier, and 0 to 50%, optimally 0.1 to 50% of a surfactant. These compositions will be administered at the labeled rate for the commercial product, optimally about 0.01 lb-5.0 lb. per acre when in dry form and at about 0.01 pts.-10 pts. per acre when in liquid form.

In a further embodiment, the compositions, as well as the transformed microorganisms and antipathogenic proteins, of the invention can be treated prior to formulation to prolong the antipathogenic, particularly antifungal, activity when applied to the environment of a target pathogen as long as the pretreatment is not deleterious to the activity. Such treatment can be by chemical and/or physical means as long as the treatment does not deleteriously affect the properties of the composition(s). Examples of chemical reagents include but are not limited to halogenating agents; aldehydes such a formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W.H. Freeman and Co.).

The antipathogenic compositions of the invention can be applied to the environment of a plant pathogen by, for example, spraying, atomizing, dusting, scattering, coating or pouring, introducing into or on the soil, introducing into irrigation water, by seed treatment or general application or dusting at the time when the pathogen has begun to appear or before the appearance of pathogens as a protective measure. For example, the antipathogenic protein and/or transformed microorganisms of the invention may be mixed with grain to protect the grain during storage. It is generally important to obtain good control of pathogens in the early stages of plant growth, as this is the time when the plant can be most severely damaged. In one embodiment of the invention, the composition is applied directly to the soil, at a time of planting, in granular form of a composition of a carrier and antipathogenic polypeptides or transformed microorganisms of the invention. Another embodiment is a granular form of a composition comprising an agrochemical such as, for example, a herbicide, an insecticide, a fertilizer, an inert carrier, and antipathogenic polypeptides or transformed microorganisms of the invention.

Compositions of the invention find use in protecting plants, seeds, and plant products in a variety of ways. For example, the compositions can be used in a method that involves placing an effective amount of the antipathogenic, more particularly, antifungal, composition in the environment of the pathogen by a procedure selected from the group consisting of spraying, dusting, broadcasting, or seed coating.

The time at which an antipathogenic composition is applied to an area of interest (and any plants therein) may be important in optimizing pathogen control. The time at which an antipathogenic composition is applied may be determined with reference to the size of plants and/or the stage of growth and/or development of plants in the area of interest. The stages of growth and/or development of plants are known in the art. For example, soybean plants normally progress through vegetative growth stages known as VE (emergence), VC (cotyledon), V1 (unifoliate), and V2 to VN. Soybeans then switch to the reproductive growth phase in response to photoperiod cues; reproductive stages include R1 (beginning bloom), R2 (full bloom), R3 (beginning pod), R4 (full pod), R5 (beginning seed), R6 (full seed), R7 (beginning maturity), and R8 (full maturity). Corn plants normally progress through the following vegetative stages VE (emergence); V1 (first leaf); V2 (second leaf); V3 (third leaf); V(n) (Nth/leaf); and VT (tasseling). Progression of maize through the reproductive phase is as follows: R1 (silking); R2 (blistering); R3 (milk); R4 (dough); R5 (dent); and R6 (physiological maturity). Cotton plants normally progress through VE (emergence), VC (cotyledon), V1 (first true leaf), and V2 to VN. Then, reproductive stages beginning around V14 include R1 (beginning bloom), R2 (full bloom), R3 (beginning boll), R4 (cutout, boll development), R5 (beginning maturity, first opened boll), R6 (maturity, 50% opened boll), and R7 (full maturity, 80-90% open bolls). Thus, for example, the time at which an antipathogenic composition or other chemical is applied to an area of interest in which plants are growing may be the time at which some or all of the plants in a particular area have reached at least a particular size and/or stage of growth and/or development, or the time at which some or all of the plants in a particular area have not yet reached a particular size and/or stage of growth and/or development.

One of skill in the art will appreciate that the compositions and methods disclosed herein can be used with other compositions and methods available in the art for protecting plants from insect and pathogen attack. For example, methods of the invention can comprise the use of one or more herbicides, insecticides, fungicides, nematocides, bactericides, acaricides, growth regulators, chemosterilants, semiochemicals, repellents, attractants, pheromones, feeding stimulants or other biologically active compounds or entomopathogenic bacteria, virus, or fungi to form a multi-component mixture giving an even broader spectrum of agricultural protection. General references for these agricultural protectants include The Pesticide Manual, 13th Edition, C. D. S. Tomlin, Ed., British Crop Protection Council, Farnham, Surrey, U.K., 2003 and The BioPesticide Manual, 2nd Edition, L. G. Copping, Ed., British Crop Protection Council, Farnham, Surrey, U.K., 2001.

Before plant propagation material (fruit, tuber, bulb, corm, grains, seed), but especially seed, is sold as a commercial product, it is customarily treated with a protective coating comprising herbicides, insecticides, fungicides, bactericides, nematicides, molluscicides, or mixtures of several of these preparations, if desired together with further carriers, surfactants, or application-promoting adjuvants customarily employed in the art of formulation to provide protection against damage caused by bacterial, fungal, or animal pests. In order to treat the seed, the protective coating may be applied to the seeds either by impregnating the tubers or grains with a liquid formulation or by coating them with a combined wet or dry formulation. In addition, in special cases, other methods of application to plants are possible, e.g., treatment directed at the buds or the fruit.

The plant seed of the invention comprising a polynucleotide encoding an antipathogenic polypeptide of the invention may be treated with a seed protective coating comprising a seed treatment compound, such as, for example, captan, carboxin, thiram, methalaxyl, pirimiphos-methyl, and others that are commonly used in seed treatment. Alternatively, a seed of the invention comprises a seed protective coating comprising an antipathogenic, more particularly antifungal, composition of the invention used alone or in combination with one of the seed protective coatings customarily used in seed treatment.

In an embodiment of the invention, the antipathogenic compositions of the invention may be used as a pharmaceutical composition for treatment of fungal and microbial pathogens in humans and other animals. Diseases and disorders caused by fungal and microbial pathogens include but are not limited to fungal meningoencephalitis, superficial fungal infections, ringworm, Athlete's foot, histoplasmosis, candidiasis, thrush, coccidioidoma, pulmonary cryptococcus, trichosporonosis, piedra, tinea nigra, fungal keratitis, onychomycosis, tinea capitis, chromomycosis, aspergillosis, endobronchial pulmonary aspergillosis, mucormycosis, chromoblastomycosis, dermatophytosis, tinea, fusariosis, pityriasis, mycetoma, pseudallescheriasis, and sporotrichosis.

In some of these embodiments, the antipathogenic polypeptide is combined with a pharmaceutically acceptable carrier. As used herein the term "pharmaceutically acceptable carrier" includes solvents, dispersion media, coatings, antibacterial and antifungal agents, isotonic and absorption delaying agents, and the like, compatible with pharmaceutical administration. Supplementary active compounds also can be incorporated into the compositions.

In particular, the antipathogenic polypeptides of the invention and pharmaceutical compositions comprising the same may be used to provide treatment for diseases and disorders associated with, but not limited to, the following fungal pathogens: *Histoplasma capsulatum, Candida* spp. (*C. albicans, C. tropicalis, C. parapsilosis, C. guilliermondii, C. glabrata/Torulopsis glabrata, C. krusei, C. lusitaniae*), *Aspergillus fumigatus, A. flavus, A. niger, Rhizopus* spp., *Rhizomucor* spp., *Cunninghamella* spp., *Apophysomyces* spp., *Saksenaee* spp., *Mucor* spp., and *Absidia* spp. Efficacy of the compositions of the invention as anti-fungal treatments may be determined through anti-fungal assays known to one in the art.

The presently disclosed pharmaceutical compositions may be administered to a patient through numerous means. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 μg/kg to about 15 mg/kg (e.g., 0.1 to 20 mg/kg) of active compound is an initial candidate dosage for administration to the patient, whether, for example, by one or more separate administrations, or by continuous infusion. A typical daily dosage might range from about 1 μg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

"Treatment" is herein defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A "therapeutic agent" comprises, but is not limited to, the polypeptides and pharmaceutical compositions of the invention.

The antipathogenic polypeptides of the invention can be used for any application including coating surfaces to target microbes. In this manner, target microbes include human pathogens or microorganisms. Surfaces that might be coated with the antipathogenic compositions of the invention include carpets and sterile medical facilities. Polymer bound polypeptides of the invention may be used to coat surfaces. Methods for incorporating compositions with antimicrobial properties into polymers are known in the art. See U.S. Pat. No. 5,847,047 herein incorporated by reference.

The embodiments of the present invention may be effective against a variety of plant pathogens, particularly fungal pathogens, such as, for example, *Fusarium graminearum*. Pathogens of the invention include, but are not limited to, viruses or viroids, bacteria, fungi, and the like. Viruses include any plant virus, for example, tobacco or cucumber mosaic virus, ringspot virus, necrosis virus, maize dwarf mosaic virus, etc. Fungal pathogens, include but are not limited to, *Colletotrichum graminocola, Diplodia maydis, Fusarium graminearum*, and *Fusarium verticillioides*. Specific pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colle-*

*totichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythium aphanidermatum, Pythium ultimum, Pythium debaryanum*, Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassicicola, Pythium ultimum, Peronospora parasitica, Fusarium roseum, Alternaria alternata*; Alfalfa: *Clavibacter michiganese subsp. insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium oxysporum, Verticillium albo-atrum, Xanthomonas campestris* p.v. *alfalfae, Aphanomyces euteiches, Stemphylium herbarum, Stemphylium alfalfae, Colletotrichum trifolii, Leptosphaerulina briosiana, Uromyces striatus, Sclerotinia trifoliorum, Stagonospora meliloti, Stemphylium botryosum, Leptotrichila medicaginis*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum*, High Plains Virus, European wheat striate virus; Sunflower: *Plasmopora halstedii, Sclerotinia sclerotiorum*, Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Colletotrichum graminicola, Fusarium moniliforme* var. *subglutinans, Erwinia stewartii, F. verticillioides, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense subsp. nebraskense, Trichoderma viride*, Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora*, Corn stunt *spiroplasma, Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; *Sorghum: Exserohilum turcicum, C. sublineolum, Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi*, Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*, etc.

It is to be noted that the term “a” or “an” entity refers to one or more of that entity; for example, “a polypeptide” is understood to represent one or more polypeptides. As such, the terms “a” (or “an”), “one or more,” and “at least one” can be used interchangeably herein.

Throughout this specification and the claims, the words “comprise,” “comprises,” and “comprising” are used in a non-exclusive sense, except where the context requires otherwise.

As used herein, the term “about,” when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the presently disclosed subject matter be limited to the specific values recited when defining a range.

Unless defined otherwise, all technical and scientific terms used herein have the same meaning as commonly understood by one of skill in the art to which the invention pertains. Although any methods and materials similar herein can be used in the practice or testing of the present invention, the preferred methods and materials are described herein.

The following examples are offered by way of illustration and not by way of limitation.

EXPERIMENTAL

Example 1

Isolation of Antifungal Polypeptides from *Fusarium verticillioides* and *Colletotrichum graminicola*

*F. verticillioides* (FVE) and *C. graminicola* (CGR) fungal strains were part of an in-house collection. Each isolate (FVE=FMO33 and CGR=Eau Claire, Wis.) was grown 4 days at 28° C. in 100 mL of YPD medium (Pioneer recipe 60I). Cells were pelleted and rinsed twice in 100 mL of FRIES MS medium. The cell pellets were resuspended in 100 mL of FRIES MS and incubated for three more days at 28° C. Cell pellets were rinsed once in 200 mM $CaCl_2$ then twice in PBS buffer before lyophilization. The lyophilized tissue was extracted with extraction buffer (Y-PER+Complete Protease Inhibitor Cocktail, diluted 1:6 in $H_2O$) at a ratio of 50 mg tissue to 1 mL extraction buffer for at least one hour, with shaking, at 4° C. The lysed cells were pelleted at 14,000 RPM for 15 minutes at 4° C. The supernatants were removed and the extraction was repeated. Supernatants were then pooled.

Oasis HLB extraction cartridges (1 gram, 20 mL) (Waters Corporation, Milford, Mass.) were used for solid phase extraction (SPE). Specifically, the SPE cartridge was made wet with one cartridge volume of methanol and then conditioned with approximately 120 mL Solvent A (2% acetonitrile, 0.1% TFA). Approximately 2 mL of crude culture extract was treated with 10× solvent A to a final concentration of 1× and centrifuged for 15 min at 3,000×g. The supernatant was loaded onto the SPE cartridge, and the SPE cartridge was washed with approximately 10 mL solvent A. The SPE cartridge was eluted with approximately 20 mL 95% acetonitrile, 0.1% TFA. The eluted sample was partially dried in a centrifugal evaporator (Savant Speed-Vac), frozen with liquid nitrogen, and lyophilized to dryness.

The dried extract was re-suspended in ¼× phosphate-buffered saline (PBS) buffer (~2 mL) and the re-suspended extract was enriched for proteins using a Sephadex G10 (Amersham Biosciences AB, Uppsala, Sweden) spin column. Bio-Spin disposable chromatography columns (Bio-Rad Laboratories, Hercules Calif.) were filled to approximately 0.75 mL bed volume with Sephadex G10 that had been pre-equilibrated in ¼×PBS and were centrifuged for 1 minute at 1,000×g. 200 μL of SPE extract in ¼×PBS was added to each pre-spun Bio-Spin column, and loaded Bio-Spin columns were centrifuged for 5 minutes at 1,000×g to elute proteins.

Antifungal extracts were fractionated by HPLC with a Jupiter 5μ C5 300 Å 150 mm×4.6 mm column (Phenomenex, Torrance, Calif.). HPLC starting conditions were 0.5% acetonitrile, 0.04% heptafluorobutyric acid (HFBA), 0.4 mL/minute. Following injection, the flow rate was raised to 0.8 mL/minute over 1 minute. A 4 minute linear gradient (Waters gradient curve 6, Waters Corporation, Milford, Mass.) was started to 20% acetonitrile, 0.04% HFBA. The 20% acetonitrile, 0.04% HFBA was held for 3 additional minutes before starting a linear gradient (Waters gradient curve 6, Waters Corporation, Milford, Mass.) for 68 minutes to 60% acetonitrile, 0.04% HFBA. 30 second fractions were collected into ½ area 96 well clear bottom assay plates. Plates containing fractionated extracts were then dried in a centrifugal evaporator. The dried fractionated extracts were then screened for antifungal activity against *Fusarium graminearum* (FGR) using an antifungal plate assay, as described in Example 2. Assays were performed in ½ area 96 well clear bottom plates. FGR was used at 4,000 spores/mL in ¼× potato dextrose broth (Becton Dickinson Microbiology Systems, Sparks, Md.). Cultures were allowed to develop at 27° C. for 24 hours. Assays were scored by visualizing fungal growth with an inverted microscope. The HPLC fractions from approximately 66.0 to 77.5 (FVE) minutes and 40.0 to 44.0 minutes (CGR) were found to have antifungal activity against FGR (See Example 2 and Table 2).

For the FVE fraction, additional HPLC fractionations were performed to bulk up the antifungal fraction. This bulked up antifungal fraction was further purified using μ-bore HPLC with a Zorbax 300SB C18 1.0 mm×150 mm column (Agilent Technologies). Starting conditions were 14% acetonitrile, 0.08% formic acid, 0.02% trifluoroacetic acid (TFA), 50 μL/minute. Two minutes following sample injection, an 84 minute linear gradient was started to 40% acetonitrile, 0.08% formic acid, 0.02% TFA. 214 nm peak based fractions were collected using an Agilent micro-fraction collector, dried in a centrifugal evaporator, and assayed for antifungal activity as described above. A peak eluting at approximately 35 minutes was found to have activity against FGR. ESI mass spectra were obtained on an integrated Agilent MSD TOF mass spectrometer. The mass of the peptide was determined to be 8,135 Da. Reduction and iodoacetamide alkylation did not affect the mass of the peptide, indicating that the peptide lacked cysteine residues and disulfide bonds. Initial N-terminal sequencing yielded the following partial sequence of the peptide:

(SEQ ID NO. 5)
TEGATGSVRPTGGSGDAFQRREKASXDYAI

The complete sequence of the FvAFP1 was identified with a coding sequence having the nucleotide sequence set forth in SEQ ID NO: 1 and an amino acid sequence set forth in SEQ ID NO: 2 for the full-length polypeptide. The full-length proprotein FvAFP1 polypeptide is provided below with the predicted mature peptide underlined. The predicted mature peptide has a mass of 8135 Da, which matches the mass of the isolated polypeptide.

(SEQ ID NO: 2)
MLRTTFRQTAAFRPVRCFSTTPRVMTEGATGSVRPTGGSGDAFQRREKA
SEDYAIRQREKEKLIELKKKLQEQQQHLDRLSKHIDEITREQGGEKN

The coding sequence for the mature FvAFP1 polypeptide has the nucleotide sequence set forth in SEQ ID NO: 3. The amino acid sequence of the mature polypeptide is set forth in SEQ ID NO: 4.

For the CGR fraction, additional HPLC fractionations were performed to bulk up the antifungal fraction. This bulked up antifungal fraction was further purified using μ-bore HPLC with a Zorbax 300SB C8 1.0 mm×150 mm column (Agilent Technologies). Starting conditions were 14% acetonitrile, 0.08% formic acid, 0.02% trifluoroacetic acid (TFA), 50 μL/minute. Four minutes following sample injection, a 50 minute linear gradient was started to 33% acetonitrile, 0.08% formic acid, 0.02% TFA. 214 nm peak based fractions were collected using an Agilent micro-fraction collector, dried in a centrifugal evaporator, and assayed for antifungal activity as described above. A peak eluting at approximately 34 minutes was found to have activity against FGR. ESI mass spectra were obtained on an integrated Agilent MSD TOF mass spectrometer. The mass of the peptide was determined to be 7,907 Da. The complete sequence of the CgrAFP1 was identified with a coding sequence having the nucleotide sequence set forth in SEQ ID NO: 6 and an amino acid sequence set forth in SEQ ID NO: 7 for the full-length polypeptide. The full-length CgrAFP1 polypeptide is provided below with the predicted mature peptide underlined. The predicted mature peptide has a mass of 7906 Da, which matches the mass of the isolated polypeptide.

```
                                        (SEQ ID NO: 7)
MMRIAATKAAARPLSLASRAAFSTTTRAMAEGDTGAPSKYGGGDAFQKRE

KANEDYAIRQREKEKLLELKKKLSEQQAHLQQLSDHIDEITKNQGGEHN
```

The coding sequence for the mature CgrAFP1 polypeptide has the nucleotide sequence set forth in SEQ ID NO: 8. The amino acid sequence of the mature polypeptide is set forth in SEQ ID NO: 9.

Example 2

Antifungal Plate Assay

The antifungal activity of the *F. verticillioides* and *C. graminicola* dried fractionated extracts from HPLC against the fungal pathogen *Fusarium graminearum* (FGR; isolate 73B ISU) are assessed using a standard plate assay.

Preparation of Cultures for Spore Production

FGR cultures are prepared using ½× oatmeal agar. Cultures of FVE can be prepared using V8 agar plates. Media recipes are provided below.

Specifically, tubes containing silica-gel fungal stocks stored at −20° C. are briefly flamed, and approximately 5 crystals are sprinkled onto the agar surface. 2-3 plates of each fungal isolate can be prepared. The newly plated cultures are stored in a plastic box to prevent the cultures from drying out. FVE cultures are grown in the dark at room temperature. FGR cultures are grown in an illuminated growth chamber at 27° C. New cultures are prepared every other week to maintain a consistent supply of spores.

Spore Preparation

Spores are prepared from 2-4 week old cultures of FGR. A portion of the culture plate is rinsed with a small amount of assay medium. The assay medium is then transferred to a sterile tube. Samples are then vortexed, and spores quantified using a hemacytometer.

Spores are diluted to the desired concentration with assay medium (4,000 spores per mL and kept on ice prior to beginning the antifungal activity assay.

Assay Plate Preparation Details

Standard non-tissue culture treated 96 well flat bottom plates or ½ area non-treated plates (Costar) are used in the antifungal plate assays. Assay medium is ¼× potato dextrose broth.

HPLC-fractionated lead samples are assayed by adding media with fungal spores (as above) into assay plates that the HPLC samples is dried into (Savant Speed-vac). The plates are sealed with a gas permeable membrane ("Breathe-Easy", Cat. No. BEM-1, Diversified Biotech, Boston, Mass.), and the assay allowed to develop in the dark at 28° C. for 24 to 48 hours.

After the incubation period, the plates are placed on an inverted microscope, and each well is examined and scored on a scale of 0-4, according to the following parameters: 0=no inhibition of fungal growth when compared to the negative control, 0.5=slight inhibition (overall growth is less than the negative control but growth from individual spores is not distinct), 1=slight inhibition (overall growth is less than the negative control but growth from individual spores is apparent, albeit not quite confluent), 2=moderate inhibition (growth from 1 spore can easily be identified and is significantly less abundant than the negative control; growth from each spore tends to look spherical), 3=strong inhibition (spores have germinated but growth is limited to a few branches of short hyphae), 4=complete inhibition (spores have not germinated. See, for example, Duvick et al. (1992) *J. Biol. Chem.* 267: 18814-18820). A score sheet containing representative examples of each level of antifungal activity is provided in FIG. 1.

Results

Table 2 provides the results of antifungal activity assays with the HPLC fractions of *F. verticillioides* and *C. graminicola*.

TABLE 2

Antifungal activity of *F. verticillioides* and *C. graminicola* HPLC fractions against *F. graminearum.*

| Fraction No. | Time (min) Start | End | Score |
|---|---|---|---|
| *F. verticillioides* | | | |
| 133 | 66 | 66.5 | 3 |
| 134 | 66.5 | 67 | 3.5 |
| 135 | 67 | 67.5 | 3.5 |
| 136 | 67.5 | 68 | 3.5 |
| 137 | 68 | 68.5 | 3 |
| 138 | 68.5 | 69 | 4 |
| 139 | 69 | 69.5 | 4 |
| 140 | 69.5 | 70 | 4 |
| 141 | 70 | 70.5 | 3.5 |
| 142 | 70.5 | 71 | 3 |
| 143 | 71 | 71.5 | 2.5 |
| 144 | 71.5 | 72 | 2 |
| 145 | 72 | 72.5 | 1.5 |
| 146 | 72.5 | 73 | 3.5 |
| 147 | 73 | 73.5 | 3.5 |
| 148 | 73.5 | 74 | 2.5 |
| 149 | 74 | 74.5 | 2 |
| 150 | 74.5 | 75 | 1.5 |
| 151 | 75 | 75.5 | 1.5 |
| 152 | 75.5 | 76 | 1 |
| 153 | 76 | 76.5 | 0.5 |
| 154 | 76.5 | 77 | 0.5 |
| 155 | 77 | 77.5 | 0.5 |
| *C. graminicola* | | | |
| 81 | 40 | 40.5 | 3 |
| 82 | 40.5 | 41 | 3 |
| 83 | 41 | 41.5 | 3 |
| 84 | 41.5 | 42 | 3.5 |
| 85 | 42 | 42.5 | 3 |
| 86 | 42.5 | 43 | 3 |
| 87 | 43 | 43.5 | 2.5 |
| 88 | 43.5 | 44 | 2.5 |

Media Recipes

1× Potato Dextrose Broth:

For each liter, suspend 24 grams Difco Potato Dextrose Broth (#0549-17-9) in $dH_2O$ and raise final volume to 1 liter and autoclave at 121° C. for 20 minutes. The media is filter sterilized to remove any remaining debris.

Oatmeal Agar:

For each liter, suspend 36.24 grams of Difco Oatmeal Agar (#0552-17-3) and 4.25 grams agar in $dH_2O$ in a 4 liter vessel, cover and autoclave at 121° C. for 20 minutes. Pour plates in sterile hood.

Example 3

Transformation and Regeneration of Transgenic Maize Plants

Immature maize embryos from greenhouse donor plants are bombarded with a plasmid containing a nucleotide sequence encoding the antipathogenic polypeptide set forth in SEQ ID NO: 2, 4, 7, or 9 operably linked to a promoter that drives expression in a maize plant cell and a selectable marker (e.g., the selectable marker gene PAT (Wohlleben et al. (1988) *Gene* 70:25-37), which confers resistance to the herbicide Bialaphos). Alternatively, the selectable marker gene is provided on a separate plasmid.

Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising a nucleotide sequence encoding the antipathogenic polypeptide set forth in SEQ ID NO: 2, 4, 7, or 9 operably linked to a promoter that drives expression in a maize cell is made. This plasmid DNA plus plasmid DNA containing a selectable marker (e.g., PAT) is precipitated onto 1.1 μm (average diameter) tungsten pellets using a $CaCl_2$ precipitation procedure as follows:

100 μL prepared tungsten particles in water
10 μL (1 μg) DNA in Tris EDTA buffer (1 μg total DNA)
100 μL 2.5 M $CaCl_2$
10 μL 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 mL 100% ethanol, and centrifuged for 30 seconds. Again the liquid is removed, and 105 μL 100% ethanol is added to the final tungsten particle pellet. For particle gun bombardment, the tungsten/DNA particles are briefly sonicated and 10 μL spotted onto the center of each macrocarrier and allowed to dry about 2 minutes before bombardment.

Particle Gun Treatment

The sample plates are bombarded at level #4 in a particle gun. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/L Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for fungal resistance.

Bombardment and Culture Media

Bombardment medium (560Y) comprises 4.0 g/L N6 basal salts (SIGMA C-1416), 1.0 mL/L Eriksson's Vitamin Mix (1000× SIGMA-1511), 0.5 mg/L thiamine HCl, 120.0 g/L sucrose, 1.0 mg/L 2,4-D, and 2.88 g/L L-proline (brought to volume with D-I $H_2O$ following adjustment to pH 5.8 with KOH); 2.0 g/L Gelrite (added after bringing to volume with D-I $H_2O$); and 8.5 mg/L silver nitrate (added after sterilizing the medium and cooling to room temperature). Selection medium (560R) comprises 4.0 g/L N6 basal salts (SIGMA C-1416), 1.0 mL/L Eriksson's Vitamin Mix (1000× SIGMA-1511), 0.5 mg/L thiamine HCl, 30.0 g/L sucrose, and 2.0 mg/L 2,4-D (brought to volume with D-I $H_2O$ following adjustment to pH 5.8 with KOH); 3.0 g/L Gelrite (added after bringing to volume with D-I $H_2O$); and 0.85 mg/L silver nitrate and 3.0 mg/L bialaphos (both added after sterilizing the medium and cooling to room temperature).

Plant regeneration medium (288J) comprises 4.3 g/L MS salts (GIBCO 11117-074), 5.0 mL/L MS vitamins stock solution (0.100 g nicotinic acid, 0.02 g/L thiamine HCL, 0.10 g/L pyridoxine HCL, and 0.40 g/L glycine brought to volume with polished D-I $H_2O$) (Murashige and Skoog (1962) *Physiol. Plant.* 15:473), 100 mg/L myo-inositol, 0.5 mg/L zeatin, 60 g/L sucrose, and 1.0 mL/L of 0.1 mM abscisic acid (brought to volume with polished D-I $H_2O$ after adjusting to pH 5.6); 3.0 g/L Gelrite (added after bringing to volume with D-I $H_2O$); and 1.0 mg/L indoleacetic acid and 3.0 mg/L bialaphos (added after sterilizing the medium and cooling to 60° C.). Hormone-free medium (272V) comprises 4.3 g/L MS salts (GIBCO 11117-074), 5.0 mL/L MS vitamins stock solution (0.100 g/L nicotinic acid, 0.02 g/L thiamine HCL, 0.10 g/L pyridoxine HCL, and 0.40 g/L glycine brought to volume with polished D-I $H_2O$), 0.1 g/L myo-inositol, and 40.0 g/L sucrose (brought to volume with polished D-I $H_2O$ after adjusting pH to 5.6); and 6 g/L bacto-agar (added after bringing to volume with polished D-I $H_2O$), sterilized and cooled to 60° C.

Example 4

*Agrobacterium*-Mediated Transformation of Maize and Regeneration of Transgenic Plants For *Agrobacterium*-mediated transformation of maize with a nucleotide sequence encoding the polypeptide of SEQ ID NO: 2, 4, 7, or 9, the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the polynucleotide construct to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is performed. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

Example 5

Transformation of Soybean Embryos

Culture Conditions

Soybean embryogenic suspension cultures (cv. Jack) are maintained in 35 ml liquid medium SB196 (see recipes below) on rotary shaker, 150 rpm, 26° C. with cool white fluorescent lights on 16:8 hr day/night photoperiod at light intensity of 60-85 μE/m2/s. Cultures are subcultured every 7 days to two weeks by inoculating approximately 35 mg of tissue into 35 ml of fresh liquid SB 196 (the preferred subculture interval is every 7 days).

Soybean embryogenic suspension cultures are transformed with the plasmids and DNA fragments described in the following examples by the method of particle gun bombardment (Klein et al. (1987) *Nature,* 327:70).

Soybean Embryogenic Suspension Culture Initiation

Soybean cultures are initiated twice each month with 5-7 days between each initiation.

Pods with immature seeds from available soybean plants 45-55 days after planting are picked, removed from their shells and placed into a sterilized magenta box. The soybean seeds are sterilized by shaking them for 15 minutes in a 5% Clorox solution with 1 drop of ivory soap (95 ml of autoclaved distilled water plus 5 ml Clorox and 1 drop of soap). Mix well. Seeds are rinsed using 2 1-liter bottles of sterile distilled water and those less than 4 mm are placed on individual microscope slides. The small end of the seed is cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB 196 liquid media for 7 days.

Preparation of DNA for Bombardment

Either an intact plasmid or a DNA plasmid fragment containing the genes of interest and the selectable marker gene are used for bombardment. Plasmid DNA for bombardment are routinely prepared and purified using the method described in the Promega™ Protocols and Applications Guide, Second Edition (page 106). Fragments of the plasmids carrying the antifungal protein coding sequence are obtained by gel isolation of double digested plasmids. In each case, 100 ug of plasmid DNA is digested in 0.5 ml of the specific enzyme mix that is appropriate for the plasmid of interest. The resulting DNA fragments are separated by gel electrophoresis on 1% SeaPlaque GTG agarose (BioWhitaker Molecular Applications) and the DNA fragments containing the antifungal protein coding sequence are cut from the agarose gel. DNA is purified from the agarose using the GELase digesting enzyme following the manufacturer's protocol.

A 50 μl aliquot of sterile distilled water containing 3 mg of gold particles (3 mg gold) is added to 5 μl of a 1 μg/μl DNA solution (either intact plasmid or DNA fragment prepared as described above), 50 μl 12.5M $CaCl_2$ and 20 μl of 0.1 M spermidine. The mixture is shaken 3 min on level 3 of a vortex shaker and spun for 10 sec in a bench microfuge. After a wash with 400 μl 100% ethanol the pellet is suspended by sonication in 40 μl of 100% ethanol. Five μl of DNA suspension is dispensed to each flying disk of the Biolistic PDS 1000/HE instrument disk. Each 5 μl aliquot contains approximately 0.375 mg gold per bombardment (i.e. per disk).

Tissue Preparation and Bombardment with DNA

Approximately 150-200 mg of 7 day old embryonic suspension cultures are placed in an empty, sterile 60×15 mm petri dish and the dish covered with plastic mesh. Tissue is bombarded 1 or 2 shots per plate with membrane rupture pressure set at 1100 PSI and the chamber evacuated to a vacuum of 27-28 inches of mercury. Tissue is placed approximately 3.5 inches from the retaining/stopping screen.

Selection of Transformed Embryos

Transformed embryos were selected either using hygromycin (when the hygromycin phosphotransferase, HPT, gene was used as the selectable marker) or chlorsulfuron (when the acetolactate synthase, ALS, gene was used as the selectable marker).

Hygromycin (HPT) Selection

Following bombardment, the tissue is placed into fresh SB196 media and cultured as described above. Six days post-bombardment, the SB 196 is exchanged with fresh SB 196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.

Chlorsulfuron (ALS) Selection

Following bombardment, the tissue is divided between 2 flasks with fresh SB196 media and cultured as described above. Six to seven days post-bombardment, the SB196 is exchanged with fresh SB196 containing selection agent of 100 ng/ml Chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB 196 to generate new, clonally propagated, transformed embryogenic suspension cultures.

Regeneration of Soybean Somatic Embryos into Plants

In order to obtain whole plants from embryogenic suspension cultures, the tissue must be regenerated.

Embryo Maturation

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 uE/m2s. After this time embryo clusters are removed to a solid agar media, SB166, for 1-2 weeks. Clusters are then subcultured to medium SB103 for 3 weeks. During this period, individual embryos can be removed from the clusters and screened for fungal resistance.

Embryo Desiccation and Germination

Matured individual embryos are desiccated by placing them into an empty, small petri dish (35×10 mm) for approximately 4-7 days. The plates are sealed with fiber tape (creating a small humidity chamber). Desiccated embryos are planted into SB71-4 medium where they were left to germinate under the same culture conditions described above. Germinated plantlets are removed from germination medium and rinsed thoroughly with water and then planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot. After 10 to 16 weeks, mature seeds are harvested, chipped and analyzed for proteins.

Media Recipes

| SB 196 - FN Lite liquid proliferation medium (per liter) - | |
|---|---|
| MS FeEDTA - 100x Stock 1 | 10 ml |
| MS Sulfate - 100x Stock 2 | 10 ml |
| FN Lite Halides - 100x Stock 3 | 10 ml |
| FN Lite P, B, Mo - 100x Stock 4 | 10 ml |
| B5 vitamins (1 ml/L) | 1.0 ml |
| 2,4-D (10 mg/L final concentration) | 1.0 ml |
| KNO3 | 2.83 gm |
| (NH4)2SO4 | 0.463 gm |
| Asparagine | 1.0 gm |
| Sucrose (1%) | 10 gm |
| pH 5.8 | |

FN Lite Stock Solutions

| Stock # | | 1000 ml | 500 ml |
|---|---|---|---|
| 1 | MS Fe EDTA 100x Stock | | |
| | $Na_2$ EDTA* | 3.724 g | 1.862 g |
| | $FeSO_4$—$7H_2O$ | 2.784 g | 1.392 g |
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

*Add first, dissolve in dark bottle while stirring

SB1 solid medium (per liter) comprises: 1 pkg. MS salts (Gibco/BRL—Cat #11117-066); 1 ml B5 vitamins 1000× stock; 31.5 g sucrose; 2 ml 2,4-D (20 mg/L final concentration); pH 5.7; and, 8 g TC agar.

SB 166 solid medium (per liter) comprises: 1 pkg. MS salts (Gibco/BRL—Cat #11117-066); 1 ml B5 vitamins 1000× stock; 60 g maltose; 750 mg MgCl2 hexahydrate; 5 g activated charcoal; pH 5.7; and, 2 g gelrite.

SB 103 solid medium (per liter) comprises: 1 pkg. MS salts (Gibco/BRL—Cat #11117-066); 1 ml B5 vitamins 1000× stock; 60 g maltose; 750 mg MgC12 hexahydrate; pH 5.7; and, 2 g gelrite.

SB 71-4 solid medium (per liter) comprises: 1 bottle Gamborg's B5 salts w/sucrose (Gibco/BRL—Cat #21153-036); pH 5.7; and, 5 g TC agar.

2,4-D stock is obtained premade from Phytotech cat #D 295—concentration is 1 mg/ml.

B5 Vitamins Stock (per 100 ml) which is stored in aliquots at −20 C comprises: 10 g myo-inositol; 100 mg nicotinic acid; 100 mg pyridoxine HCl; and, 1 g thiamine. If the solution does not dissolve quickly enough, apply a low level of heat via the hot stir plate. Chlorsulfuron Stock comprises 1 mg/ml in 0.01 N Ammonium Hydroxide All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the foregoing list of embodiments and appended claims. Although specific terms are employed herein, they are used in a generic and descriptive sense only and not for purposes of limitation.

That which is claimed:

1. An expression cassette comprising a polynucleotide comprising a nucleotide sequence selected from the group consisting of:

(a) the nucleotide sequence set forth in SEQ ID NO:6 or 8;

(b) a nucleotide sequence encoding an amino acid sequence comprising SEQ ID NO:7 or 9;

(c) a nucleotide sequence encoding an amino acid sequence having at least 95% sequence identity to SEQ IF NO:7 or 9, wherein the sequence identity is determined over the full length of the sequence, and wherein said polynucleotide encodes a polypeptide having antifungal activity;

wherein the polynucleotide is operably linked to a heterologous promoter sequence.

2. A host cell comprising the expression cassette of claim 1.

3. A microorganism comprising the expression cassette of claim 2.

4. A method of enhancing plant pathogen resistance in a plant, said method comprising transforming the plant with the expression cassette of claim 1, wherein the polynucleotide encodes a polypeptide selected from the group consisting of:

(a) a polypeptide comprising the amino acid sequence set forth in SEQ ID NO: 7 or 9; and (b) a polypeptide comprising an amino acid sequence having at least 95% sequence identity to SEQ ID NO: 7 or 9, wherein the sequence identity is determined over the full length of the sequence, and wherein said polypeptide has antifungal activity.

5. The method of claim 4, wherein said antifungal activity is against *Fusarium graminearum.*

6. The method of claim 4, wherein said polynucleotide is stably integrated into the genome of the plant.

7. A plant comprising a heterologous polynucleotide operably linked to a promoter that drives expression in the plant, wherein said heterologous polynucleotide comprises a nucleotide sequence selected from the group consisting of:

(a) the nucleotide sequence set forth in SEQ ID NO: 6 or 8;

(b) a nucleotide sequence encoding the amino acid sequence comprising SEQ ID NO: 7 or 9; and (c) a nucleotide sequence encoding an amino acid sequence having at least 95% sequence identity to SEQ ID NO: 7, or 9, wherein the sequence identity is determined over the full length of the sequence, and wherein said polynucleotide encodes a polypeptide having antifungal activity.

8. The plant of claim 7, wherein said plant displays increased resistance to a plant fungal pathogen.

9. The plant of claim 8, wherein said fungus is *Fusarium graminearum.*

10. A transformed seed of the plant of claim 7, wherein the seed comprises the heterologous polynucleotide.

* * * * *

SEQUENCE LISTING

```
<160> NUMBER OF SEQ ID NOS: 117

<210> SEQ ID NO 1
<211> LENGTH: 291
<212> TYPE: DNA
<213> ORGANISM: Fusarium verticillioides
<220> FEATURE:
<221> NAME/KEY: misc_feature
<222> LOCATION: (1)...(291)
<223> OTHER INFORMATION: FvAFP1 (Fusarium verticillioides) full-length
      cds

<400> SEQUENCE: 1

atgcttcgca caaccttccg ccagacagcc gccttccggc ctgttcgatg cttctctacc      60

acacctcgcg tcatgactga gggagctact ggctcagtcc gtcccactgg tggttccggt     120

gatgccttcc agcgacggga gaaggctagc gaggattacg ctatccgcca gcgcgagaag     180

gagaagctga tcgagctgaa gaagaagctc caggagcagc agcagcacct tgaccggctc     240

tccaagcaca tcgacgagat cacccgtgag cagggcggcg agaagaacta a              291


<210> SEQ ID NO 2
<211> LENGTH: 96
<212> TYPE: PRT
<213> ORGANISM: Fusarium verticillioides
```

```
<400> SEQUENCE: 2

Met Leu Arg Thr Thr Phe Arg Gln Thr Ala Ala Phe Arg Pro Val Arg
 1               5                  10                  15

Cys Phe Ser Thr Thr Pro Arg Val Met Thr Glu Gly Ala Thr Gly Ser
            20                  25                  30

Val Arg Pro Thr Gly Gly Ser Gly Asp Ala Phe Gln Arg Arg Glu Lys
        35                  40                  45

Ala Ser Glu Asp Tyr Ala Ile Arg Gln Arg Glu Lys Glu Lys Leu Ile
    50                  55                  60

Glu Leu Lys Lys Lys Leu Gln Glu Gln Gln Gln His Leu Asp Arg Leu
65                  70                  75                  80

Ser Lys His Ile Asp Glu Ile Thr Arg Glu Gln Gly Gly Glu Lys Asn
                85                  90                  95


<210> SEQ ID NO 3
<211> LENGTH: 216
<212> TYPE: DNA
<213> ORGANISM: Fusarium verticillioides
<220> FEATURE:
<221> NAME/KEY: misc_feature
<222> LOCATION: (1)...(216)
<223> OTHER INFORMATION: FvAFP1 mature cds
<220> FEATURE:
<221> NAME/KEY: CDS
<222> LOCATION: (1)...(216)
<223> OTHER INFORMATION: FvAFP1 mature pp

<400> SEQUENCE: 3

act gag gga gct act ggc tca gtc cgt ccc act ggt ggt tcc ggt gat       48
Thr Glu Gly Ala Thr Gly Ser Val Arg Pro Thr Gly Gly Ser Gly Asp
 1               5                  10                  15

gcc ttc cag cga cgg gag aag gct agc gag gat tac gct atc cgc cag       96
Ala Phe Gln Arg Arg Glu Lys Ala Ser Glu Asp Tyr Ala Ile Arg Gln
             20                  25                  30

cgc gag aag gag aag ctg atc gag ctg aag aag aag ctc cag gag cag      144
Arg Glu Lys Glu Lys Leu Ile Glu Leu Lys Lys Lys Leu Gln Glu Gln
         35                  40                  45

cag cag cac ctt gac cgg ctc tcc aag cac atc gac gag atc acc cgt      192
Gln Gln His Leu Asp Arg Leu Ser Lys His Ile Asp Glu Ile Thr Arg
     50                  55                  60

gag cag ggc ggc gag aag aac taa                                      216
Glu Gln Gly Gly Glu Lys Asn
 65                  70


<210> SEQ ID NO 4
<211> LENGTH: 71
<212> TYPE: PRT
<213> ORGANISM: Fusarium verticillioides

<400> SEQUENCE: 4

Thr Glu Gly Ala Thr Gly Ser Val Arg Pro Thr Gly Gly Ser Gly Asp
 1               5                  10                  15

Ala Phe Gln Arg Arg Glu Lys Ala Ser Glu Asp Tyr Ala Ile Arg Gln
            20                  25                  30

Arg Glu Lys Glu Lys Leu Ile Glu Leu Lys Lys Lys Leu Gln Glu Gln
        35                  40                  45

Gln Gln His Leu Asp Arg Leu Ser Lys His Ile Asp Glu Ile Thr Arg
    50                  55                  60

Glu Gln Gly Gly Glu Lys Asn
65                  70
```

<210> SEQ ID NO 5
<211> LENGTH: 30
<212> TYPE: PRT
<213> ORGANISM: Fusarium verticillioides
<220> FEATURE:
<221> NAME/KEY: VARIANT
<222> LOCATION: 26
<223> OTHER INFORMATION: Xaa = Any Amino Acid

<400> SEQUENCE: 5

```
Thr Glu Gly Ala Thr Gly Ser Val Arg Pro Thr Gly Gly Ser Gly Asp
 1               5                  10                  15

Ala Phe Gln Arg Arg Glu Lys Ala Ser Xaa Asp Tyr Ala Ile
            20                  25                  30
```

<210> SEQ ID NO 6
<211> LENGTH: 299
<212> TYPE: DNA
<213> ORGANISM: Colletotrichum graminicola
<220> FEATURE:
<221> NAME/KEY: misc_feature
<222> LOCATION: (1)...(299)
<223> OTHER INFORMATION: CgrAFP1 full-length cds
<220> FEATURE:
<221> NAME/KEY: CDS
<222> LOCATION: (1)...(299)
<223> OTHER INFORMATION: CgrAFP1 full-length pp

<400> SEQUENCE: 6

```
atg atg cgt atc gct gcc acc aag gct gcc gct cgc cct ctg tct ctc       48
Met Met Arg Ile Ala Ala Thr Lys Ala Ala Ala Arg Pro Leu Ser Leu
 1               5                  10                  15

gcc tcc aga gct gcc ttc agc act acc act cgc gcc atg gcc gag ggc       96
Ala Ser Arg Ala Ala Phe Ser Thr Thr Thr Arg Ala Met Ala Glu Gly
             20                  25                  30

gac act gga gct ccc tcc aag tac gga ggc gga gac gct ttc cag aag      144
Asp Thr Gly Ala Pro Ser Lys Tyr Gly Gly Gly Asp Ala Phe Gln Lys
         35                  40                  45

cgc gag aag gcg aac gag gat tac gcc atc cgc cag cgt gag aag gag      192
Arg Glu Lys Ala Asn Glu Asp Tyr Ala Ile Arg Gln Arg Glu Lys Glu
     50                  55                  60

aag ctt ctc gag ctc aag aag aag ctc tcc gag cag cag gcc cac ctc      240
Lys Leu Leu Glu Leu Lys Lys Lys Leu Ser Glu Gln Gln Ala His Leu
 65                  70                  75                  80

cag cag ctg tcc gac cac atc gac gaa atc acc aag aac cag ggc ggc      288
Gln Gln Leu Ser Asp His Ile Asp Glu Ile Thr Lys Asn Gln Gly Gly
                 85                  90                  95

gag cac aac ta                                                       299
Glu His Asn
```

<210> SEQ ID NO 7
<211> LENGTH: 99
<212> TYPE: PRT
<213> ORGANISM: Colletotrichum graminicola

<400> SEQUENCE: 7

```
Met Met Arg Ile Ala Ala Thr Lys Ala Ala Ala Arg Pro Leu Ser Leu
 1               5                  10                  15

Ala Ser Arg Ala Ala Phe Ser Thr Thr Thr Arg Ala Met Ala Glu Gly
            20                  25                  30

Asp Thr Gly Ala Pro Ser Lys Tyr Gly Gly Gly Asp Ala Phe Gln Lys
        35                  40                  45
```

```
Arg Glu Lys Ala Asn Glu Asp Tyr Ala Ile Arg Gln Arg Glu Lys Glu
    50                  55                  60

Lys Leu Leu Glu Leu Lys Lys Lys Leu Ser Glu Gln Gln Ala His Leu
65                  70                  75                  80

Gln Gln Leu Ser Asp His Ile Asp Glu Ile Thr Lys Asn Gln Gly Gly
                85                  90                  95

Glu His Asn


<210> SEQ ID NO 8
<211> LENGTH: 212
<212> TYPE: DNA
<213> ORGANISM: Colletotrichum graminicola
<220> FEATURE:
<221> NAME/KEY: misc_feature
<222> LOCATION: (1)...(212)
<223> OTHER INFORMATION: CgrAFP1 mature cds
<220> FEATURE:
<221> NAME/KEY: CDS
<222> LOCATION: (1)...(212)
<223> OTHER INFORMATION: CgrAFP1 mature pp

<400> SEQUENCE: 8

gcc gag ggc gac act gga gct ccc tcc aag tac gga ggc gga gac gct       48
Ala Glu Gly Asp Thr Gly Ala Pro Ser Lys Tyr Gly Gly Gly Asp Ala
 1               5                  10                  15

ttc cag aag cgc gag aag gcg aac gag gat tac gcc atc cgc cag cgt       96
Phe Gln Lys Arg Glu Lys Ala Asn Glu Asp Tyr Ala Ile Arg Gln Arg
             20                  25                  30

gag aag gag aag ctt ctc gag ctc aag aag aag ctc tcc gag cag cag      144
Glu Lys Glu Lys Leu Leu Glu Leu Lys Lys Lys Leu Ser Glu Gln Gln
         35                  40                  45

gcc cac ctc cag cag ctg tcc gac cac atc gac gaa atc acc aag aac      192
Ala His Leu Gln Gln Leu Ser Asp His Ile Asp Glu Ile Thr Lys Asn
     50                  55                  60

cag ggc ggc gag cac aac ta                                           212
Gln Gly Gly Glu His Asn
 65                  70


<210> SEQ ID NO 9
<211> LENGTH: 70
<212> TYPE: PRT
<213> ORGANISM: Colletotrichum graminicola

<400> SEQUENCE: 9

Ala Glu Gly Asp Thr Gly Ala Pro Ser Lys Tyr Gly Gly Gly Asp Ala
 1               5                  10                  15

Phe Gln Lys Arg Glu Lys Ala Asn Glu Asp Tyr Ala Ile Arg Gln Arg
            20                  25                  30

Glu Lys Glu Lys Leu Leu Glu Leu Lys Lys Lys Leu Ser Glu Gln Gln
        35                  40                  45

Ala His Leu Gln Gln Leu Ser Asp His Ile Asp Glu Ile Thr Lys Asn
    50                  55                  60

Gln Gly Gly Glu His Asn
65                  70


<210> SEQ ID NO 10
<211> LENGTH: 306
<212> TYPE: DNA
<213> ORGANISM: Ajellomyces capsulatus
<220> FEATURE:
<221> NAME/KEY: misc_feature
<222> LOCATION: (1)...(306)
<223> OTHER INFORMATION: AcAFP1 full-length cds
```

-continued

<220> FEATURE:
<221> NAME/KEY: CDS
<222> LOCATION: (1)...(306)
<223> OTHER INFORMATION: AcAFP1 full-length pp

<400> SEQUENCE: 10 atg ctg cgt caa act gcc agg cct ctt ctc cgc gcg agc cag cca cgc 48
Met Leu Arg Gln Thr Ala Arg Pro Leu Leu Arg Ala Ser Gln Pro Arg
1 5 10 15 ctc aat cga ttg ttc tcc gtt gct gcc gca aga atg ggt gaa ggt gat 96
Leu Asn Arg Leu Phe Ser Val Ala Ala Ala Arg Met Gly Glu Gly Asp
20 25 30 gtt ggc gct ccc aag tct acc ggg aaa ttg tcc act acc aat tca tgg 144
Val Gly Ala Pro Lys Ser Thr Gly Lys Leu Ser Thr Thr Asn Ser Trp
35 40 45 agc aag aag gaa gct gcc gat gaa gcc atg tat atc aag caa cgg gag 192
Ser Lys Lys Glu Ala Ala Asp Glu Ala Met Tyr Ile Lys Gln Arg Glu
50 55 60 atg gaa aag ttg cgt act ttg aga gaa aag ctg aaa caa cag cgc cag 240
Met Glu Lys Leu Arg Thr Leu Arg Glu Lys Leu Lys Gln Gln Arg Gln
65 70 75 80 cat ctc gat gaa ctt gat gct cat att gaa caa ctc acc aga gaa cac 288
His Leu Asp Glu Leu Asp Ala His Ile Glu Gln Leu Thr Arg Glu His
85 90 95 ggt ggc gaa cag aac taa 306
Gly Gly Glu Gln Asn
100

<210> SEQ ID NO 11
<211> LENGTH: 101
<212> TYPE: PRT
<213> ORGANISM: Ajellomyces capsulatus

<400> SEQUENCE: 11

Met Leu Arg Gln Thr Ala Arg Pro Leu Leu Arg Ala Ser Gln Pro Arg
1 5 10 15

Leu Asn Arg Leu Phe Ser Val Ala Ala Ala Arg Met Gly Glu Gly Asp
20 25 30

Val Gly Ala Pro Lys Ser Thr Gly Lys Leu Ser Thr Thr Asn Ser Trp
35 40 45

Ser Lys Lys Glu Ala Ala Asp Glu Ala Met Tyr Ile Lys Gln Arg Glu
50 55 60

Met Glu Lys Leu Arg Thr Leu Arg Glu Lys Leu Lys Gln Gln Arg Gln
65 70 75 80

His Leu Asp Glu Leu Asp Ala His Ile Glu Gln Leu Thr Arg Glu His
85 90 95

Gly Gly Glu Gln Asn
100

<210> SEQ ID NO 12
<211> LENGTH: 222
<212> TYPE: DNA
<213> ORGANISM: Ajellomyces capsulatus
<220> FEATURE:
<221> NAME/KEY: misc_feature
<222> LOCATION: (1)...(222)
<223> OTHER INFORMATION: AcAFP1 mature cds
<220> FEATURE:
<221> NAME/KEY: CDS
<222> LOCATION: (1)...(222)
<223> OTHER INFORMATION: AcAFP1 mature pp

<400> SEQUENCE: 12

-continued

```
ggt gaa ggt gat gtt ggc gct ccc aag tct acc ggg aaa ttg tcc act       48
Gly Glu Gly Asp Val Gly Ala Pro Lys Ser Thr Gly Lys Leu Ser Thr
 1               5                  10                  15

acc aat tca tgg agc aag aag gaa gct gcc gat gaa gcc atg tat atc       96
Thr Asn Ser Trp Ser Lys Lys Glu Ala Ala Asp Glu Ala Met Tyr Ile
            20                  25                  30

aag caa cgg gag atg gaa aag ttg cgt act ttg aga gaa aag ctg aaa      144
Lys Gln Arg Glu Met Glu Lys Leu Arg Thr Leu Arg Glu Lys Leu Lys
        35                  40                  45

caa cag cgc cag cat ctc gat gaa ctt gat gct cat att gaa caa ctc      192
Gln Gln Arg Gln His Leu Asp Glu Leu Asp Ala His Ile Glu Gln Leu
    50                  55                  60

acc aga gaa cac ggt ggc gaa cag aac taa                              222
Thr Arg Glu His Gly Gly Glu Gln Asn
 65                  70


<210> SEQ ID NO 13
<211> LENGTH: 73
<212> TYPE: PRT
<213> ORGANISM: Ajellomyces capsulatus

<400> SEQUENCE: 13

Gly Glu Gly Asp Val Gly Ala Pro Lys Ser Thr Gly Lys Leu Ser Thr
 1               5                  10                  15

Thr Asn Ser Trp Ser Lys Lys Glu Ala Ala Asp Glu Ala Met Tyr Ile
            20                  25                  30

Lys Gln Arg Glu Met Glu Lys Leu Arg Thr Leu Arg Glu Lys Leu Lys
        35                  40                  45

Gln Gln Arg Gln His Leu Asp Glu Leu Asp Ala His Ile Glu Gln Leu
    50                  55                  60

Thr Arg Glu His Gly Gly Glu Gln Asn
65                  70


<210> SEQ ID NO 14
<211> LENGTH: 300
<212> TYPE: DNA
<213> ORGANISM: Aspergillus clavatus
<220> FEATURE:
<221> NAME/KEY: misc_feature
<222> LOCATION: (1)...(300)
<223> OTHER INFORMATION: AclAFP1 full-length cds
<220> FEATURE:
<221> NAME/KEY: CDS
<222> LOCATION: (1)...(300)
<223> OTHER INFORMATION: AclAFP1 full-length pp

<400> SEQUENCE: 14

atg ttc cgc cag tcc gtc acc cgc cct ctc gca tcg gcc aac agc gcc       48
Met Phe Arg Gln Ser Val Thr Arg Pro Leu Ala Ser Ala Asn Ser Ala
 1               5                  10                  15

atc gtc aac cgc tcg ttc tct gcc ctg gcc ccc aga atg ggt gct ggc       96
Ile Val Asn Arg Ser Phe Ser Ala Leu Ala Pro Arg Met Gly Ala Gly
            20                  25                  30

gat act ggt gct ccc cgc gcc ggc ggc tct cag tca ggt gat tcc ttc      144
Asp Thr Gly Ala Pro Arg Ala Gly Gly Ser Gln Ser Gly Asp Ser Phe
        35                  40                  45

aca cgc cgc gaa gcc gcc cag gag agc ctg tac atc cac gag aag gag      192
Thr Arg Arg Glu Ala Ala Gln Glu Ser Leu Tyr Ile His Glu Lys Glu
    50                  55                  60

aag gag aag ctc gag agc ctc cgc aag aag atc aag gag cag cag gcc      240
Lys Glu Lys Leu Glu Ser Leu Arg Lys Lys Ile Lys Glu Gln Gln Ala
 65                  70                  75                  80
```

```
cat ctc gcc gag ctc gac aag cac ctt gat gat ttc act aag aac cag      288
His Leu Ala Glu Leu Asp Lys His Leu Asp Asp Phe Thr Lys Asn Gln
                85                  90                  95

ggc aag aac taa                                                      300
Gly Lys Asn


<210> SEQ ID NO 15
<211> LENGTH: 99
<212> TYPE: PRT
<213> ORGANISM: Aspergillus clavatus

<400> SEQUENCE: 15

Met Phe Arg Gln Ser Val Thr Arg Pro Leu Ala Ser Ala Asn Ser Ala
 1               5                  10                  15

Ile Val Asn Arg Ser Phe Ser Ala Leu Ala Pro Arg Met Gly Ala Gly
            20                  25                  30

Asp Thr Gly Ala Pro Arg Ala Gly Gly Ser Gln Ser Gly Asp Ser Phe
        35                  40                  45

Thr Arg Arg Glu Ala Ala Gln Glu Ser Leu Tyr Ile His Glu Lys Glu
    50                  55                  60

Lys Glu Lys Leu Glu Ser Leu Arg Lys Lys Ile Lys Glu Gln Gln Ala
65                  70                  75                  80

His Leu Ala Glu Leu Asp Lys His Leu Asp Asp Phe Thr Lys Asn Gln
                85                  90                  95

Gly Lys Asn


<210> SEQ ID NO 16
<211> LENGTH: 213
<212> TYPE: DNA
<213> ORGANISM: Aspergillus clavatus
<220> FEATURE:
<221> NAME/KEY: misc_feature
<222> LOCATION: (1)...(213)
<223> OTHER INFORMATION: AclAFP1 mature cds
<220> FEATURE:
<221> NAME/KEY: CDS
<222> LOCATION: (1)...(213)
<223> OTHER INFORMATION: AclAFP1 mature pp

<400> SEQUENCE: 16

ggt gct ggc gat act ggt gct ccc cgc gcc ggc ggc tct cag tca ggt       48
Gly Ala Gly Asp Thr Gly Ala Pro Arg Ala Gly Gly Ser Gln Ser Gly
 1               5                  10                  15

gat tcc ttc aca cgc cgc gaa gcc gcc cag gag agc ctg tac atc cac       96
Asp Ser Phe Thr Arg Arg Glu Ala Ala Gln Glu Ser Leu Tyr Ile His
            20                  25                  30

gag aag gag aag gag aag ctc gag agc ctc cgc aag aag atc aag gag      144
Glu Lys Glu Lys Glu Lys Leu Glu Ser Leu Arg Lys Lys Ile Lys Glu
        35                  40                  45

cag cag gcc cat ctc gcc gag ctc gac aag cac ctt gat gat ttc act      192
Gln Gln Ala His Leu Ala Glu Leu Asp Lys His Leu Asp Asp Phe Thr
    50                  55                  60

aag aac cag ggc aag aac taa                                          213
Lys Asn Gln Gly Lys Asn
65                  70


<210> SEQ ID NO 17
<211> LENGTH: 70
<212> TYPE: PRT
<213> ORGANISM: Aspergillus clavatus

<400> SEQUENCE: 17
```

```
Gly Ala Gly Asp Thr Gly Ala Pro Arg Ala Gly Gly Ser Gln Ser Gly
 1               5                  10                  15

Asp Ser Phe Thr Arg Arg Glu Ala Ala Gln Glu Ser Leu Tyr Ile His
            20                  25                  30

Glu Lys Glu Lys Glu Lys Leu Glu Ser Leu Arg Lys Lys Ile Lys Glu
        35                  40                  45

Gln Gln Ala His Leu Ala Glu Leu Asp Lys His Leu Asp Asp Phe Thr
    50                  55                  60

Lys Asn Gln Gly Lys Asn
65                  70


<210> SEQ ID NO 18
<211> LENGTH: 309
<212> TYPE: DNA
<213> ORGANISM: Aspergillus niger
<220> FEATURE:
<221> NAME/KEY: misc_feature
<222> LOCATION: (1)...(309)
<223> OTHER INFORMATION: AnAFP1 full-length cds
<220> FEATURE:
<221> NAME/KEY: CDS
<222> LOCATION: (1)...(309)
<223> OTHER INFORMATION: AnAFP1 full-length pp

<400> SEQUENCE: 18

atg ctc cgc caa tcc atc acc aag tcc tct act acc cgc ctc ctc acc       48
Met Leu Arg Gln Ser Ile Thr Lys Ser Ser Thr Thr Arg Leu Leu Thr
 1               5                  10                  15

acc acc act act cgt tcc ttc tct gct ctc gct ccc aga atg ggt gct       96
Thr Thr Thr Thr Arg Ser Phe Ser Ala Leu Ala Pro Arg Met Gly Ala
            20                  25                  30

ggc gat acc ggt gct ccc cgg ccg ggc ggt tct cag cat gct gac tcg      144
Gly Asp Thr Gly Ala Pro Arg Pro Gly Gly Ser Gln His Ala Asp Ser
        35                  40                  45

ttc acc aag cgc gaa gcc gcc cag gag aac ttg tat gtt cgc gag aag      192
Phe Thr Lys Arg Glu Ala Ala Gln Glu Asn Leu Tyr Val Arg Glu Lys
    50                  55                  60

gag atg gag aag ctc cgt gcc ctg aag gcc aag ctc agc gag cag cgc      240
Glu Met Glu Lys Leu Arg Ala Leu Lys Ala Lys Leu Ser Glu Gln Arg
65                  70                  75                  80

aag cac ctt gat gag ctg gat aag cac att gac gag ttc acc aag aac      288
Lys His Leu Asp Glu Leu Asp Lys His Ile Asp Glu Phe Thr Lys Asn
                85                  90                  95

cag ggc ggc gag cag aac tag                                          309
Gln Gly Gly Glu Gln Asn
            100


<210> SEQ ID NO 19
<211> LENGTH: 102
<212> TYPE: PRT
<213> ORGANISM: Aspergillus niger

<400> SEQUENCE: 19

Met Leu Arg Gln Ser Ile Thr Lys Ser Ser Thr Thr Arg Leu Leu Thr
 1               5                  10                  15

Thr Thr Thr Thr Arg Ser Phe Ser Ala Leu Ala Pro Arg Met Gly Ala
            20                  25                  30

Gly Asp Thr Gly Ala Pro Arg Pro Gly Gly Ser Gln His Ala Asp Ser
        35                  40                  45

Phe Thr Lys Arg Glu Ala Ala Gln Glu Asn Leu Tyr Val Arg Glu Lys
    50                  55                  60
```

```
Glu Met Glu Lys Leu Arg Ala Leu Lys Ala Lys Leu Ser Glu Gln Arg
65                  70                  75                  80

Lys His Leu Asp Glu Leu Asp Lys His Ile Asp Glu Phe Thr Lys Asn
                85                  90                  95

Gln Gly Gly Glu Gln Asn
            100


<210> SEQ ID NO 20
<211> LENGTH: 219
<212> TYPE: DNA
<213> ORGANISM: Aspergillus niger
<220> FEATURE:
<221> NAME/KEY: misc_feature
<222> LOCATION: (1)...(219)
<223> OTHER INFORMATION: AnAFP1 mature cds
<220> FEATURE:
<221> NAME/KEY: CDS
<222> LOCATION: (1)...(219)
<223> OTHER INFORMATION: AnAFP1 mature pp

<400> SEQUENCE: 20

ggt gct ggc gat acc ggt gct ccc cgg ccg ggc ggt tct cag cat gct       48
Gly Ala Gly Asp Thr Gly Ala Pro Arg Pro Gly Gly Ser Gln His Ala
 1               5                  10                  15

gac tcg ttc acc aag cgc gaa gcc gcc cag gag aac ttg tat gtt cgc       96
Asp Ser Phe Thr Lys Arg Glu Ala Ala Gln Glu Asn Leu Tyr Val Arg
             20                  25                  30

gag aag gag atg gag aag ctc cgt gcc ctg aag gcc aag ctc agc gag      144
Glu Lys Glu Met Glu Lys Leu Arg Ala Leu Lys Ala Lys Leu Ser Glu
         35                  40                  45

cag cgc aag cac ctt gat gag ctg gat aag cac att gac gag ttc acc      192
Gln Arg Lys His Leu Asp Glu Leu Asp Lys His Ile Asp Glu Phe Thr
     50                  55                  60

aag aac cag ggc ggc gag cag aac tag                                  219
Lys Asn Gln Gly Gly Glu Gln Asn
 65                  70


<210> SEQ ID NO 21
<211> LENGTH: 72
<212> TYPE: PRT
<213> ORGANISM: Aspergillus niger

<400> SEQUENCE: 21

Gly Ala Gly Asp Thr Gly Ala Pro Arg Pro Gly Gly Ser Gln His Ala
 1               5                  10                  15

Asp Ser Phe Thr Lys Arg Glu Ala Ala Gln Glu Asn Leu Tyr Val Arg
            20                  25                  30

Glu Lys Glu Met Glu Lys Leu Arg Ala Leu Lys Ala Lys Leu Ser Glu
        35                  40                  45

Gln Arg Lys His Leu Asp Glu Leu Asp Lys His Ile Asp Glu Phe Thr
    50                  55                  60

Lys Asn Gln Gly Gly Glu Gln Asn
65                  70


<210> SEQ ID NO 22
<211> LENGTH: 303
<212> TYPE: DNA
<213> ORGANISM: Aspergillus oryzae
<220> FEATURE:
<221> NAME/KEY: misc_feature
<222> LOCATION: (1)...(303)
<223> OTHER INFORMATION: AoAFP1 full-length cds
<220> FEATURE:
```

-continued

```
<221> NAME/KEY: CDS
<222> LOCATION: (1)...(303)
<223> OTHER INFORMATION: AoAFP1 full-length pp

<400> SEQUENCE: 22

atg ctc cgt caa tcc atc aga cct ctc act acc gct aac cgc gcc ctc       48
Met Leu Arg Gln Ser Ile Arg Pro Leu Thr Thr Ala Asn Arg Ala Leu
 1               5                  10                  15

gtc tcc cgg tct ttt tca gct ctc gcc ccc aag atg gcc gca ggt gat       96
Val Ser Arg Ser Phe Ser Ala Leu Ala Pro Lys Met Ala Ala Gly Asp
             20                  25                  30

acc ggt gct ccc cgt ccc ggt ggt tcc cag cat gcc gac caa ttc acc      144
Thr Gly Ala Pro Arg Pro Gly Gly Ser Gln His Ala Asp Gln Phe Thr
         35                  40                  45

aag cgc gaa gcc gca cag gag aac ctc tac att cac gag aag gag cgt      192
Lys Arg Glu Ala Ala Gln Glu Asn Leu Tyr Ile His Glu Lys Glu Arg
     50                  55                  60

gag aag ctt ttg gcc ctc cgc aac aag gtc aag gaa cag cgc aag cac      240
Glu Lys Leu Leu Ala Leu Arg Asn Lys Val Lys Glu Gln Arg Lys His
 65                  70                  75                  80

ctc gat gag ctg gac aag cac att gag gag ttg acc aag aac cag ggc      288
Leu Asp Glu Leu Asp Lys His Ile Glu Glu Leu Thr Lys Asn Gln Gly
                 85                  90                  95

ggt gaa cag aac tag                                                  303
Gly Glu Gln Asn
            100


<210> SEQ ID NO 23
<211> LENGTH: 100
<212> TYPE: PRT
<213> ORGANISM: Aspergillus oryzae

<400> SEQUENCE: 23

Met Leu Arg Gln Ser Ile Arg Pro Leu Thr Thr Ala Asn Arg Ala Leu
 1               5                  10                  15

Val Ser Arg Ser Phe Ser Ala Leu Ala Pro Lys Met Ala Ala Gly Asp
            20                  25                  30

Thr Gly Ala Pro Arg Pro Gly Gly Ser Gln His Ala Asp Gln Phe Thr
        35                  40                  45

Lys Arg Glu Ala Ala Gln Glu Asn Leu Tyr Ile His Glu Lys Glu Arg
    50                  55                  60

Glu Lys Leu Leu Ala Leu Arg Asn Lys Val Lys Glu Gln Arg Lys His
65                  70                  75                  80

Leu Asp Glu Leu Asp Lys His Ile Glu Glu Leu Thr Lys Asn Gln Gly
                85                  90                  95

Gly Glu Gln Asn
            100


<210> SEQ ID NO 24
<211> LENGTH: 219
<212> TYPE: DNA
<213> ORGANISM: Aspergillus oryzae
<220> FEATURE:
<221> NAME/KEY: misc_feature
<222> LOCATION: (1)...(219)
<223> OTHER INFORMATION: AoAFP1 mature cds
<220> FEATURE:
<221> NAME/KEY: CDS
<222> LOCATION: (1)...(219)
<223> OTHER INFORMATION: AoAFP1 mature pp

<400> SEQUENCE: 24
```

```
gcc gca ggt gat acc ggt gct ccc cgt ccc ggt ggt tcc cag cat gcc        48
Ala Ala Gly Asp Thr Gly Ala Pro Arg Pro Gly Gly Ser Gln His Ala
 1               5                  10                  15

gac caa ttc acc aag cgc gaa gcc gca cag gag aac ctc tac att cac        96
Asp Gln Phe Thr Lys Arg Glu Ala Ala Gln Glu Asn Leu Tyr Ile His
            20                  25                  30

gag aag gag cgt gag aag ctt ttg gcc ctc cgc aac aag gtc aag gaa       144
Glu Lys Glu Arg Glu Lys Leu Leu Ala Leu Arg Asn Lys Val Lys Glu
        35                  40                  45

cag cgc aag cac ctc gat gag ctg gac aag cac att gag gag ttg acc       192
Gln Arg Lys His Leu Asp Glu Leu Asp Lys His Ile Glu Glu Leu Thr
    50                  55                  60

aag aac cag ggc ggt gaa cag aac tag                                   219
Lys Asn Gln Gly Gly Glu Gln Asn
 65                 70


<210> SEQ ID NO 25
<211> LENGTH: 72
<212> TYPE: PRT
<213> ORGANISM: Aspergillus oryzae

<400> SEQUENCE: 25

Ala Ala Gly Asp Thr Gly Ala Pro Arg Pro Gly Gly Ser Gln His Ala
 1               5                  10                  15

Asp Gln Phe Thr Lys Arg Glu Ala Ala Gln Glu Asn Leu Tyr Ile His
            20                  25                  30

Glu Lys Glu Arg Glu Lys Leu Leu Ala Leu Arg Asn Lys Val Lys Glu
        35                  40                  45

Gln Arg Lys His Leu Asp Glu Leu Asp Lys His Ile Glu Glu Leu Thr
    50                  55                  60

Lys Asn Gln Gly Gly Glu Gln Asn
65                  70


<210> SEQ ID NO 26
<211> LENGTH: 306
<212> TYPE: DNA
<213> ORGANISM: Aspergillus terreus
<220> FEATURE:
<221> NAME/KEY: misc_feature
<222> LOCATION: (1)...(306)
<223> OTHER INFORMATION: AtAFP1 full-length cds
<220> FEATURE:
<221> NAME/KEY: CDS
<222> LOCATION: (1)...(306)
<223> OTHER INFORMATION: AtAFP1 full-length pp

<400> SEQUENCE: 26

atg ctt cgc caa tcc atc atc aga cct ctg tcc acc gcc aac cgc gcc        48
Met Leu Arg Gln Ser Ile Ile Arg Pro Leu Ser Thr Ala Asn Arg Ala
 1               5                  10                  15

gtc gtc tcc cgg tct ttc tct tcc ttc gct cct aga atg tcc gaa ggt        96
Val Val Ser Arg Ser Phe Ser Ser Phe Ala Pro Arg Met Ser Glu Gly
            20                  25                  30

gat act ggt gca ccc cgg tcc ggc ggt tcc gcc cag gga gat gca ttc       144
Asp Thr Gly Ala Pro Arg Ser Gly Gly Ser Ala Gln Gly Asp Ala Phe
        35                  40                  45

acc cgc cgc gaa gcc gcc cag gag aac ctc tac atc cac gaa aag gag       192
Thr Arg Arg Glu Ala Ala Gln Glu Asn Leu Tyr Ile His Glu Lys Glu
    50                  55                  60

atg gag aag ctc gaa gcc ttg aga aag aag gtc aat gag caa cag aaa       240
Met Glu Lys Leu Glu Ala Leu Arg Lys Lys Val Asn Glu Gln Gln Lys
 65                 70                  75                  80
```

-continued

```
cac ctc aac gag ctg gac cag cat ctt aag gat ctc cag aag gag cag      288
His Leu Asn Glu Leu Asp Gln His Leu Lys Asp Leu Gln Lys Glu Gln
                 85                  90                  95

ggc ggc gag aag aac taa                                              306
Gly Gly Glu Lys Asn
            100


<210> SEQ ID NO 27
<211> LENGTH: 101
<212> TYPE: PRT
<213> ORGANISM: Aspergillus terreus

<400> SEQUENCE: 27

Met Leu Arg Gln Ser Ile Ile Arg Pro Leu Ser Thr Ala Asn Arg Ala
 1               5                  10                  15

Val Val Ser Arg Ser Phe Ser Ser Phe Ala Pro Arg Met Ser Glu Gly
            20                  25                  30

Asp Thr Gly Ala Pro Arg Ser Gly Gly Ser Ala Gln Gly Asp Ala Phe
        35                  40                  45

Thr Arg Arg Glu Ala Ala Gln Glu Asn Leu Tyr Ile His Glu Lys Glu
    50                  55                  60

Met Glu Lys Leu Glu Ala Leu Arg Lys Lys Val Asn Glu Gln Gln Lys
65                  70                  75                  80

His Leu Asn Glu Leu Asp Gln His Leu Lys Asp Leu Gln Lys Glu Gln
                85                  90                  95

Gly Gly Glu Lys Asn
            100


<210> SEQ ID NO 28
<211> LENGTH: 219
<212> TYPE: DNA
<213> ORGANISM: Aspergillus terreus
<220> FEATURE:
<221> NAME/KEY: misc_feature
<222> LOCATION: (1)...(219)
<223> OTHER INFORMATION: AtAFP1 mature cds
<220> FEATURE:
<221> NAME/KEY: CDS
<222> LOCATION: (1)...(219)
<223> OTHER INFORMATION: AtAFP1 mature pp

<400> SEQUENCE: 28

tcc gaa ggt gat act ggt gca ccc cgg tcc ggc ggt tcc gcc cag gga       48
Ser Glu Gly Asp Thr Gly Ala Pro Arg Ser Gly Gly Ser Ala Gln Gly
 1               5                   10                  15

gat gca ttc acc cgc cgc gaa gcc gcc cag gag aac ctc tac atc cac       96
Asp Ala Phe Thr Arg Arg Glu Ala Ala Gln Glu Asn Leu Tyr Ile His
             20                  25                  30

gaa aag gag atg gag aag ctc gaa gcc ttg aga aag aag gtc aat gag      144
Glu Lys Glu Met Glu Lys Leu Glu Ala Leu Arg Lys Lys Val Asn Glu
         35                  40                  45

caa cag aaa cac ctc aac gag ctg gac cag cat ctt aag gat ctc cag      192
Gln Gln Lys His Leu Asn Glu Leu Asp Gln His Leu Lys Asp Leu Gln
     50                  55                  60

aag gag cag ggc ggc gag aag aac taa                                  219
Lys Glu Gln Gly Gly Glu Lys Asn
 65                  70


<210> SEQ ID NO 29
<211> LENGTH: 72
<212> TYPE: PRT
<213> ORGANISM: Aspergillus terreus
```

<400> SEQUENCE: 29

```
Ser Glu Gly Asp Thr Gly Ala Pro Arg Ser Gly Gly Ser Ala Gln Gly
 1               5                  10                  15

Asp Ala Phe Thr Arg Arg Glu Ala Ala Gln Glu Asn Leu Tyr Ile His
            20                  25                  30

Glu Lys Glu Met Glu Lys Leu Glu Ala Leu Arg Lys Lys Val Asn Glu
        35                  40                  45

Gln Gln Lys His Leu Asn Glu Leu Asp Gln His Leu Lys Asp Leu Gln
    50                  55                  60

Lys Glu Gln Gly Gly Glu Lys Asn
65                  70
```

<210> SEQ ID NO 30
<211> LENGTH: 306
<212> TYPE: DNA
<213> ORGANISM: Botryotinia fuckeliana
<220> FEATURE:
<221> NAME/KEY: misc_feature
<222> LOCATION: (1)...(306)
<223> OTHER INFORMATION: BfAFP1 full-length cds
<220> FEATURE:
<221> NAME/KEY: CDS
<222> LOCATION: (1)...(306)
<223> OTHER INFORMATION: BfAFP1 full-length pp

<400> SEQUENCE: 30

```
atg tat cgt ctt gca atc aac tct gcc atg cga cca gca gtc cgc gca       48
Met Tyr Arg Leu Ala Ile Asn Ser Ala Met Arg Pro Ala Val Arg Ala
 1               5                  10                  15

tcc gtc cca gct gcc aga gca ttt acc gta tca gca cgc act atg ggc       96
Ser Val Pro Ala Ala Arg Ala Phe Thr Val Ser Ala Arg Thr Met Gly
            20                  25                  30

gag gga gac acc ggc gct gcc aga ttt ggc ggc caa caa gat gcc ttt      144
Glu Gly Asp Thr Gly Ala Ala Arg Phe Gly Gly Gln Gln Asp Ala Phe
        35                  40                  45

acc aaa cgc gaa aag gcc aat gag gat tac acc atc cgc cag cgt gag      192
Thr Lys Arg Glu Lys Ala Asn Glu Asp Tyr Thr Ile Arg Gln Arg Glu
    50                  55                  60

aat gag aag ctc ttg gag ttg agg aag aaa atc acc gaa cag cgt gat      240
Asn Glu Lys Leu Leu Glu Leu Arg Lys Lys Ile Thr Glu Gln Arg Asp
65                  70                  75                  80

cac ttg aag aaa ctc gag gac cac att tcc gaa atc gag aag caa tct      288
His Leu Lys Lys Leu Glu Asp His Ile Ser Glu Ile Glu Lys Gln Ser
                85                  90                  95

ggt ggc gag cag aac taa                                              306
Gly Gly Glu Gln Asn
            100
```

<210> SEQ ID NO 31
<211> LENGTH: 101
<212> TYPE: PRT
<213> ORGANISM: Botryotinia fuckeliana

<400> SEQUENCE: 31

```
Met Tyr Arg Leu Ala Ile Asn Ser Ala Met Arg Pro Ala Val Arg Ala
 1               5                  10                  15

Ser Val Pro Ala Ala Arg Ala Phe Thr Val Ser Ala Arg Thr Met Gly
            20                  25                  30

Glu Gly Asp Thr Gly Ala Ala Arg Phe Gly Gly Gln Gln Asp Ala Phe
        35                  40                  45

Thr Lys Arg Glu Lys Ala Asn Glu Asp Tyr Thr Ile Arg Gln Arg Glu
```

```
    50                  55                  60

Asn Glu Lys Leu Leu Glu Leu Arg Lys Lys Ile Thr Glu Gln Arg Asp
65                  70                  75                  80

His Leu Lys Lys Leu Glu Asp His Ile Ser Glu Ile Glu Lys Gln Ser
                85                  90                  95

Gly Gly Glu Gln Asn
            100


<210> SEQ ID NO 32
<211> LENGTH: 213
<212> TYPE: DNA
<213> ORGANISM: Botryotinia fuckeliana
<220> FEATURE:
<221> NAME/KEY: misc_feature
<222> LOCATION: (1)...(213)
<223> OTHER INFORMATION: BfAFP1 mature cds
<220> FEATURE:
<221> NAME/KEY: CDS
<222> LOCATION: (1)...(213)
<223> OTHER INFORMATION: BfAFP1 mature pp

<400> SEQUENCE: 32

ggc gag gga gac acc ggc gct gcc aga ttt ggc ggc caa caa gat gcc       48
Gly Glu Gly Asp Thr Gly Ala Ala Arg Phe Gly Gly Gln Gln Asp Ala
 1               5                  10                  15

ttt acc aaa cgc gaa aag gcc aat gag gat tac acc atc cgc cag cgt       96
Phe Thr Lys Arg Glu Lys Ala Asn Glu Asp Tyr Thr Ile Arg Gln Arg
            20                  25                  30

gag aat gag aag ctc ttg gag ttg agg aag aaa atc acc gaa cag cgt      144
Glu Asn Glu Lys Leu Leu Glu Leu Arg Lys Lys Ile Thr Glu Gln Arg
        35                  40                  45

gat cac ttg aag aaa ctc gag gac cac att tcc gaa atc gag aag caa      192
Asp His Leu Lys Lys Leu Glu Asp His Ile Ser Glu Ile Glu Lys Gln
    50                  55                  60

tct ggt ggc gag cag aac taa                                          213
Ser Gly Gly Glu Gln Asn
 65                  70


<210> SEQ ID NO 33
<211> LENGTH: 70
<212> TYPE: PRT
<213> ORGANISM: Botryotinia fuckeliana

<400> SEQUENCE: 33

Gly Glu Gly Asp Thr Gly Ala Ala Arg Phe Gly Gly Gln Gln Asp Ala
 1               5                  10                  15

Phe Thr Lys Arg Glu Lys Ala Asn Glu Asp Tyr Thr Ile Arg Gln Arg
            20                  25                  30

Glu Asn Glu Lys Leu Leu Glu Leu Arg Lys Lys Ile Thr Glu Gln Arg
        35                  40                  45

Asp His Leu Lys Lys Leu Glu Asp His Ile Ser Glu Ile Glu Lys Gln
    50                  55                  60

Ser Gly Gly Glu Gln Asn
65                  70


<210> SEQ ID NO 34
<211> LENGTH: 306
<212> TYPE: DNA
<213> ORGANISM: Botrytis cinerea
<220> FEATURE:
<221> NAME/KEY: misc_feature
<222> LOCATION: (1)...(306)
<223> OTHER INFORMATION: BcAFP1 (Botrytis cinerea) full-length cds
```

```
<220> FEATURE:
<221> NAME/KEY: CDS
<222> LOCATION: (1)...(306)
<223> OTHER INFORMATION: BcAFP1 (Botrytis cinerea) full-length pp

<400> SEQUENCE: 34

atg tat cgt ctt gca atc aac tct gcc atg cga cca gca gtc cgc gca       48
Met Tyr Arg Leu Ala Ile Asn Ser Ala Met Arg Pro Ala Val Arg Ala
 1               5                  10                  15

tcc gtc cca gct gcc aga gca ttt acc gta tca gca cgc act atg ggc       96
Ser Val Pro Ala Ala Arg Ala Phe Thr Val Ser Ala Arg Thr Met Gly
            20                  25                  30

gag gga gac acc ggc gct gcc aga ttt ggc ggc caa caa gat gcc ttt      144
Glu Gly Asp Thr Gly Ala Ala Arg Phe Gly Gly Gln Gln Asp Ala Phe
        35                  40                  45

acc aaa cgc gaa aag gcc aat gag gat tac acc atc cgc cag cgt gag      192
Thr Lys Arg Glu Lys Ala Asn Glu Asp Tyr Thr Ile Arg Gln Arg Glu
    50                  55                  60

aat gag aag ctc ttg gag ttg agg aag aaa atc acc gaa cag cgt gat      240
Asn Glu Lys Leu Leu Glu Leu Arg Lys Lys Ile Thr Glu Gln Arg Asp
 65                  70                  75                  80

cac ttg aag aaa ctc gag gac cac att tcc gaa atc gag aag caa tct      288
His Leu Lys Lys Leu Glu Asp His Ile Ser Glu Ile Glu Lys Gln Ser
                 85                  90                  95

ggt ggc gag cag aag taa                                              306
Gly Gly Glu Gln Lys
            100


<210> SEQ ID NO 35
<211> LENGTH: 101
<212> TYPE: PRT
<213> ORGANISM: Botrytis cinerea

<400> SEQUENCE: 35

Met Tyr Arg Leu Ala Ile Asn Ser Ala Met Arg Pro Ala Val Arg Ala
 1               5                  10                  15

Ser Val Pro Ala Ala Arg Ala Phe Thr Val Ser Ala Arg Thr Met Gly
            20                  25                  30

Glu Gly Asp Thr Gly Ala Ala Arg Phe Gly Gly Gln Gln Asp Ala Phe
        35                  40                  45

Thr Lys Arg Glu Lys Ala Asn Glu Asp Tyr Thr Ile Arg Gln Arg Glu
    50                  55                  60

Asn Glu Lys Leu Leu Glu Leu Arg Lys Lys Ile Thr Glu Gln Arg Asp
65                  70                  75                  80

His Leu Lys Lys Leu Glu Asp His Ile Ser Glu Ile Glu Lys Gln Ser
                85                  90                  95

Gly Gly Glu Gln Lys
            100


<210> SEQ ID NO 36
<211> LENGTH: 213
<212> TYPE: DNA
<213> ORGANISM: Botrytis cinerea
<220> FEATURE:
<221> NAME/KEY: misc_feature
<222> LOCATION: (1)...(213)
<223> OTHER INFORMATION: BcAFP1 mature cds
<220> FEATURE:
<221> NAME/KEY: CDS
<222> LOCATION: (1)...(213)
<223> OTHER INFORMATION: BcAFP1 mature pp

<400> SEQUENCE: 36
```

```
ggc gag gga gac acc ggc gct gcc aga ttt ggc ggc caa caa gat gcc        48
Gly Glu Gly Asp Thr Gly Ala Ala Arg Phe Gly Gly Gln Gln Asp Ala
 1               5                  10                  15

ttt acc aaa cgc gaa aag gcc aat gag gat tac acc atc cgc cag cgt        96
Phe Thr Lys Arg Glu Lys Ala Asn Glu Asp Tyr Thr Ile Arg Gln Arg
            20                  25                  30

gag aat gag aag ctc ttg gag ttg agg aag aaa atc acc gaa cag cgt       144
Glu Asn Glu Lys Leu Leu Glu Leu Arg Lys Lys Ile Thr Glu Gln Arg
        35                  40                  45

gat cac ttg aag aaa ctc gag gac cac att tcc gaa atc gag aag caa       192
Asp His Leu Lys Lys Leu Glu Asp His Ile Ser Glu Ile Glu Lys Gln
    50                  55                  60

tct ggt ggc gag cag aag taa                                           213
Ser Gly Gly Glu Gln Lys
 65                  70


<210> SEQ ID NO 37
<211> LENGTH: 70
<212> TYPE: PRT
<213> ORGANISM: Botrytis cinerea

<400> SEQUENCE: 37

Gly Glu Gly Asp Thr Gly Ala Ala Arg Phe Gly Gly Gln Gln Asp Ala
 1               5                  10                  15

Phe Thr Lys Arg Glu Lys Ala Asn Glu Asp Tyr Thr Ile Arg Gln Arg
            20                  25                  30

Glu Asn Glu Lys Leu Leu Glu Leu Arg Lys Lys Ile Thr Glu Gln Arg
        35                  40                  45

Asp His Leu Lys Lys Leu Glu Asp His Ile Ser Glu Ile Glu Lys Gln
    50                  55                  60

Ser Gly Gly Glu Gln Lys
65                  70


<210> SEQ ID NO 38
<211> LENGTH: 306
<212> TYPE: DNA
<213> ORGANISM: Botrytis cinerea
<220> FEATURE:
<221> NAME/KEY: misc_feature
<222> LOCATION: (1)...(306)
<223> OTHER INFORMATION: BcAFP2 full-length cds
<220> FEATURE:
<221> NAME/KEY: CDS
<222> LOCATION: (1)...(306)
<223> OTHER INFORMATION: BcAFP2 full-length pp

<400> SEQUENCE: 38

atg tat cgt ctt gca atc aac tct gcc atg cga cca gca gtc cgc gca        48
Met Tyr Arg Leu Ala Ile Asn Ser Ala Met Arg Pro Ala Val Arg Ala
 1               5                  10                  15

tcc gtc cca gct gcc aga gca ttt acc gta tca gca cgc act atg ggc        96
Ser Val Pro Ala Ala Arg Ala Phe Thr Val Ser Ala Arg Thr Met Gly
            20                  25                  30

gag gga gac acc ggc gct gcc aga ttt ggc ggc caa caa gat gcc ttt       144
Glu Gly Asp Thr Gly Ala Ala Arg Phe Gly Gly Gln Gln Asp Ala Phe
        35                  40                  45

acc aaa cgc gaa aag gcc aat gag gat tac acc atc cgc cag cgt gag       192
Thr Lys Arg Glu Lys Ala Asn Glu Asp Tyr Thr Ile Arg Gln Arg Glu
    50                  55                  60

aat gag aag ctc ttg gag ttg agg aag aaa atc acc gaa cag cgt gat       240
Asn Glu Lys Leu Leu Glu Leu Arg Lys Lys Ile Thr Glu Gln Arg Asp
 65                  70                  75                  80
```

```
cac ttg aag aaa ctc gag gac cac att tcc gaa atc gag aag caa tct      288
His Leu Lys Lys Leu Glu Asp His Ile Ser Glu Ile Glu Lys Gln Ser
                85                  90                  95

ggt ggc gag cag aac taa                                              306
Gly Gly Glu Gln Asn
            100


<210> SEQ ID NO 39
<211> LENGTH: 101
<212> TYPE: PRT
<213> ORGANISM: Botrytis cinerea

<400> SEQUENCE: 39

Met Tyr Arg Leu Ala Ile Asn Ser Ala Met Arg Pro Ala Val Arg Ala
 1               5                  10                  15

Ser Val Pro Ala Ala Arg Ala Phe Thr Val Ser Ala Arg Thr Met Gly
            20                  25                  30

Glu Gly Asp Thr Gly Ala Ala Arg Phe Gly Gly Gln Gln Asp Ala Phe
        35                  40                  45

Thr Lys Arg Glu Lys Ala Asn Glu Asp Tyr Thr Ile Arg Gln Arg Glu
    50                  55                  60

Asn Glu Lys Leu Leu Glu Leu Arg Lys Lys Ile Thr Glu Gln Arg Asp
65                  70                  75                  80

His Leu Lys Lys Leu Glu Asp His Ile Ser Glu Ile Glu Lys Gln Ser
                85                  90                  95

Gly Gly Glu Gln Asn
            100


<210> SEQ ID NO 40
<211> LENGTH: 213
<212> TYPE: DNA
<213> ORGANISM: Botrytis cinerea
<220> FEATURE:
<221> NAME/KEY: misc_feature
<222> LOCATION: (1)...(213)
<223> OTHER INFORMATION: BcAFP2 mature cds
<220> FEATURE:
<221> NAME/KEY: CDS
<222> LOCATION: (1)...(213)
<223> OTHER INFORMATION: BcAFP2 mature pp

<400> SEQUENCE: 40

ggc gag gga gac acc ggc gct gcc aga ttt ggc ggc caa caa gat gcc       48
Gly Glu Gly Asp Thr Gly Ala Ala Arg Phe Gly Gly Gln Gln Asp Ala
 1               5                  10                  15

ttt acc aaa cgc gaa aag gcc aat gag gat tac acc atc cgc cag cgt       96
Phe Thr Lys Arg Glu Lys Ala Asn Glu Asp Tyr Thr Ile Arg Gln Arg
            20                  25                  30

gag aat gag aag ctc ttg gag ttg agg aag aaa atc acc gaa cag cgt      144
Glu Asn Glu Lys Leu Leu Glu Leu Arg Lys Lys Ile Thr Glu Gln Arg
        35                  40                  45

gat cac ttg aag aaa ctc gag gac cac att tcc gaa atc gag aag caa      192
Asp His Leu Lys Lys Leu Glu Asp His Ile Ser Glu Ile Glu Lys Gln
    50                  55                  60

tct ggt ggc gag cag aac taa                                          213
Ser Gly Gly Glu Gln Asn
65                  70


<210> SEQ ID NO 41
<211> LENGTH: 70
<212> TYPE: PRT
<213> ORGANISM: Botrytis cinerea
```

```
<400> SEQUENCE: 41

Gly Glu Gly Asp Thr Gly Ala Ala Arg Phe Gly Gly Gln Gln Asp Ala
 1               5                  10                  15

Phe Thr Lys Arg Glu Lys Ala Asn Glu Asp Tyr Thr Ile Arg Gln Arg
            20                  25                  30

Glu Asn Glu Lys Leu Leu Glu Leu Arg Lys Lys Ile Thr Glu Gln Arg
        35                  40                  45

Asp His Leu Lys Lys Leu Glu Asp His Ile Ser Glu Ile Glu Lys Gln
    50                  55                  60

Ser Gly Gly Glu Gln Asn
65                  70


<210> SEQ ID NO 42
<211> LENGTH: 294
<212> TYPE: DNA
<213> ORGANISM: Chaetomium globosum
<220> FEATURE:
<221> NAME/KEY: misc_feature
<222> LOCATION: (1)...(294)
<223> OTHER INFORMATION: CgAFP1 (Chaetomium globosum) full-length cds
<220> FEATURE:
<221> NAME/KEY: CDS
<222> LOCATION: (1)...(294)
<223> OTHER INFORMATION: CgAFP1 (Chaetomium globosum) full-length pp

<400> SEQUENCE: 42

atg atg cgc acc tcc atc gct aag ctc gcc cgc ccg gcc ctg ctc tcc       48
Met Met Arg Thr Ser Ile Ala Lys Leu Ala Arg Pro Ala Leu Leu Ser
 1               5                  10                  15

cgc acc ttc gcc acg acc acc cgg gtc atg gcc gcc ggc gac acc ggc       96
Arg Thr Phe Ala Thr Thr Thr Arg Val Met Ala Ala Gly Asp Thr Gly
             20                  25                  30

gct ccg ccc aag acc ggc ggc gcg ggc gac gcc ttc cag aaa cgc gag      144
Ala Pro Pro Lys Thr Gly Gly Ala Gly Asp Ala Phe Gln Lys Arg Glu
         35                  40                  45

cgc gcc agc gag gac ttt gcg atc cgc cag cgc gag aag cag aag ctc      192
Arg Ala Ser Glu Asp Phe Ala Ile Arg Gln Arg Glu Lys Gln Lys Leu
     50                  55                  60

atg gag ctc aag aag aag ctg gcc gag cag cag gcc cac ctg cag cag      240
Met Glu Leu Lys Lys Lys Leu Ala Glu Gln Gln Ala His Leu Gln Gln
 65                  70                  75                  80

ctc tcc gac cac atc gac gag atc acc cag gag cag ggc ggc gag cag      288
Leu Ser Asp His Ile Asp Glu Ile Thr Gln Glu Gln Gly Gly Glu Gln
                 85                  90                  95

aac taa                                                              294
Asn


<210> SEQ ID NO 43
<211> LENGTH: 97
<212> TYPE: PRT
<213> ORGANISM: Chaetomium globosum

<400> SEQUENCE: 43

Met Met Arg Thr Ser Ile Ala Lys Leu Ala Arg Pro Ala Leu Leu Ser
 1               5                  10                  15

Arg Thr Phe Ala Thr Thr Thr Arg Val Met Ala Ala Gly Asp Thr Gly
            20                  25                  30

Ala Pro Pro Lys Thr Gly Gly Ala Gly Asp Ala Phe Gln Lys Arg Glu
        35                  40                  45

Arg Ala Ser Glu Asp Phe Ala Ile Arg Gln Arg Glu Lys Gln Lys Leu
```

```
    50                  55                  60

Met Glu Leu Lys Lys Lys Leu Ala Glu Gln Gln Ala His Leu Gln Gln
65                  70                  75                  80

Leu Ser Asp His Ile Asp Glu Ile Thr Gln Glu Gln Gly Gly Glu Gln
                85                  90                  95

Asn


<210> SEQ ID NO 44
<211> LENGTH: 216
<212> TYPE: DNA
<213> ORGANISM: Chaetomium globosum
<220> FEATURE:
<221> NAME/KEY: misc_feature
<222> LOCATION: (1)...(216)
<223> OTHER INFORMATION: CgAFP1 mature cds
<220> FEATURE:
<221> NAME/KEY: CDS
<222> LOCATION: (1)...(216)
<223> OTHER INFORMATION: CgAFP1 mature pp

<400> SEQUENCE: 44

gcc gcc ggc gac acc ggc gct ccg ccc aag acc ggc ggc gcg ggc gac       48
Ala Ala Gly Asp Thr Gly Ala Pro Pro Lys Thr Gly Gly Ala Gly Asp
 1               5                  10                  15

gcc ttc cag aaa cgc gag cgc gcc agc gag gac ttt gcg atc cgc cag       96
Ala Phe Gln Lys Arg Glu Arg Ala Ser Glu Asp Phe Ala Ile Arg Gln
             20                  25                  30

cgc gag aag cag aag ctc atg gag ctc aag aag aag ctg gcc gag cag      144
Arg Glu Lys Gln Lys Leu Met Glu Leu Lys Lys Lys Leu Ala Glu Gln
         35                  40                  45

cag gcc cac ctg cag cag ctc tcc gac cac atc gac gag atc acc cag      192
Gln Ala His Leu Gln Gln Leu Ser Asp His Ile Asp Glu Ile Thr Gln
     50                  55                  60

gag cag ggc ggc gag cag aac taa                                      216
Glu Gln Gly Gly Glu Gln Asn
 65                  70


<210> SEQ ID NO 45
<211> LENGTH: 71
<212> TYPE: PRT
<213> ORGANISM: Chaetomium globosum

<400> SEQUENCE: 45

Ala Ala Gly Asp Thr Gly Ala Pro Pro Lys Thr Gly Gly Ala Gly Asp
 1               5                  10                  15

Ala Phe Gln Lys Arg Glu Arg Ala Ser Glu Asp Phe Ala Ile Arg Gln
             20                  25                  30

Arg Glu Lys Gln Lys Leu Met Glu Leu Lys Lys Lys Leu Ala Glu Gln
        35                  40                  45

Gln Ala His Leu Gln Gln Leu Ser Asp His Ile Asp Glu Ile Thr Gln
    50                  55                  60

Glu Gln Gly Gly Glu Gln Asn
65                  70


<210> SEQ ID NO 46
<211> LENGTH: 303
<212> TYPE: DNA
<213> ORGANISM: Coccidioides immitis
<220> FEATURE:
<221> NAME/KEY: misc_feature
<222> LOCATION: (1)...(303)
<223> OTHER INFORMATION: CiAFP1 (Coccidioides immitis) full-length cds
<220> FEATURE:
```

-continued

```
<221> NAME/KEY: CDS
<222> LOCATION: (1)...(303)
<223> OTHER INFORMATION: CiAFP1 (Coccidioides immitis) full-length pp

<400> SEQUENCE: 46

atg ctc cgc ctc tcc atc gcc aga gcc gct caa gct agc aga ctt cct       48
Met Leu Arg Leu Ser Ile Ala Arg Ala Ala Gln Ala Ser Arg Leu Pro
 1               5                  10                  15

gct tac aga tcc ttc tcc att gct gct gcc aga atg ggc gaa ggt gat       96
Ala Tyr Arg Ser Phe Ser Ile Ala Ala Ala Arg Met Gly Glu Gly Asp
            20                  25                  30

acc ggt gct gtc cgc cca ggc ggc gtc caa tct ggt gac gcc tgg acc      144
Thr Gly Ala Val Arg Pro Gly Gly Val Gln Ser Gly Asp Ala Trp Thr
        35                  40                  45

aag aag gag tcc gca cag gag aac atg ttc atc agg caa cag gag att      192
Lys Lys Glu Ser Ala Gln Glu Asn Met Phe Ile Arg Gln Gln Glu Ile
     50                  55                  60

gaa aag ctc cgt gcc ctc aag gag aag ttg aag cag cag cgc aag cac      240
Glu Lys Leu Arg Ala Leu Lys Glu Lys Leu Lys Gln Gln Arg Lys His
 65                  70                  75                  80

ctt gac gag ctt gat gcc cac att gac gag ctc acc aag cag caa ggc      288
Leu Asp Glu Leu Asp Ala His Ile Asp Glu Leu Thr Lys Gln Gln Gly
                85                  90                  95

ggt gaa cat cac taa                                                  303
Gly Glu His His
            100


<210> SEQ ID NO 47
<211> LENGTH: 100
<212> TYPE: PRT
<213> ORGANISM: Coccidioides immitis

<400> SEQUENCE: 47

Met Leu Arg Leu Ser Ile Ala Arg Ala Ala Gln Ala Ser Arg Leu Pro
 1               5                  10                  15

Ala Tyr Arg Ser Phe Ser Ile Ala Ala Ala Arg Met Gly Glu Gly Asp
            20                  25                  30

Thr Gly Ala Val Arg Pro Gly Gly Val Gln Ser Gly Asp Ala Trp Thr
        35                  40                  45

Lys Lys Glu Ser Ala Gln Glu Asn Met Phe Ile Arg Gln Gln Glu Ile
    50                  55                  60

Glu Lys Leu Arg Ala Leu Lys Glu Lys Leu Lys Gln Gln Arg Lys His
65                  70                  75                  80

Leu Asp Glu Leu Asp Ala His Ile Asp Glu Leu Thr Lys Gln Gln Gly
                85                  90                  95

Gly Glu His His
            100


<210> SEQ ID NO 48
<211> LENGTH: 219
<212> TYPE: DNA
<213> ORGANISM: Coccidioides immitis
<220> FEATURE:
<221> NAME/KEY: misc_feature
<222> LOCATION: (1)...(219)
<223> OTHER INFORMATION: CiAFP1 mature cds
<220> FEATURE:
<221> NAME/KEY: CDS
<222> LOCATION: (1)...(219)
<223> OTHER INFORMATION: CiAFP1 mature pp

<400> SEQUENCE: 48
```

-continued

```
ggc gaa ggt gat acc ggt gct gtc cgc cca ggc ggc gtc caa tct ggt       48
Gly Glu Gly Asp Thr Gly Ala Val Arg Pro Gly Gly Val Gln Ser Gly
 1               5                  10                  15

gac gcc tgg acc aag aag gag tcc gca cag gag aac atg ttc atc agg       96
Asp Ala Trp Thr Lys Lys Glu Ser Ala Gln Glu Asn Met Phe Ile Arg
            20                  25                  30

caa cag gag att gaa aag ctc cgt gcc ctc aag gag aag ttg aag cag      144
Gln Gln Glu Ile Glu Lys Leu Arg Ala Leu Lys Glu Lys Leu Lys Gln
        35                  40                  45

cag cgc aag cac ctt gac gag ctt gat gcc cac att gac gag ctc acc      192
Gln Arg Lys His Leu Asp Glu Leu Asp Ala His Ile Asp Glu Leu Thr
    50                  55                  60

aag cag caa ggc ggt gaa cat cac taa                                  219
Lys Gln Gln Gly Gly Glu His His
 65                  70
```

<210> SEQ ID NO 49
<211> LENGTH: 72
<212> TYPE: PRT
<213> ORGANISM: Coccidioides immitis

<400> SEQUENCE: 49

```
Gly Glu Gly Asp Thr Gly Ala Val Arg Pro Gly Gly Val Gln Ser Gly
 1               5                  10                  15

Asp Ala Trp Thr Lys Lys Glu Ser Ala Gln Glu Asn Met Phe Ile Arg
            20                  25                  30

Gln Gln Glu Ile Glu Lys Leu Arg Ala Leu Lys Glu Lys Leu Lys Gln
        35                  40                  45

Gln Arg Lys His Leu Asp Glu Leu Asp Ala His Ile Asp Glu Leu Thr
    50                  55                  60

Lys Gln Gln Gly Gly Glu His His
65                  70
```

<210> SEQ ID NO 50
<211> LENGTH: 291
<212> TYPE: DNA
<213> ORGANISM: Diplodia maydis
<220> FEATURE:
<221> NAME/KEY: misc_feature
<222> LOCATION: (1)...(291)
<223> OTHER INFORMATION: DmAFP1 (Diplodia maydis) full-length cds
<220> FEATURE:
<221> NAME/KEY: CDS
<222> LOCATION: (1)...(291)
<223> OTHER INFORMATION: DmAFP1 (Diplodia maydis) full-length pp

<400> SEQUENCE: 50

```
atg ctt cgc cag tcc atc acc aag ctc gcc cgg cct gcc agc acc aga       48
Met Leu Arg Gln Ser Ile Thr Lys Leu Ala Arg Pro Ala Ser Thr Arg
 1               5                  10                  15

gcc ttc tcc gtc tcc acc cga gcc atg gct gcc ggc gac acg gga gct       96
Ala Phe Ser Val Ser Thr Arg Ala Met Ala Ala Gly Asp Thr Gly Ala
            20                  25                  30

ccg ccc aag ggc cta ggc cag gcc gac gcc ttc cag aag cgc gag aag      144
Pro Pro Lys Gly Leu Gly Gln Ala Asp Ala Phe Gln Lys Arg Glu Lys
        35                  40                  45

gcc aac gag gac ttc gcc atc cgc ctg cgc gag aag gaa aag ctc ctc      192
Ala Asn Glu Asp Phe Ala Ile Arg Leu Arg Glu Lys Glu Lys Leu Leu
    50                  55                  60

gag ctc aag aag aag ctg gcc gag cag cag gcg cac ctg aag cag ctc      240
Glu Leu Lys Lys Lys Leu Ala Glu Gln Gln Ala His Leu Lys Gln Leu
 65                  70                  75                  80
```

```
tcg gac cac att gac gag atc acc aag gag cag ggc ggc gag cac aac      288
Ser Asp His Ile Asp Glu Ile Thr Lys Glu Gln Gly Gly Glu His Asn
                 85                  90                  95

taa                                                                  291


<210> SEQ ID NO 51
<211> LENGTH: 96
<212> TYPE: PRT
<213> ORGANISM: Diplodia maydis

<400> SEQUENCE: 51

Met Leu Arg Gln Ser Ile Thr Lys Leu Ala Arg Pro Ala Ser Thr Arg
 1               5                  10                  15

Ala Phe Ser Val Ser Thr Arg Ala Met Ala Ala Gly Asp Thr Gly Ala
            20                  25                  30

Pro Pro Lys Gly Leu Gly Gln Ala Asp Ala Phe Gln Lys Arg Glu Lys
        35                  40                  45

Ala Asn Glu Asp Phe Ala Ile Arg Leu Arg Glu Lys Glu Lys Leu Leu
    50                  55                  60

Glu Leu Lys Lys Lys Leu Ala Glu Gln Gln Ala His Leu Lys Gln Leu
65                  70                  75                  80

Ser Asp His Ile Asp Glu Ile Thr Lys Glu Gln Gly Gly Glu His Asn
                85                  90                  95


<210> SEQ ID NO 52
<211> LENGTH: 216
<212> TYPE: DNA
<213> ORGANISM: Diplodia maydis
<220> FEATURE:
<221> NAME/KEY: misc_feature
<222> LOCATION: (1)...(216)
<223> OTHER INFORMATION: DmAFP1 mature cds
<220> FEATURE:
<221> NAME/KEY: CDS
<222> LOCATION: (1)...(216)
<223> OTHER INFORMATION: DmAFP1 mature pp

<400> SEQUENCE: 52

gct gcc ggc gac acg gga gct ccg ccc aag ggc cta ggc cag gcc gac       48
Ala Ala Gly Asp Thr Gly Ala Pro Pro Lys Gly Leu Gly Gln Ala Asp
 1               5                  10                  15

gcc ttc cag aag cgc gag aag gcc aac gag gac ttc gcc atc cgc ctg       96
Ala Phe Gln Lys Arg Glu Lys Ala Asn Glu Asp Phe Ala Ile Arg Leu
             20                  25                  30

cgc gag aag gaa aag ctc ctc gag ctc aag aag aag ctg gcc gag cag      144
Arg Glu Lys Glu Lys Leu Leu Glu Leu Lys Lys Lys Leu Ala Glu Gln
         35                  40                  45

cag gcg cac ctg aag cag ctc tcg gac cac att gac gag atc acc aag      192
Gln Ala His Leu Lys Gln Leu Ser Asp His Ile Asp Glu Ile Thr Lys
     50                  55                  60

gag cag ggc ggc gag cac aac taa                                      216
Glu Gln Gly Gly Glu His Asn
 65                  70


<210> SEQ ID NO 53
<211> LENGTH: 71
<212> TYPE: PRT
<213> ORGANISM: Diplodia maydis

<400> SEQUENCE: 53

Ala Ala Gly Asp Thr Gly Ala Pro Pro Lys Gly Leu Gly Gln Ala Asp
 1               5                  10                  15
```

```
Ala Phe Gln Lys Arg Glu Lys Ala Asn Glu Asp Phe Ala Ile Arg Leu
            20                  25                  30

Arg Glu Lys Glu Lys Leu Leu Glu Leu Lys Lys Lys Leu Ala Glu Gln
        35                  40                  45

Gln Ala His Leu Lys Gln Leu Ser Asp His Ile Asp Glu Ile Thr Lys
    50                  55                  60

Glu Gln Gly Gly Glu His Asn
65                  70


<210> SEQ ID NO 54
<211> LENGTH: 291
<212> TYPE: DNA
<213> ORGANISM: Fusarium graminearum
<220> FEATURE:
<221> NAME/KEY: misc_feature
<222> LOCATION: (1)...(291)
<223> OTHER INFORMATION: FgAFP1 (Fusarium graminearum) full-length cds
<220> FEATURE:
<221> NAME/KEY: CDS
<222> LOCATION: (1)...(291)
<223> OTHER INFORMATION: FgAFP1 (Fusarium graminearum) full-length pp

<400> SEQUENCE: 54

atg ctt cgc aca tct ttc cgc cag gca gcc gcc ttc cga ccc att cga       48
Met Leu Arg Thr Ser Phe Arg Gln Ala Ala Ala Phe Arg Pro Ile Arg
 1               5                  10                  15

tgc ttc tct acc act ccc cgc gtc atg act gag ggt gct act gga gct       96
Cys Phe Ser Thr Thr Pro Arg Val Met Thr Glu Gly Ala Thr Gly Ala
             20                  25                  30

ccc cgc cct act gga ggc tct ggt gat gct ttc cag cga cgt gag aag      144
Pro Arg Pro Thr Gly Gly Ser Gly Asp Ala Phe Gln Arg Arg Glu Lys
         35                  40                  45

gcc agc gag gat tac gct atc cgc cag cgt gag aag gag aag ctc att      192
Ala Ser Glu Asp Tyr Ala Ile Arg Gln Arg Glu Lys Glu Lys Leu Ile
     50                  55                  60

gag ctc aag aag aag ctc cag gag cag cag cag cac ctt gac cgt ctc      240
Glu Leu Lys Lys Lys Leu Gln Glu Gln Gln Gln His Leu Asp Arg Leu
 65                  70                  75                  80

tcc aag cac att gat gag atc aca aag gag cag ggc ggc gag cag cac      288
Ser Lys His Ile Asp Glu Ile Thr Lys Glu Gln Gly Gly Glu Gln His
                 85                  90                  95

taa                                                                  291


<210> SEQ ID NO 55
<211> LENGTH: 96
<212> TYPE: PRT
<213> ORGANISM: Fusarium graminearum

<400> SEQUENCE: 55

Met Leu Arg Thr Ser Phe Arg Gln Ala Ala Ala Phe Arg Pro Ile Arg
 1               5                  10                  15

Cys Phe Ser Thr Thr Pro Arg Val Met Thr Glu Gly Ala Thr Gly Ala
            20                  25                  30

Pro Arg Pro Thr Gly Gly Ser Gly Asp Ala Phe Gln Arg Arg Glu Lys
        35                  40                  45

Ala Ser Glu Asp Tyr Ala Ile Arg Gln Arg Glu Lys Glu Lys Leu Ile
    50                  55                  60

Glu Leu Lys Lys Lys Leu Gln Glu Gln Gln Gln His Leu Asp Arg Leu
65                  70                  75                  80

Ser Lys His Ile Asp Glu Ile Thr Lys Glu Gln Gly Gly Glu Gln His
                85                  90                  95
```

<210> SEQ ID NO 56
<211> LENGTH: 216
<212> TYPE: DNA
<213> ORGANISM: Fusarium graminearum
<220> FEATURE:
<221> NAME/KEY: misc_feature
<222> LOCATION: (1)...(216)
<223> OTHER INFORMATION: FgAFP1 mature cds
<220> FEATURE:
<221> NAME/KEY: CDS
<222> LOCATION: (1)...(216)
<223> OTHER INFORMATION: FgAFP1 mature pp

<400> SEQUENCE: 56 act gag ggt gct act gga gct ccc cgc cct act gga ggc tct ggt gat 48
Thr Glu Gly Ala Thr Gly Ala Pro Arg Pro Thr Gly Gly Ser Gly Asp
1 5 10 15 gct ttc cag cga cgt gag aag gcc agc gag gat tac gct atc cgc cag 96
Ala Phe Gln Arg Arg Glu Lys Ala Ser Glu Asp Tyr Ala Ile Arg Gln
20 25 30 cgt gag aag gag aag ctc att gag ctc aag aag aag ctc cag gag cag 144
Arg Glu Lys Glu Lys Leu Ile Glu Leu Lys Lys Lys Leu Gln Glu Gln
35 40 45 cag cag cac ctt gac cgt ctc tcc aag cac att gat gag atc aca aag 192
Gln Gln His Leu Asp Arg Leu Ser Lys His Ile Asp Glu Ile Thr Lys
50 55 60 gag cag ggc ggc gag cag cac taa 216
Glu Gln Gly Gly Glu Gln His
65 70

<210> SEQ ID NO 57
<211> LENGTH: 71
<212> TYPE: PRT
<213> ORGANISM: Fusarium graminearum

<400> SEQUENCE: 57

Thr Glu Gly Ala Thr Gly Ala Pro Arg Pro Thr Gly Gly Ser Gly Asp
1 5 10 15

Ala Phe Gln Arg Arg Glu Lys Ala Ser Glu Asp Tyr Ala Ile Arg Gln
20 25 30

Arg Glu Lys Glu Lys Leu Ile Glu Leu Lys Lys Lys Leu Gln Glu Gln
35 40 45

Gln Gln His Leu Asp Arg Leu Ser Lys His Ile Asp Glu Ile Thr Lys
50 55 60

Glu Gln Gly Gly Glu Gln His
65 70

<210> SEQ ID NO 58
<211> LENGTH: 306
<212> TYPE: DNA
<213> ORGANISM: Glycine max
<220> FEATURE:
<221> NAME/KEY: misc_feature
<222> LOCATION: (1)...(306)
<223> OTHER INFORMATION: GmAFP1 (Glycine max) full-length cds
<220> FEATURE:
<221> NAME/KEY: CDS
<222> LOCATION: (1)...(306)
<223> OTHER INFORMATION: GmAFP1 (Glycine max) full-length pp

<400> SEQUENCE: 58 atg tat cgt ctc gca atc aac tct gcc ctg cga ccc gca gtc cgc aca 48
Met Tyr Arg Leu Ala Ile Asn Ser Ala Leu Arg Pro Ala Val Arg Thr
1 5 10 15

```
tcc atc cca gct gcc aga gca ttt acc gta tca gca cgc acc atg ggc       96
Ser Ile Pro Ala Ala Arg Ala Phe Thr Val Ser Ala Arg Thr Met Gly
            20                  25                  30

gag gga gac acc ggt gct gcc cga ttc ggc ggc caa caa gat gct ttc      144
Glu Gly Asp Thr Gly Ala Ala Arg Phe Gly Gly Gln Gln Asp Ala Phe
        35                  40                  45

acc aag cgc gaa aaa gcc aat gag gat ttc acc att cgc cag cgc gag      192
Thr Lys Arg Glu Lys Ala Asn Glu Asp Phe Thr Ile Arg Gln Arg Glu
    50                  55                  60

aat gag aaa ctc ttg gag ttg agg aag aaa atc aag gaa caa cgt gaa      240
Asn Glu Lys Leu Leu Glu Leu Arg Lys Lys Ile Lys Glu Gln Arg Glu
65                  70                  75                  80

cac ttg aag aaa ctc gag gac cac att tcc gaa atc gag aga caa tct      288
His Leu Lys Lys Leu Glu Asp His Ile Ser Glu Ile Glu Arg Gln Ser
                85                  90                  95

ggc ggc gag cag aag taa                                              306
Gly Gly Glu Gln Lys
            100


<210> SEQ ID NO 59
<211> LENGTH: 101
<212> TYPE: PRT
<213> ORGANISM: Glycine max

<400> SEQUENCE: 59

Met Tyr Arg Leu Ala Ile Asn Ser Ala Leu Arg Pro Ala Val Arg Thr
1               5                   10                  15

Ser Ile Pro Ala Ala Arg Ala Phe Thr Val Ser Ala Arg Thr Met Gly
            20                  25                  30

Glu Gly Asp Thr Gly Ala Ala Arg Phe Gly Gly Gln Gln Asp Ala Phe
        35                  40                  45

Thr Lys Arg Glu Lys Ala Asn Glu Asp Phe Thr Ile Arg Gln Arg Glu
    50                  55                  60

Asn Glu Lys Leu Leu Glu Leu Arg Lys Lys Ile Lys Glu Gln Arg Glu
65                  70                  75                  80

His Leu Lys Lys Leu Glu Asp His Ile Ser Glu Ile Glu Arg Gln Ser
                85                  90                  95

Gly Gly Glu Gln Lys
            100


<210> SEQ ID NO 60
<211> LENGTH: 213
<212> TYPE: DNA
<213> ORGANISM: Glycine max
<220> FEATURE:
<221> NAME/KEY: misc_feature
<222> LOCATION: (1)...(213)
<223> OTHER INFORMATION: GmAFP1 mature cds
<220> FEATURE:
<221> NAME/KEY: CDS
<222> LOCATION: (1)...(213)
<223> OTHER INFORMATION: GmAFP1 mature pp

<400> SEQUENCE: 60

ggc gag gga gac acc ggt gct gcc cga ttc ggc ggc caa caa gat gct       48
Gly Glu Gly Asp Thr Gly Ala Ala Arg Phe Gly Gly Gln Gln Asp Ala
1               5                   10                  15

ttc acc aag cgc gaa aaa gcc aat gag gat ttc acc att cgc cag cgc       96
Phe Thr Lys Arg Glu Lys Ala Asn Glu Asp Phe Thr Ile Arg Gln Arg
            20                  25                  30

gag aat gag aaa ctc ttg gag ttg agg aag aaa atc aag gaa caa cgt      144
```

-continued

```
Glu Asn Glu Lys Leu Leu Glu Leu Arg Lys Lys Ile Lys Glu Gln Arg
         35                  40                  45

gaa cac ttg aag aaa ctc gag gac cac att tcc gaa atc gag aga caa      192
Glu His Leu Lys Lys Leu Glu Asp His Ile Ser Glu Ile Glu Arg Gln
     50                  55                  60

tct ggc ggc gag cag aag taa                                          213
Ser Gly Gly Glu Gln Lys
 65                  70


<210> SEQ ID NO 61
<211> LENGTH: 70
<212> TYPE: PRT
<213> ORGANISM: Glycine max

<400> SEQUENCE: 61

Gly Glu Gly Asp Thr Gly Ala Ala Arg Phe Gly Gly Gln Gln Asp Ala
 1               5                   10                  15

Phe Thr Lys Arg Glu Lys Ala Asn Glu Asp Phe Thr Ile Arg Gln Arg
            20                  25                  30

Glu Asn Glu Lys Leu Leu Glu Leu Arg Lys Lys Ile Lys Glu Gln Arg
        35                  40                  45

Glu His Leu Lys Lys Leu Glu Asp His Ile Ser Glu Ile Glu Arg Gln
    50                  55                  60

Ser Gly Gly Glu Gln Lys
65                  70


<210> SEQ ID NO 62
<211> LENGTH: 303
<212> TYPE: DNA
<213> ORGANISM: Magnaporthe grisea
<220> FEATURE:
<221> NAME/KEY: misc_feature
<222> LOCATION: (1)...(303)
<223> OTHER INFORMATION: MgAFP1 (Magnaporthe grisea) full-length cds
<220> FEATURE:
<221> NAME/KEY: CDS
<222> LOCATION: (1)...(303)
<223> OTHER INFORMATION: MgAFP1 (Magnaporthe grisea) full-length pp

<400> SEQUENCE: 62

atg ctt cgc cag tca ttt acc aag gtt gcc aga ccc gct gtc agg ctt       48
Met Leu Arg Gln Ser Phe Thr Lys Val Ala Arg Pro Ala Val Arg Leu
 1               5                   10                  15

tca aac gcc cgc gtt gcc ttc tcg acg tca gca atc agg atg gcc gag       96
Ser Asn Ala Arg Val Ala Phe Ser Thr Ser Ala Ile Arg Met Ala Glu
            20                  25                  30

ggt gat ctc ggg tct acc ccc aag act ggt ggc gga gac gcc ttc cag      144
Gly Asp Leu Gly Ser Thr Pro Lys Thr Gly Gly Gly Asp Ala Phe Gln
         35                  40                  45

aag cgt gaa cgc gcg cag gag gac tac gcc atc cgc cag cgt gag aag      192
Lys Arg Glu Arg Ala Gln Glu Asp Tyr Ala Ile Arg Gln Arg Glu Lys
     50                  55                  60

gaa aag ctt ctc gag ctc aag aag aag ctc gcc gag cag caa gct cac      240
Glu Lys Leu Leu Glu Leu Lys Lys Lys Leu Ala Glu Gln Gln Ala His
 65                  70                  75                  80

ctg aac aag ctt tcc gag cac atc gac gag ctc aca aag agt cag gga      288
Leu Asn Lys Leu Ser Glu His Ile Asp Glu Leu Thr Lys Ser Gln Gly
                85                  90                  95

ggc gag cag aac taa                                                  303
Gly Glu Gln Asn
            100
```

```
<210> SEQ ID NO 63
<211> LENGTH: 100
<212> TYPE: PRT
<213> ORGANISM: Magnaporthe grisea

<400> SEQUENCE: 63

Met Leu Arg Gln Ser Phe Thr Lys Val Ala Arg Pro Ala Val Arg Leu
 1               5                  10                  15

Ser Asn Ala Arg Val Ala Phe Ser Thr Ser Ala Ile Arg Met Ala Glu
            20                  25                  30

Gly Asp Leu Gly Ser Thr Pro Lys Thr Gly Gly Gly Asp Ala Phe Gln
        35                  40                  45

Lys Arg Glu Arg Ala Gln Glu Asp Tyr Ala Ile Arg Gln Arg Glu Lys
    50                  55                  60

Glu Lys Leu Leu Glu Leu Lys Lys Lys Leu Ala Glu Gln Gln Ala His
65                  70                  75                  80

Leu Asn Lys Leu Ser Glu His Ile Asp Glu Leu Thr Lys Ser Gln Gly
                85                  90                  95

Gly Glu Gln Asn
            100


<210> SEQ ID NO 64
<211> LENGTH: 213
<212> TYPE: DNA
<213> ORGANISM: Magnaporthe grisea
<220> FEATURE:
<221> NAME/KEY: misc_feature
<222> LOCATION: (1)...(213)
<223> OTHER INFORMATION: MgAFP1 mature cds
<220> FEATURE:
<221> NAME/KEY: CDS
<222> LOCATION: (1)...(213)
<223> OTHER INFORMATION: MgAFP1 mature pp

<400> SEQUENCE: 64

gcc gag ggt gat ctc ggg tct acc ccc aag act ggt ggc gga gac gcc       48
Ala Glu Gly Asp Leu Gly Ser Thr Pro Lys Thr Gly Gly Gly Asp Ala
 1               5                   10                  15

ttc cag aag cgt gaa cgc gcg cag gag gac tac gcc atc cgc cag cgt       96
Phe Gln Lys Arg Glu Arg Ala Gln Glu Asp Tyr Ala Ile Arg Gln Arg
             20                  25                  30

gag aag gaa aag ctt ctc gag ctc aag aag aag ctc gcc gag cag caa      144
Glu Lys Glu Lys Leu Leu Glu Leu Lys Lys Lys Leu Ala Glu Gln Gln
         35                  40                  45

gct cac ctg aac aag ctt tcc gag cac atc gac gag ctc aca aag agt      192
Ala His Leu Asn Lys Leu Ser Glu His Ile Asp Glu Leu Thr Lys Ser
     50                  55                  60

cag gga ggc gag cag aac taa                                          213
Gln Gly Gly Glu Gln Asn
 65                  70


<210> SEQ ID NO 65
<211> LENGTH: 70
<212> TYPE: PRT
<213> ORGANISM: Magnaporthe grisea

<400> SEQUENCE: 65

Ala Glu Gly Asp Leu Gly Ser Thr Pro Lys Thr Gly Gly Gly Asp Ala
 1               5                  10                  15

Phe Gln Lys Arg Glu Arg Ala Gln Glu Asp Tyr Ala Ile Arg Gln Arg
            20                  25                  30

Glu Lys Glu Lys Leu Leu Glu Leu Lys Lys Lys Leu Ala Glu Gln Gln
```

-continued

```
        35                  40                  45

Ala His Leu Asn Lys Leu Ser Glu His Ile Asp Glu Leu Thr Lys Ser
    50                  55                  60

Gln Gly Gly Glu Gln Asn
65                  70


<210> SEQ ID NO 66
<211> LENGTH: 351
<212> TYPE: DNA
<213> ORGANISM: Magnaporthe grisea
<220> FEATURE:
<221> NAME/KEY: misc_feature
<222> LOCATION: (1)...(351)
<223> OTHER INFORMATION: MgAFP2 full-length cds
<220> FEATURE:
<221> NAME/KEY: CDS
<222> LOCATION: (1)...(351)
<223> OTHER INFORMATION: MgAFP2 full-length pp

<400> SEQUENCE: 66

atg ctt cgc cag tca ttt acc aag gtt gcc aga ccc gct gtc agg ctt        48
Met Leu Arg Gln Ser Phe Thr Lys Val Ala Arg Pro Ala Val Arg Leu
 1               5                  10                  15

tca aac gcc cgc gtt gcc ttc tcg acg tca gca atc agg atg gcc gag        96
Ser Asn Ala Arg Val Ala Phe Ser Thr Ser Ala Ile Arg Met Ala Glu
             20                  25                  30

ggt gat ctc ggg tct acc ccc aag act ggt ggc gga gac gcc ttc cag       144
Gly Asp Leu Gly Ser Thr Pro Lys Thr Gly Gly Gly Asp Ala Phe Gln
         35                  40                  45

aag cgt gaa cgc gcg cag gag gac tac gcc atc cgc cag cgt gag aag       192
Lys Arg Glu Arg Ala Gln Glu Asp Tyr Ala Ile Arg Gln Arg Glu Lys
     50                  55                  60

gaa aag ctt ctc gag ctc aag aag aag ctc gcc gag cag caa gct cac       240
Glu Lys Leu Leu Glu Leu Lys Lys Lys Leu Ala Glu Gln Gln Ala His
 65                  70                  75                  80

ctg aac aag ctt tcc gag cac atg tac gcg ttt acc tcc cgg aac gat       288
Leu Asn Lys Leu Ser Glu His Met Tyr Ala Phe Thr Ser Arg Asn Asp
                 85                  90                  95

tcg ccc tct tgc tta tgt cga gga gga cta tcc ctt gac ctt gta cca       336
Ser Pro Ser Cys Leu Cys Arg Gly Gly Leu Ser Leu Asp Leu Val Pro
            100                 105                 110

aaa ttc gaa aaa taa                                                   351
Lys Phe Glu Lys
        115


<210> SEQ ID NO 67
<211> LENGTH: 116
<212> TYPE: PRT
<213> ORGANISM: Magnaporthe grisea

<400> SEQUENCE: 67

Met Leu Arg Gln Ser Phe Thr Lys Val Ala Arg Pro Ala Val Arg Leu
 1               5                  10                  15

Ser Asn Ala Arg Val Ala Phe Ser Thr Ser Ala Ile Arg Met Ala Glu
            20                  25                  30

Gly Asp Leu Gly Ser Thr Pro Lys Thr Gly Gly Gly Asp Ala Phe Gln
        35                  40                  45

Lys Arg Glu Arg Ala Gln Glu Asp Tyr Ala Ile Arg Gln Arg Glu Lys
    50                  55                  60

Glu Lys Leu Leu Glu Leu Lys Lys Lys Leu Ala Glu Gln Gln Ala His
65                  70                  75                  80
```

```
Leu Asn Lys Leu Ser Glu His Met Tyr Ala Phe Thr Ser Arg Asn Asp
                85                  90                  95

Ser Pro Ser Cys Leu Cys Arg Gly Gly Leu Ser Leu Asp Leu Val Pro
            100                 105                 110

Lys Phe Glu Lys
        115


<210> SEQ ID NO 68
<211> LENGTH: 261
<212> TYPE: DNA
<213> ORGANISM: Magnaporthe grisea
<220> FEATURE:
<221> NAME/KEY: misc_feature
<222> LOCATION: (1)...(261)
<223> OTHER INFORMATION: MgAFP2 mature cds
<220> FEATURE:
<221> NAME/KEY: CDS
<222> LOCATION: (1)...(261)
<223> OTHER INFORMATION: MgAFP2 mature pp

<400> SEQUENCE: 68

gcc gag ggt gat ctc ggg tct acc ccc aag act ggt ggc gga gac gcc       48
Ala Glu Gly Asp Leu Gly Ser Thr Pro Lys Thr Gly Gly Gly Asp Ala
 1               5                  10                  15

ttc cag aag cgt gaa cgc gcg cag gag gac tac gcc atc cgc cag cgt       96
Phe Gln Lys Arg Glu Arg Ala Gln Glu Asp Tyr Ala Ile Arg Gln Arg
            20                  25                  30

gag aag gaa aag ctt ctc gag ctc aag aag aag ctc gcc gag cag caa      144
Glu Lys Glu Lys Leu Leu Glu Leu Lys Lys Lys Leu Ala Glu Gln Gln
        35                  40                  45

gct cac ctg aac aag ctt tcc gag cac atg tac gcg ttt acc tcc cgg      192
Ala His Leu Asn Lys Leu Ser Glu His Met Tyr Ala Phe Thr Ser Arg
    50                  55                  60

aac gat tcg ccc tct tgc tta tgt cga gga gga cta tcc ctt gac ctt      240
Asn Asp Ser Pro Ser Cys Leu Cys Arg Gly Gly Leu Ser Leu Asp Leu
65                  70                  75                  80

gta cca aaa ttc gaa aaa taa                                          261
Val Pro Lys Phe Glu Lys
                85


<210> SEQ ID NO 69
<211> LENGTH: 86
<212> TYPE: PRT
<213> ORGANISM: Magnaporthe grisea

<400> SEQUENCE: 69

Ala Glu Gly Asp Leu Gly Ser Thr Pro Lys Thr Gly Gly Gly Asp Ala
 1               5                  10                  15

Phe Gln Lys Arg Glu Arg Ala Gln Glu Asp Tyr Ala Ile Arg Gln Arg
            20                  25                  30

Glu Lys Glu Lys Leu Leu Glu Leu Lys Lys Lys Leu Ala Glu Gln Gln
        35                  40                  45

Ala His Leu Asn Lys Leu Ser Glu His Met Tyr Ala Phe Thr Ser Arg
    50                  55                  60

Asn Asp Ser Pro Ser Cys Leu Cys Arg Gly Gly Leu Ser Leu Asp Leu
65                  70                  75                  80

Val Pro Lys Phe Glu Lys
                85


<210> SEQ ID NO 70
<211> LENGTH: 219
<212> TYPE: DNA
```

```
<213> ORGANISM: Nectria haematococca
<220> FEATURE:
<221> NAME/KEY: misc_feature
<222> LOCATION: (1)...(219)
<223> OTHER INFORMATION: NhAFP1 (Nectria haematococca) full-length cds
<220> FEATURE:
<221> NAME/KEY: CDS
<222> LOCATION: (1)...(219)
<223> OTHER INFORMATION: NhAFP1 (Nectria haematococca) full-length pp

<400> SEQUENCE: 70

atg acc gag ggt gct acc ggt gct cct ccc aag acc ggc ggt cct ggt       48
Met Thr Glu Gly Ala Thr Gly Ala Pro Pro Lys Thr Gly Gly Pro Gly
 1               5                  10                  15

gac gcc ttc cag cga cga gag aag gcc aac gag gat tac gcc atc cgc       96
Asp Ala Phe Gln Arg Arg Glu Lys Ala Asn Glu Asp Tyr Ala Ile Arg
             20                  25                  30

cag cgc gag aag gag aag ctc att gag ctc aag aag aag ctc cag gag      144
Gln Arg Glu Lys Glu Lys Leu Ile Glu Leu Lys Lys Lys Leu Gln Glu
         35                  40                  45

cag cag cag cac ctc gag cgc ctc tcc aag cac atc gac gag atc acc      192
Gln Gln Gln His Leu Glu Arg Leu Ser Lys His Ile Asp Glu Ile Thr
     50                  55                  60

aag gag cag ggc ggc gag cag aac taa                                  219
Lys Glu Gln Gly Gly Glu Gln Asn
 65                  70


<210> SEQ ID NO 71
<211> LENGTH: 72
<212> TYPE: PRT
<213> ORGANISM: Nectria haematococca

<400> SEQUENCE: 71

Met Thr Glu Gly Ala Thr Gly Ala Pro Pro Lys Thr Gly Gly Pro Gly
 1               5                  10                  15

Asp Ala Phe Gln Arg Arg Glu Lys Ala Asn Glu Asp Tyr Ala Ile Arg
             20                  25                  30

Gln Arg Glu Lys Glu Lys Leu Ile Glu Leu Lys Lys Lys Leu Gln Glu
         35                  40                  45

Gln Gln Gln His Leu Glu Arg Leu Ser Lys His Ile Asp Glu Ile Thr
     50                  55                  60

Lys Glu Gln Gly Gly Glu Gln Asn
65                  70


<210> SEQ ID NO 72
<211> LENGTH: 300
<212> TYPE: DNA
<213> ORGANISM: Neosartorya fischeri
<220> FEATURE:
<221> NAME/KEY: misc_feature
<222> LOCATION: (1)...(300)
<223> OTHER INFORMATION: NfAFP1 (Neosartorya fischeri) full-length cds
<220> FEATURE:
<221> NAME/KEY: CDS
<222> LOCATION: (1)...(300)
<223> OTHER INFORMATION: NfAFP1 (Neosartorya fischeri) full-length pp

<400> SEQUENCE: 72

atg ctc cgc caa tcc gtc cgt ccc ctc aca acc gcc aac cgc gct ctc       48
Met Leu Arg Gln Ser Val Arg Pro Leu Thr Thr Ala Asn Arg Ala Leu
 1               5                  10                  15

acc cgc tcc ttc tct gct ctt gct ccc aga atg ggt gaa ggc gac act       96
Thr Arg Ser Phe Ser Ala Leu Ala Pro Arg Met Gly Glu Gly Asp Thr
             20                  25                  30
```

```
ggt gct cct cgt gct ggc ggt gtt cag agc ggg gat tcc ttc aca cgc      144
Gly Ala Pro Arg Ala Gly Gly Val Gln Ser Gly Asp Ser Phe Thr Arg
         35                  40                  45

cgg gaa gct gca cag gaa agc atg tac atc cac gag aag gag aag gag      192
Arg Glu Ala Ala Gln Glu Ser Met Tyr Ile His Glu Lys Glu Lys Glu
     50                  55                  60

aag ctc gca tct ctc aag aga aag atc cag gaa caa caa gag cat ctc      240
Lys Leu Ala Ser Leu Lys Arg Lys Ile Gln Glu Gln Gln Glu His Leu
 65                  70                  75                  80

aat gag ctt gat aag cat ctt aag gag ctc tcc cgg aac cag ggc ggc      288
Asn Glu Leu Asp Lys His Leu Lys Glu Leu Ser Arg Asn Gln Gly Gly
                 85                  90                  95

gag aat aac taa                                                      300
Glu Asn Asn


<210> SEQ ID NO 73
<211> LENGTH: 99
<212> TYPE: PRT
<213> ORGANISM: Neosartorya fischeri

<400> SEQUENCE: 73

Met Leu Arg Gln Ser Val Arg Pro Leu Thr Thr Ala Asn Arg Ala Leu
 1               5                  10                  15

Thr Arg Ser Phe Ser Ala Leu Ala Pro Arg Met Gly Glu Gly Asp Thr
            20                  25                  30

Gly Ala Pro Arg Ala Gly Gly Val Gln Ser Gly Asp Ser Phe Thr Arg
        35                  40                  45

Arg Glu Ala Ala Gln Glu Ser Met Tyr Ile His Glu Lys Glu Lys Glu
    50                  55                  60

Lys Leu Ala Ser Leu Lys Arg Lys Ile Gln Glu Gln Gln Glu His Leu
65                  70                  75                  80

Asn Glu Leu Asp Lys His Leu Lys Glu Leu Ser Arg Asn Gln Gly Gly
                85                  90                  95

Glu Asn Asn


<210> SEQ ID NO 74
<211> LENGTH: 219
<212> TYPE: DNA
<213> ORGANISM: Neosartorya fischeri
<220> FEATURE:
<221> NAME/KEY: misc_feature
<222> LOCATION: (1)...(219)
<223> OTHER INFORMATION: NfAFP1 mature cds
<220> FEATURE:
<221> NAME/KEY: CDS
<222> LOCATION: (1)...(219)
<223> OTHER INFORMATION: NfAFP1 mature pp

<400> SEQUENCE: 74

ggt gaa ggc gac act ggt gct cct cgt gct ggc ggt gtt cag agc ggg       48
Gly Glu Gly Asp Thr Gly Ala Pro Arg Ala Gly Gly Val Gln Ser Gly
 1               5                  10                  15

gat tcc ttc aca cgc cgg gaa gct gca cag gaa agc atg tac atc cac       96
Asp Ser Phe Thr Arg Arg Glu Ala Ala Gln Glu Ser Met Tyr Ile His
             20                  25                  30

gag aag gag aag gag aag ctc gca tct ctc aag aga aag atc cag gaa      144
Glu Lys Glu Lys Glu Lys Leu Ala Ser Leu Lys Arg Lys Ile Gln Glu
         35                  40                  45

caa caa gag cat ctc aat gag ctt gat aag cat ctt aag gag ctc tcc      192
Gln Gln Glu His Leu Asn Glu Leu Asp Lys His Leu Lys Glu Leu Ser
     50                  55                  60
```

```
cgg aac cag ggc ggc gag aat aac taa                               219
Arg Asn Gln Gly Gly Glu Asn Asn
 65                  70


<210> SEQ ID NO 75
<211> LENGTH: 72
<212> TYPE: PRT
<213> ORGANISM: Neosartorya fischeri

<400> SEQUENCE: 75

Gly Glu Gly Asp Thr Gly Ala Pro Arg Ala Gly Gly Val Gln Ser Gly
 1               5                  10                  15

Asp Ser Phe Thr Arg Arg Glu Ala Ala Gln Glu Ser Met Tyr Ile His
            20                  25                  30

Glu Lys Glu Lys Glu Lys Leu Ala Ser Leu Lys Arg Lys Ile Gln Glu
        35                  40                  45

Gln Gln Glu His Leu Asn Glu Leu Asp Lys His Leu Lys Glu Leu Ser
    50                  55                  60

Arg Asn Gln Gly Gly Glu Asn Asn
65                  70


<210> SEQ ID NO 76
<211> LENGTH: 288
<212> TYPE: DNA
<213> ORGANISM: Neurospora crassa
<220> FEATURE:
<221> NAME/KEY: misc_feature
<222> LOCATION: (1)...(288)
<223> OTHER INFORMATION: NcAFP1 (Neurospora crassa) mature cds
<220> FEATURE:
<221> NAME/KEY: CDS
<222> LOCATION: (1)...(288)
<223> OTHER INFORMATION: NcAFP1 (Neurospora crassa) mature pp

<400> SEQUENCE: 76

atg ctc cgc acc acc gtc tcc aag ctc gct cgc cct acc gtt tcc agg       48
Met Leu Arg Thr Thr Val Ser Lys Leu Ala Arg Pro Thr Val Ser Arg
 1               5                  10                  15

gcg ttt gcg acc acc tcc cgc gct ctc gcc ggt gag act ggt gct ccc       96
Ala Phe Ala Thr Thr Ser Arg Ala Leu Ala Gly Glu Thr Gly Ala Pro
            20                  25                  30

cca aag acc ggc ggc cca ggt gac gct ttc cag cgc cgc gag aag gcc      144
Pro Lys Thr Gly Gly Pro Gly Asp Ala Phe Gln Arg Arg Glu Lys Ala
        35                  40                  45

aac gag gat ttc gct atc cgc cag cgc gag aag gag aag ctc ctc gag      192
Asn Glu Asp Phe Ala Ile Arg Gln Arg Glu Lys Glu Lys Leu Leu Glu
    50                  55                  60

ctc aag aag aag ctc gcc gag cag cag aag cac ctc aag act ctt tct      240
Leu Lys Lys Lys Leu Ala Glu Gln Gln Lys His Leu Lys Thr Leu Ser
 65                  70                  75                  80

gat cac att gac gag atc acc agg gag cag ggc ggc gag cgc aac taa      288
Asp His Ile Asp Glu Ile Thr Arg Glu Gln Gly Gly Glu Arg Asn
                85                  90                  95


<210> SEQ ID NO 77
<211> LENGTH: 95
<212> TYPE: PRT
<213> ORGANISM: Neurospora crassa

<400> SEQUENCE: 77

Met Leu Arg Thr Thr Val Ser Lys Leu Ala Arg Pro Thr Val Ser Arg
 1               5                  10                  15

Ala Phe Ala Thr Thr Ser Arg Ala Leu Ala Gly Glu Thr Gly Ala Pro
```

-continued

```
            20                  25                  30

Pro Lys Thr Gly Gly Pro Gly Asp Ala Phe Gln Arg Arg Glu Lys Ala
        35                  40                  45

Asn Glu Asp Phe Ala Ile Arg Gln Arg Glu Lys Glu Lys Leu Leu Glu
    50                  55                  60

Leu Lys Lys Lys Leu Ala Glu Gln Gln Lys His Leu Lys Thr Leu Ser
65                  70                  75                  80

Asp His Ile Asp Glu Ile Thr Arg Glu Gln Gly Gly Glu Arg Asn
                85                  90                  95


<210> SEQ ID NO 78
<211> LENGTH: 453
<212> TYPE: DNA
<213> ORGANISM: Neurospora crassa
<220> FEATURE:
<221> NAME/KEY: misc_feature
<222> LOCATION: (1)...(453)
<223> OTHER INFORMATION: NcAFP2 full-length cds
<220> FEATURE:
<221> NAME/KEY: CDS
<222> LOCATION: (1)...(453)
<223> OTHER INFORMATION: NcAFP2 full-length pp

<400> SEQUENCE: 78

atg atc tcc ggc tcc atg gag ttt ggc aaa atc cat gcc gtg gta gtt       48
Met Ile Ser Gly Ser Met Glu Phe Gly Lys Ile His Ala Val Val Val
 1               5                  10                  15

gcc gag ccg tca gcg gac agg cgg agc aag tcg gcg cca gaa gcc acg       96
Ala Glu Pro Ser Ala Asp Arg Arg Ser Lys Ser Ala Pro Glu Ala Thr
            20                  25                  30

agc ctt gag cct tgt ccc ggt atg gaa ggt aag aaa aag gta gct tac      144
Ser Leu Glu Pro Cys Pro Gly Met Glu Gly Lys Lys Lys Val Ala Tyr
        35                  40                  45

acc aac ttc cgc gac tgt cca act gtt tcc aac caa acc acc aaa cca      192
Thr Asn Phe Arg Asp Cys Pro Thr Val Ser Asn Gln Thr Thr Lys Pro
    50                  55                  60

acc atc aag atg ctc cgc acc acc gtc tcc aag ctc gct cgc cct acc      240
Thr Ile Lys Met Leu Arg Thr Thr Val Ser Lys Leu Ala Arg Pro Thr
 65                 70                  75                  80

gtt tcc agg gcg ttt gcg acc acc tcc cgc gct ctc gcc ggt gag act      288
Val Ser Arg Ala Phe Ala Thr Thr Ser Arg Ala Leu Ala Gly Glu Thr
                85                  90                  95

ggt gct ccc cca aag acc ggc ggc cca ggt gac gct ttc cag cgc cgc      336
Gly Ala Pro Pro Lys Thr Gly Gly Pro Gly Asp Ala Phe Gln Arg Arg
            100                 105                 110

gag aag gcc aac gag gat ttc gct atc cgc cag cgc gag aag gag aag      384
Glu Lys Ala Asn Glu Asp Phe Ala Ile Arg Gln Arg Glu Lys Glu Lys
        115                 120                 125

ctc ctc gag ctc aag aag aag ctc gcc gag cag cag aag cac ctc aag      432
Leu Leu Glu Leu Lys Lys Lys Leu Ala Glu Gln Gln Lys His Leu Lys
    130                 135                 140

act ctt tct gat cac atg taa                                          453
Thr Leu Ser Asp His Met
145                 150


<210> SEQ ID NO 79
<211> LENGTH: 150
<212> TYPE: PRT
<213> ORGANISM: Neurospora crassa

<400> SEQUENCE: 79

Met Ile Ser Gly Ser Met Glu Phe Gly Lys Ile His Ala Val Val Val
```

-continued

```
 1               5                   10                  15

Ala Glu Pro Ser Ala Asp Arg Arg Ser Lys Ser Ala Pro Glu Ala Thr
            20                  25                  30

Ser Leu Glu Pro Cys Pro Gly Met Glu Gly Lys Lys Lys Val Ala Tyr
        35                  40                  45

Thr Asn Phe Arg Asp Cys Pro Thr Val Ser Asn Gln Thr Thr Lys Pro
    50                  55                  60

Thr Ile Lys Met Leu Arg Thr Thr Val Ser Lys Leu Ala Arg Pro Thr
65                  70                  75                  80

Val Ser Arg Ala Phe Ala Thr Thr Ser Arg Ala Leu Ala Gly Glu Thr
                85                  90                  95

Gly Ala Pro Pro Lys Thr Gly Gly Pro Gly Asp Ala Phe Gln Arg Arg
            100                 105                 110

Glu Lys Ala Asn Glu Asp Phe Ala Ile Arg Gln Arg Glu Lys Glu Lys
        115                 120                 125

Leu Leu Glu Leu Lys Lys Lys Leu Ala Glu Gln Gln Lys His Leu Lys
    130                 135                 140

Thr Leu Ser Asp His Met
145                 150


<210> SEQ ID NO 80
<211> LENGTH: 252
<212> TYPE: DNA
<213> ORGANISM: Neurospora crassa
<220> FEATURE:
<221> NAME/KEY: misc_feature
<222> LOCATION: (1)...(252)
<223> OTHER INFORMATION: NcAFP2 mature cds
<220> FEATURE:
<221> NAME/KEY: CDS
<222> LOCATION: (1)...(252)
<223> OTHER INFORMATION: NcAFP2 mature pp

<400> SEQUENCE: 80

atg ctc cgc acc acc gtc tcc aag ctc gct cgc cct acc gtt tcc agg       48
Met Leu Arg Thr Thr Val Ser Lys Leu Ala Arg Pro Thr Val Ser Arg
 1               5                   10                  15

gcg ttt gcg acc acc tcc cgc gct ctc gcc ggt gag act ggt gct ccc       96
Ala Phe Ala Thr Thr Ser Arg Ala Leu Ala Gly Glu Thr Gly Ala Pro
             20                  25                  30

cca aag acc ggc ggc cca ggt gac gct ttc cag cgc cgc gag aag gcc      144
Pro Lys Thr Gly Gly Pro Gly Asp Ala Phe Gln Arg Arg Glu Lys Ala
         35                  40                  45

aac gag gat ttc gct atc cgc cag cgc gag aag gag aag ctc ctc gag      192
Asn Glu Asp Phe Ala Ile Arg Gln Arg Glu Lys Glu Lys Leu Leu Glu
     50                  55                  60

ctc aag aag aag ctc gcc gag cag cag aag cac ctc aag act ctt tct      240
Leu Lys Lys Lys Leu Ala Glu Gln Gln Lys His Leu Lys Thr Leu Ser
 65                  70                  75                  80

gat cac atg taa                                                      252
Asp His Met


<210> SEQ ID NO 81
<211> LENGTH: 83
<212> TYPE: PRT
<213> ORGANISM: Neurospora crassa

<400> SEQUENCE: 81

Met Leu Arg Thr Thr Val Ser Lys Leu Ala Arg Pro Thr Val Ser Arg
 1               5                   10                  15
```

```
Ala Phe Ala Thr Thr Ser Arg Ala Leu Ala Gly Glu Thr Gly Ala Pro
            20                  25                  30

Pro Lys Thr Gly Gly Pro Gly Asp Ala Phe Gln Arg Arg Glu Lys Ala
        35                  40                  45

Asn Glu Asp Phe Ala Ile Arg Gln Arg Glu Lys Glu Lys Leu Leu Glu
    50                  55                  60

Leu Lys Lys Lys Leu Ala Glu Gln Gln Lys His Leu Lys Thr Leu Ser
65                  70                  75                  80

Asp His Met


<210> SEQ ID NO 82
<211> LENGTH: 204
<212> TYPE: DNA
<213> ORGANISM: Ophiostoma novo-ulmi
<220> FEATURE:
<221> NAME/KEY: misc_feature
<222> LOCATION: (1)...(204)
<223> OTHER INFORMATION: OnAFP1 (Ophiostoma novo-ulmi) mature cds
<220> FEATURE:
<221> NAME/KEY: CDS
<222> LOCATION: (1)...(204)
<223> OTHER INFORMATION: OnAFP1 (Ophiostoma novo-ulmi) mature pp

<400> SEQUENCE: 82

atg tcc gag ggt gcc acc ggt gct ccc ccc aag tcc ggc aac cct gac       48
Met Ser Glu Gly Ala Thr Gly Ala Pro Pro Lys Ser Gly Asn Pro Asp
 1               5                  10                  15

gcc ttc cag cgc cgc gag cgc gcc aac gag gac tac acc att cgc cag       96
Ala Phe Gln Arg Arg Glu Arg Ala Asn Glu Asp Tyr Thr Ile Arg Gln
             20                  25                  30

cgt gag aag gag aag ctg cag cag ctc aag ctc aag ctc aag gag cag      144
Arg Glu Lys Glu Lys Leu Gln Gln Leu Lys Leu Lys Leu Lys Glu Gln
         35                  40                  45

cag gct cac ctt gac cag ctt gcc cag cac atg ttc gta gcc aat gat      192
Gln Ala His Leu Asp Gln Leu Ala Gln His Met Phe Val Ala Asn Asp
     50                  55                  60

cag aag aat tag                                                      204
Gln Lys Asn
 65


<210> SEQ ID NO 83
                 <211> LENGTH: 67
<212> TYPE: PRT
<213> ORGANISM: Ophiostoma novo-ulmi

<400> SEQUENCE: 83

Met Ser Glu Gly Ala Thr Gly Ala Pro Pro Lys Ser Gly Asn Pro Asp
 1               5                  10                  15

Ala Phe Gln Arg Arg Glu Arg Ala Asn Glu Asp Tyr Thr Ile Arg Gln
            20                  25                  30

Arg Glu Lys Glu Lys Leu Gln Gln Leu Lys Leu Lys Leu Lys Glu Gln
        35                  40                  45

Gln Ala His Leu Asp Gln Leu Ala Gln His Met Phe Val Ala Asn Asp
    50                  55                  60

Gln Lys Asn
65


<210> SEQ ID NO 84
<211> LENGTH: 315
<212> TYPE: DNA
<213> ORGANISM: Phaeosphaeria nodorum
<220> FEATURE:
```

```
<221> NAME/KEY: misc_feature
<222> LOCATION: (1)...(315)
<223> OTHER INFORMATION: PnAFP1 (Phaeosphaeria nodorum) full-length cds
<220> FEATURE:
<221> NAME/KEY: CDS
<222> LOCATION: (1)...(315)
<223> OTHER INFORMATION: PnAFP1 (Phaeosphaeria nodorum) full-length pp

<400> SEQUENCE: 84

atg ctc cgc aca tca atc atc aag agc gtc cgc ttt gtc gct gca ccc       48
Met Leu Arg Thr Ser Ile Ile Lys Ser Val Arg Phe Val Ala Ala Pro
 1               5                  10                  15

cgc tac ttc tct gta gct gca cgc cgc atg gct gaa ggt gca acc ggc       96
Arg Tyr Phe Ser Val Ala Ala Arg Arg Met Ala Glu Gly Ala Thr Gly
            20                  25                  30

tct ggc gcg tcg agg cct act ggt tcc gct gga ggt gat gcc ttc acc      144
Ser Gly Ala Ser Arg Pro Thr Gly Ser Ala Gly Gly Asp Ala Phe Thr
        35                  40                  45

aag cgc gag gcc gct tct gag gag ctt tac att cgc cag gaa gaa aag      192
Lys Arg Glu Ala Ala Ser Glu Glu Leu Tyr Ile Arg Gln Glu Glu Lys
     50                  55                  60

gcc aag ctc cta gct atc aag gag aag ctc cgc cag cag agg cag cac      240
Ala Lys Leu Leu Ala Ile Lys Glu Lys Leu Arg Gln Gln Arg Gln His
 65                  70                  75                  80

att gag gac ctt gac aag cac atc gac gat gtg atc aag gaa ggc gaa      288
Ile Glu Asp Leu Asp Lys His Ile Asp Asp Val Ile Lys Glu Gly Glu
                85                  90                  95

gcg tcc ggc cag ggc gaa cag aag taa                                  315
Ala Ser Gly Gln Gly Glu Gln Lys
            100


<210> SEQ ID NO 85
<211> LENGTH: 104
<212> TYPE: PRT
<213> ORGANISM: Phaeosphaeria nodorum

<400> SEQUENCE: 85

Met Leu Arg Thr Ser Ile Ile Lys Ser Val Arg Phe Val Ala Ala Pro
 1               5                  10                  15

Arg Tyr Phe Ser Val Ala Ala Arg Arg Met Ala Glu Gly Ala Thr Gly
            20                  25                  30

Ser Gly Ala Ser Arg Pro Thr Gly Ser Ala Gly Gly Asp Ala Phe Thr
        35                  40                  45

Lys Arg Glu Ala Ala Ser Glu Glu Leu Tyr Ile Arg Gln Glu Glu Lys
    50                  55                  60

Ala Lys Leu Leu Ala Ile Lys Glu Lys Leu Arg Gln Gln Arg Gln His
65                  70                  75                  80

Ile Glu Asp Leu Asp Lys His Ile Asp Asp Val Ile Lys Glu Gly Glu
                85                  90                  95

Ala Ser Gly Gln Gly Glu Gln Lys
            100


<210> SEQ ID NO 86
<211> LENGTH: 237
<212> TYPE: DNA
<213> ORGANISM: Phaeosphaeria nodorum
<220> FEATURE:
<221> NAME/KEY: misc_feature
<222> LOCATION: (1)...(237)
<223> OTHER INFORMATION: PnAFP1 mature cds
<220> FEATURE:
<221> NAME/KEY: CDS
<222> LOCATION: (1)...(237)
```

```
<223> OTHER INFORMATION: PnAFP1 mature pp

<400> SEQUENCE: 86

gct gaa ggt gca acc ggc tct ggc gcg tcg agg cct act ggt tcc gct       48
Ala Glu Gly Ala Thr Gly Ser Gly Ala Ser Arg Pro Thr Gly Ser Ala
 1               5                  10                  15

gga ggt gat gcc ttc acc aag cgc gag gcc gct tct gag gag ctt tac       96
Gly Gly Asp Ala Phe Thr Lys Arg Glu Ala Ala Ser Glu Glu Leu Tyr
             20                  25                  30

att cgc cag gaa gaa aag gcc aag ctc cta gct atc aag gag aag ctc      144
Ile Arg Gln Glu Glu Lys Ala Lys Leu Leu Ala Ile Lys Glu Lys Leu
         35                  40                  45

cgc cag cag agg cag cac att gag gac ctt gac aag cac atc gac gat      192
Arg Gln Gln Arg Gln His Ile Glu Asp Leu Asp Lys His Ile Asp Asp
     50                  55                  60

gtg atc aag gaa ggc gaa gcg tcc ggc cag ggc gaa cag aag taa          237
Val Ile Lys Glu Gly Glu Ala Ser Gly Gln Gly Glu Gln Lys
 65                  70                  75


<210> SEQ ID NO 87
<211> LENGTH: 78
<212> TYPE: PRT
<213> ORGANISM: Phaeosphaeria nodorum

<400> SEQUENCE: 87

Ala Glu Gly Ala Thr Gly Ser Gly Ala Ser Arg Pro Thr Gly Ser Ala
 1               5                  10                  15

Gly Gly Asp Ala Phe Thr Lys Arg Glu Ala Ala Ser Glu Glu Leu Tyr
            20                  25                  30

Ile Arg Gln Glu Glu Lys Ala Lys Leu Leu Ala Ile Lys Glu Lys Leu
        35                  40                  45

Arg Gln Gln Arg Gln His Ile Glu Asp Leu Asp Lys His Ile Asp Asp
    50                  55                  60

Val Ile Lys Glu Gly Glu Ala Ser Gly Gln Gly Glu Gln Lys
65                  70                  75


<210> SEQ ID NO 88
<211> LENGTH: 63
<212> TYPE: PRT
<213> ORGANISM: Pichia jadinii

<400> SEQUENCE: 88

Thr Ala Gly Ala Thr Gly Ala Thr Arg Gln Asp Gly Ser Thr Asp Ala
 1               5                  10                  15

Phe Glu Lys Arg Glu Lys Ala Gln Glu Asp Leu Tyr Ile Arg Gln His
            20                  25                  30

Glu Lys Glu Gln Leu Glu Ala Leu Lys Glu Ser Leu Lys Lys Gln Lys
        35                  40                  45

Lys Ser Leu Asp Asp Leu Glu Asx Lys Ile Asp Asp Leu Thr Lys
    50                  55                  60


<210> SEQ ID NO 89
<211> LENGTH: 258
<212> TYPE: DNA
<213> ORGANISM: Saccharomyces cerevisiae
<220> FEATURE:
<221> NAME/KEY: misc_feature
<222> LOCATION: (1)...(258)
<223> OTHER INFORMATION: ScAFP1 (Saccharomyces cerevisiae) cds

<400> SEQUENCE: 89
```

-continued

```
atgttaccac gttcagcatt agcacgctca ttgcaattac agcgcggtgt ggccgcaagg      60

ttctactctg aaggttctac cggcacccca agagggtcag gctcagagga ttcgtttgtt     120

aaaagggaaa gggccacgga agacttcttc gttaggcagc gtgagaagga gcaactacgc     180

catttgaaag aacaactgga aaaacaacga aagaagatcg attctttgga aaataaaatt     240

gactcgatga ccaaataa                                                   258


<210> SEQ ID NO 90
<211> LENGTH: 85
<212> TYPE: PRT
<213> ORGANISM: Saccharomyces cerevisiae

<400> SEQUENCE: 90

Met Leu Pro Arg Ser Ala Leu Ala Arg Ser Leu Gln Leu Gln Arg Gly
 1               5                  10                  15

Val Ala Ala Arg Phe Tyr Ser Glu Gly Ser Thr Gly Thr Pro Arg Gly
            20                  25                  30

Ser Gly Ser Glu Asp Ser Phe Val Lys Arg Glu Arg Ala Thr Glu Asp
        35                  40                  45

Phe Phe Val Arg Gln Arg Glu Lys Glu Gln Leu Arg His Leu Lys Glu
    50                  55                  60

Gln Leu Glu Lys Gln Arg Lys Lys Ile Asp Ser Leu Glu Asn Lys Ile
65                  70                  75                  80

Asp Ser Met Thr Lys
                85


<210> SEQ ID NO 91
<211> LENGTH: 306
<212> TYPE: DNA
<213> ORGANISM: Thermoascus aurantiacus
<220> FEATURE:
<221> NAME/KEY: misc_feature
<222> LOCATION: (1)...(306)
<223> OTHER INFORMATION: ThaAFP1 full-length cds
<220> FEATURE:
<221> NAME/KEY: CDS
<222> LOCATION: (1)...(306)
<223> OTHER INFORMATION: ThaAFP1 full-length pp

<400> SEQUENCE: 91

atg ttc cgc cag acc ctc gct cgc ccc ctt ctc cgc gcc agc agc ccc       48
Met Phe Arg Gln Thr Leu Ala Arg Pro Leu Leu Arg Ala Ser Ser Pro
 1               5                  10                  15

gtt gtc aac cgg tcc ttc tcg gtc gcg gcg gtc agg atg ggt gca ggc       96
Val Val Asn Arg Ser Phe Ser Val Ala Ala Val Arg Met Gly Ala Gly
            20                  25                  30

gac ctt ggc gcc ccc aag acg cac ggt tac cag caa gat gac cag ttc      144
Asp Leu Gly Ala Pro Lys Thr His Gly Tyr Gln Gln Asp Asp Gln Phe
        35                  40                  45

cac cgg cgt gag gcc gcc cag gag agc ctg tac atc agg gag aag gag      192
His Arg Arg Glu Ala Ala Gln Glu Ser Leu Tyr Ile Arg Glu Lys Glu
    50                  55                  60

ctc gag aag ctc agg gcc ctg aag gcc aag atc cag gag cag cgc aag      240
Leu Glu Lys Leu Arg Ala Leu Lys Ala Lys Ile Gln Glu Gln Arg Lys
65                  70                  75                  80

cac ctg gaa gag ctc gac aag cac att gac gag ctc acc cga gag caa      288
His Leu Glu Glu Leu Asp Lys His Ile Asp Glu Leu Thr Arg Glu Gln
                85                  90                  95

ggc gga gag aag aac taa                                              306
Gly Gly Glu Lys Asn
            100
```

<210> SEQ ID NO 92
<211> LENGTH: 101
<212> TYPE: PRT
<213> ORGANISM: Thermoascus aurantiacus

<400> SEQUENCE: 92

```
Met Phe Arg Gln Thr Leu Ala Arg Pro Leu Leu Arg Ala Ser Ser Pro
 1               5                  10                  15

Val Val Asn Arg Ser Phe Ser Val Ala Ala Val Arg Met Gly Ala Gly
            20                  25                  30

Asp Leu Gly Ala Pro Lys Thr His Gly Tyr Gln Gln Asp Asp Gln Phe
        35                  40                  45

His Arg Arg Glu Ala Ala Gln Glu Ser Leu Tyr Ile Arg Glu Lys Glu
    50                  55                  60

Leu Glu Lys Leu Arg Ala Leu Lys Ala Lys Ile Gln Glu Gln Arg Lys
65                  70                  75                  80

His Leu Glu Glu Leu Asp Lys His Ile Asp Glu Leu Thr Arg Glu Gln
                85                  90                  95

Gly Gly Glu Lys Asn
            100
```

<210> SEQ ID NO 93
<211> LENGTH: 219
<212> TYPE: DNA
<213> ORGANISM: Thermoascus aurantiacus
<220> FEATURE:
<221> NAME/KEY: misc_feature
<222> LOCATION: (1)...(219)
<223> OTHER INFORMATION: ThaAFP1 mature cds
<220> FEATURE:
<221> NAME/KEY: CDS
<222> LOCATION: (1)...(219)
<223> OTHER INFORMATION: ThaAFP1 mature pp

<400> SEQUENCE: 93

```
ggt gca ggc gac ctt ggc gcc ccc aag acg cac ggt tac cag caa gat       48
Gly Ala Gly Asp Leu Gly Ala Pro Lys Thr His Gly Tyr Gln Gln Asp
 1               5                  10                  15

gac cag ttc cac cgg cgt gag gcc gcc cag gag agc ctg tac atc agg       96
Asp Gln Phe His Arg Arg Glu Ala Ala Gln Glu Ser Leu Tyr Ile Arg
            20                  25                  30

gag aag gag ctc gag aag ctc agg gcc ctg aag gcc aag atc cag gag      144
Glu Lys Glu Leu Glu Lys Leu Arg Ala Leu Lys Ala Lys Ile Gln Glu
        35                  40                  45

cag cgc aag cac ctg gaa gag ctc gac aag cac att gac gag ctc acc      192
Gln Arg Lys His Leu Glu Glu Leu Asp Lys His Ile Asp Glu Leu Thr
    50                  55                  60

cga gag caa ggc gga gag aag aac taa                                  219
Arg Glu Gln Gly Gly Glu Lys Asn
65                  70
```

<210> SEQ ID NO 94
<211> LENGTH: 72
<212> TYPE: PRT
<213> ORGANISM: Thermoascus aurantiacus

<400> SEQUENCE: 94

```
Gly Ala Gly Asp Leu Gly Ala Pro Lys Thr His Gly Tyr Gln Gln Asp
 1               5                  10                  15

Asp Gln Phe His Arg Arg Glu Ala Ala Gln Glu Ser Leu Tyr Ile Arg
            20                  25                  30
```

```
Glu Lys Glu Leu Glu Lys Leu Arg Ala Leu Lys Ala Lys Ile Gln Glu
        35                  40                  45

Gln Arg Lys His Leu Glu Glu Leu Asp Lys His Ile Asp Glu Leu Thr
    50                  55                  60

Arg Glu Gln Gly Gly Glu Lys Asn
65                  70


<210> SEQ ID NO 95
<211> LENGTH: 219
<212> TYPE: DNA
<213> ORGANISM: Trichoderma reseii
<220> FEATURE:
<221> NAME/KEY: misc_feature
<222> LOCATION: (1)...(219)
<223> OTHER INFORMATION: TrAFP1 mature cds
<220> FEATURE:
<221> NAME/KEY: CDS
<222> LOCATION: (1)...(219)
<223> OTHER INFORMATION: TrAFP1 mature pp

<400> SEQUENCE: 95

atg ggc gaa ggc gac act ggc gct ccc ccc aag acc ggc ggc caa ggc       48
Met Gly Glu Gly Asp Thr Gly Ala Pro Pro Lys Thr Gly Gly Gln Gly
 1               5                  10                  15

gac gcc ttc cag cgc cgc gaa aag gcc gcc gag gac tac gcc atc cgc       96
Asp Ala Phe Gln Arg Arg Glu Lys Ala Ala Glu Asp Tyr Ala Ile Arg
            20                  25                  30

cag cgc gaa aag gaa aag ctg ctc gag ctc agg aag aag ctg acc cga      144
Gln Arg Glu Lys Glu Lys Leu Leu Glu Leu Arg Lys Lys Leu Thr Arg
         35                  40                  45

gca gca gga gca cct cga tcg cct cgc caa gcc att gac gag att acc      192
Ala Ala Gly Ala Pro Arg Ser Pro Arg Gln Ala Ile Asp Glu Ile Thr
     50                  55                  60

aag gag cag ggc ggc gaa caa aac taa                                  219
Lys Glu Gln Gly Gly Glu Gln Asn
 65                  70


<210> SEQ ID NO 96
<211> LENGTH: 72
<212> TYPE: PRT
<213> ORGANISM: Trichoderma reseii

<400> SEQUENCE: 96

Met Gly Glu Gly Asp Thr Gly Ala Pro Pro Lys Thr Gly Gly Gln Gly
 1               5                  10                  15

Asp Ala Phe Gln Arg Arg Glu Lys Ala Ala Glu Asp Tyr Ala Ile Arg
            20                  25                  30

Gln Arg Glu Lys Glu Lys Leu Leu Glu Leu Arg Lys Lys Leu Thr Arg
        35                  40                  45

Ala Ala Gly Ala Pro Arg Ser Pro Arg Gln Ala Ile Asp Glu Ile Thr
    50                  55                  60

Lys Glu Gln Gly Gly Glu Gln Asn
65                  70


<210> SEQ ID NO 97
<211> LENGTH: 339
<212> TYPE: DNA
<213> ORGANISM: Triticum aestivum
<220> FEATURE:
<221> NAME/KEY: misc_feature
<222> LOCATION: (1)...(339)
<223> OTHER INFORMATION: TaAFP1 (Triticum aestivum) full-length cds
<220> FEATURE:
```

<221> NAME/KEY: misc_feature
<222> LOCATION: 24, 55, 273, 319, 332
<223> OTHER INFORMATION: n = A,T,C or G
<220> FEATURE:
<221> NAME/KEY: misc_feature
<222> LOCATION: 24, 55, 273, 319, 332
<223> OTHER INFORMATION: n = A,T,C or G

<400> SEQUENCE: 97
atgggtctca taaaattcat caanatgaat catccaatat ccagcaaact gatanccccta 60 ggaatgaggc agcttgcccc tttgtctact tctacacgag ctatggcagc tggtgatact 120
ggatctccta aagtcggagg ctcggcatct gcggacgcat ttacccagcg agaaaagtca 180
aacgaagact ttcacattag gtcaagggaa agagagaagt tgcttgaact ccaaaaaacg 240
tatctcaaga cacacgatca ctacgtcgac ttngaagaac acctcgacga acttttcaat 300
atggatcccg gtcaaggang aggggggaaa antagttag 339

<210> SEQ ID NO 98
<211> LENGTH: 112
<212> TYPE: PRT
<213> ORGANISM: Triticum aestivum
<220> FEATURE:
<221> NAME/KEY: VARIANT
<222> LOCATION: 8, 19, 91, 107, 111
<223> OTHER INFORMATION: Xaa = Any Amino Acid

<400> SEQUENCE: 98

Met Gly Leu Ile Lys Phe Ile Xaa Met Asn His Pro Ile Ser Ser Lys
1 5 10 15

Leu Ile Xaa Leu Gly Met Arg Gln Leu Ala Pro Leu Ser Thr Ser Thr
20 25 30

Arg Ala Met Ala Ala Gly Asp Thr Gly Ser Pro Lys Val Gly Gly Ser
35 40 45

Ala Ser Ala Asp Ala Phe Thr Gln Arg Glu Lys Ser Asn Glu Asp Phe
50 55 60

His Ile Arg Ser Arg Glu Arg Glu Lys Leu Leu Glu Leu Gln Lys Thr
65 70 75 80

Tyr Leu Lys Thr His Asp His Tyr Val Asp Xaa Glu Glu His Leu Asp
85 90 95

Glu Leu Phe Asn Met Asp Pro Gly Gln Gly Xaa Gly Gly Lys Xaa Ser
100 105 110

<210> SEQ ID NO 99
<211> LENGTH: 237
<212> TYPE: DNA
<213> ORGANISM: Triticum aestivum
<220> FEATURE:
<221> NAME/KEY: misc_feature
<222> LOCATION: (1)...(237)
<223> OTHER INFORMATION: TaAFP1 (Triticum aestivum) full-length cds
<220> FEATURE:
<221> NAME/KEY: misc_feature
<222> LOCATION: 171, 217, 230
<223> OTHER INFORMATION: n = A,T,C or G
<220> FEATURE:
<221> NAME/KEY: misc_feature
<222> LOCATION: 171, 217, 230
<223> OTHER INFORMATION: n = A,T,C or G

<400> SEQUENCE: 99
atggcagctg gtgatactgg atctcctaaa gtcggaggct cggcatctgc ggacgcattt 60
acccagcgag aaaagtcaaa cgaagacttt cacattaggt caagggaaag agagaagttg 120

-continued

```
cttgaactcc aaaaaacgta tctcaagaca cacgatcact acgtcgactt ngaagaacac    180

ctcgacgaac ttttcaatat ggatcccggt caaggangag gggggaaaan tagttag       237


<210> SEQ ID NO 100
<211> LENGTH: 78
<212> TYPE: PRT
<213> ORGANISM: Triticum aestivum
<220> FEATURE:
<221> NAME/KEY: VARIANT
<222> LOCATION: 57, 73, 77
<223> OTHER INFORMATION: Xaa = Any Amino Acid

<400> SEQUENCE: 100

Met Ala Ala Gly Asp Thr Gly Ser Pro Lys Val Gly Gly Ser Ala Ser
 1               5                  10                  15

Ala Asp Ala Phe Thr Gln Arg Glu Lys Ser Asn Glu Asp Phe His Ile
            20                  25                  30

Arg Ser Arg Glu Arg Glu Lys Leu Leu Glu Leu Gln Lys Thr Tyr Leu
        35                  40                  45

Lys Thr His Asp His Tyr Val Asp Xaa Glu Glu His Leu Asp Glu Leu
    50                  55                  60

Phe Asn Met Asp Pro Gly Gln Gly Xaa Gly Gly Lys Xaa Ser
65                  70                  75


<210> SEQ ID NO 101
<211> LENGTH: 291
<212> TYPE: DNA
<213> ORGANISM: Triticum aestivum
<220> FEATURE:
<221> NAME/KEY: misc_feature
<222> LOCATION: (1)...(291)
<223> OTHER INFORMATION: TaAFP2 full-length cds
<220> FEATURE:
<221> NAME/KEY: CDS
<222> LOCATION: (1)...(291)
<223> OTHER INFORMATION: TaAFP2 full-length pp

<400> SEQUENCE: 101

atg ctt cgc aca tct ttc cgc cag gca gcc gcc ttc cga ccc att cga       48
Met Leu Arg Thr Ser Phe Arg Gln Ala Ala Ala Phe Arg Pro Ile Arg
 1               5                  10                  15

tgc ttc tct act act ccc cgc gtc atg act gag ggt gct act gga gct       96
Cys Phe Ser Thr Thr Pro Arg Val Met Thr Glu Gly Ala Thr Gly Ala
            20                  25                  30

ccc cgc cct act gga ggc tct ggt gat gct ttc cag cga cgt gag aag      144
Pro Arg Pro Thr Gly Gly Ser Gly Asp Ala Phe Gln Arg Arg Glu Lys
        35                  40                  45

gcc agc gag gat tac gct atc cgc cag cgt gag aag gag aag ctc att      192
Ala Ser Glu Asp Tyr Ala Ile Arg Gln Arg Glu Lys Glu Lys Leu Ile
    50                  55                  60

gag ctc aag aag aag ctc cag gag cag cag cag cac ctt gac cgt ctc      240
Glu Leu Lys Lys Lys Leu Gln Glu Gln Gln Gln His Leu Asp Arg Leu
65                  70                  75                  80

tcc aag cac att gat gag atc aca aag gag cag ggc ggc gag cag cac      288
Ser Lys His Ile Asp Glu Ile Thr Lys Glu Gln Gly Gly Glu Gln His
                85                  90                  95

taa                                                                  291


<210> SEQ ID NO 102
<211> LENGTH: 96
<212> TYPE: PRT
<213> ORGANISM: Triticum aestivum
```

<400> SEQUENCE: 102

```
Met Leu Arg Thr Ser Phe Arg Gln Ala Ala Ala Phe Arg Pro Ile Arg
 1               5                  10                  15

Cys Phe Ser Thr Thr Pro Arg Val Met Thr Glu Gly Ala Thr Gly Ala
            20                  25                  30

Pro Arg Pro Thr Gly Gly Ser Gly Asp Ala Phe Gln Arg Arg Glu Lys
        35                  40                  45

Ala Ser Glu Asp Tyr Ala Ile Arg Gln Arg Glu Lys Glu Lys Leu Ile
    50                  55                  60

Glu Leu Lys Lys Lys Leu Gln Glu Gln Gln Gln His Leu Asp Arg Leu
65                  70                  75                  80

Ser Lys His Ile Asp Glu Ile Thr Lys Glu Gln Gly Gly Glu Gln His
                85                  90                  95
```

<210> SEQ ID NO 103
<211> LENGTH: 216
<212> TYPE: DNA
<213> ORGANISM: Triticum aestivum
<220> FEATURE:
<221> NAME/KEY: misc_feature
<222> LOCATION: (1)...(216)
<223> OTHER INFORMATION: TaAFP2 mature cds
<220> FEATURE:
<221> NAME/KEY: CDS
<222> LOCATION: (1)...(216)
<223> OTHER INFORMATION: TaAFP2 mature pp

<400> SEQUENCE: 103

```
act gag ggt gct act gga gct ccc cgc cct act gga ggc tct ggt gat       48
Thr Glu Gly Ala Thr Gly Ala Pro Arg Pro Thr Gly Gly Ser Gly Asp
 1               5                   10                  15

gct ttc cag cga cgt gag aag gcc agc gag gat tac gct atc cgc cag       96
Ala Phe Gln Arg Arg Glu Lys Ala Ser Glu Asp Tyr Ala Ile Arg Gln
             20                  25                  30

cgt gag aag gag aag ctc att gag ctc aag aag aag ctc cag gag cag      144
Arg Glu Lys Glu Lys Leu Ile Glu Leu Lys Lys Lys Leu Gln Glu Gln
         35                  40                  45

cag cag cac ctt gac cgt ctc tcc aag cac att gat gag atc aca aag      192
Gln Gln His Leu Asp Arg Leu Ser Lys His Ile Asp Glu Ile Thr Lys
     50                  55                  60

gag cag ggc ggc gag cag cac taa                                      216
Glu Gln Gly Gly Glu Gln His
 65                  70
```

<210> SEQ ID NO 104
<211> LENGTH: 71
<212> TYPE: PRT
<213> ORGANISM: Triticum aestivum

<400> SEQUENCE: 104

```
Thr Glu Gly Ala Thr Gly Ala Pro Arg Pro Thr Gly Gly Ser Gly Asp
 1               5                  10                  15

Ala Phe Gln Arg Arg Glu Lys Ala Ser Glu Asp Tyr Ala Ile Arg Gln
            20                  25                  30

Arg Glu Lys Glu Lys Leu Ile Glu Leu Lys Lys Lys Leu Gln Glu Gln
        35                  40                  45

Gln Gln His Leu Asp Arg Leu Ser Lys His Ile Asp Glu Ile Thr Lys
    50                  55                  60

Glu Gln Gly Gly Glu Gln His
65                  70
```

```
<210> SEQ ID NO 105
<211> LENGTH: 264
<212> TYPE: DNA
<213> ORGANISM: Vitis vinifera
<220> FEATURE:
<221> NAME/KEY: misc_feature
<222> LOCATION: (1)...(264)
<223> OTHER INFORMATION: VvAFP1 full-length cds
<220> FEATURE:
<221> NAME/KEY: CDS
<222> LOCATION: (1)...(264)
<223> OTHER INFORMATION: VvAFP1 full-length pp

<400> SEQUENCE: 105

atg ctc cgc act acc atc agc cag gct gcc atc cgc cgt ccc gtc gcc       48
Met Leu Arg Thr Thr Ile Ser Gln Ala Ala Ile Arg Arg Pro Val Ala
 1               5                   10                  15

ctc gcg tcc cga gct gct ttc acc acc act gcc cgc gcc atg ggt gcc       96
Leu Ala Ser Arg Ala Ala Phe Thr Thr Thr Ala Arg Ala Met Gly Ala
             20                  25                  30

ggc gac acc gga tct ccc ccc aag act ggc ggt gcc ggc gat gcc ttc      144
Gly Asp Thr Gly Ser Pro Pro Lys Thr Gly Gly Ala Gly Asp Ala Phe
         35                  40                  45

cag aag cgc gag aag gct gcc gag gat tac gcc atc cgc cag cgc gag      192
Gln Lys Arg Glu Lys Ala Ala Glu Asp Tyr Ala Ile Arg Gln Arg Glu
     50                  55                  60

aag gag aag ctt ctg gag atg aag aag aag att caa gga gca agc agg      240
Lys Glu Lys Leu Leu Glu Met Lys Lys Lys Ile Gln Gly Ala Ser Arg
 65                  70                  75                  80

ctc acc tgc aag caa gct ctc tga                                      264
Leu Thr Cys Lys Gln Ala Leu
                 85


<210> SEQ ID NO 106
<211> LENGTH: 87
<212> TYPE: PRT
<213> ORGANISM: Vitis vinifera

<400> SEQUENCE: 106

Met Leu Arg Thr Thr Ile Ser Gln Ala Ala Ile Arg Arg Pro Val Ala
 1               5                   10                  15

Leu Ala Ser Arg Ala Ala Phe Thr Thr Thr Ala Arg Ala Met Gly Ala
            20                  25                  30

Gly Asp Thr Gly Ser Pro Pro Lys Thr Gly Gly Ala Gly Asp Ala Phe
        35                  40                  45

Gln Lys Arg Glu Lys Ala Ala Glu Asp Tyr Ala Ile Arg Gln Arg Glu
    50                  55                  60

Lys Glu Lys Leu Leu Glu Met Lys Lys Lys Ile Gln Gly Ala Ser Arg
65                  70                  75                  80

Leu Thr Cys Lys Gln Ala Leu
                85


<210> SEQ ID NO 107
<211> LENGTH: 174
<212> TYPE: DNA
<213> ORGANISM: Vitis vinifera
<220> FEATURE:
<221> NAME/KEY: misc_feature
<222> LOCATION: (1)...(174)
<223> OTHER INFORMATION: VvAFP1 mature cds
<220> FEATURE:
<221> NAME/KEY: CDS
<222> LOCATION: (1)...(174)
<223> OTHER INFORMATION: VvAFP1 mature pp
```

<400> SEQUENCE: 107

```
ggt gcc ggc gac acc gga tct ccc ccc aag act ggc ggt gcc ggc gat       48
Gly Ala Gly Asp Thr Gly Ser Pro Pro Lys Thr Gly Gly Ala Gly Asp
 1               5                  10                  15

gcc ttc cag aag cgc gag aag gct gcc gag gat tac gcc atc cgc cag       96
Ala Phe Gln Lys Arg Glu Lys Ala Ala Glu Asp Tyr Ala Ile Arg Gln
             20                  25                  30

cgc gag aag gag aag ctt ctg gag atg aag aag aag att caa gga gca      144
Arg Glu Lys Glu Lys Leu Leu Glu Met Lys Lys Lys Ile Gln Gly Ala
         35                  40                  45

agc agg ctc acc tgc aag caa gct ctc tga                              174
Ser Arg Leu Thr Cys Lys Gln Ala Leu
     50                  55
```

<210> SEQ ID NO 108
<211> LENGTH: 57
<212> TYPE: PRT
<213> ORGANISM: Vitis vinifera

<400> SEQUENCE: 108

```
Gly Ala Gly Asp Thr Gly Ser Pro Pro Lys Thr Gly Gly Ala Gly Asp
 1               5                  10                  15

Ala Phe Gln Lys Arg Glu Lys Ala Ala Glu Asp Tyr Ala Ile Arg Gln
            20                  25                  30

Arg Glu Lys Glu Lys Leu Leu Glu Met Lys Lys Lys Ile Gln Gly Ala
        35                  40                  45

Ser Arg Leu Thr Cys Lys Gln Ala Leu
    50                  55
```

<210> SEQ ID NO 109
<211> LENGTH: 252
<212> TYPE: DNA
<213> ORGANISM: Yarrowia lipolytica
<220> FEATURE:
<221> NAME/KEY: misc_feature
<222> LOCATION: (1)...(252)
<223> OTHER INFORMATION: YlAFP1 (Yarrowia lipolytica) full-length cds

<400> SEQUENCE: 109

```
atgcttaccc gaattaccac cgccaccgtc actcgagttc ctcgagtcgc cgcccgattc     60

tactctgagg gctccaccgg ttcctaccga ggcgagggat ctggcgattc tttcaccaaa    120

cgagagaagg cccaggagga cctctacgtc aagcagcagg agaaggagaa gctcgatgct    180

ctccgaaagc agcttaacaa gctcaagcag gacactgccg accttgagaa gcaccttgac    240

tccaagaaat ag                                                        252
```

<210> SEQ ID NO 110
<211> LENGTH: 83
<212> TYPE: PRT
<213> ORGANISM: Yarrowia lipolytica

<400> SEQUENCE: 110

```
Met Leu Thr Arg Ile Thr Thr Ala Thr Val Thr Arg Val Pro Arg Val
 1               5                  10                  15

Ala Ala Arg Phe Tyr Ser Glu Gly Ser Thr Gly Ser Tyr Arg Gly Glu
            20                  25                  30

Gly Ser Gly Asp Ser Phe Thr Lys Arg Glu Lys Ala Gln Glu Asp Leu
        35                  40                  45

Tyr Val Lys Gln Gln Glu Lys Glu Lys Leu Asp Ala Leu Arg Lys Gln
```

```
    50                  55                  60

Leu Asn Lys Leu Lys Gln Asp Thr Ala Asp Leu Glu Lys His Leu Asp
65                  70                  75                  80

Ser Lys Lys


<210> SEQ ID NO 111
<211> LENGTH: 75
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 11, 12, 16, 17, 18, 23, 33, 50, 53, 54, 57, 58, 61, 69
<223> OTHER INFORMATION: Xaa = Any Amino Acid or No Amino Acid

<400> SEQUENCE: 111

Met Gly Glu Gly Asp Thr Gly Ala Pro Arg Xaa Xaa Thr Gly Gly Xaa
 1               5                  10                  15

Xaa Xaa Gly Asp Ala Phe Xaa Lys Arg Glu Lys Ala Asn Glu Asp Tyr
            20                  25                  30

Xaa Ile Arg Gln Arg Glu Lys Glu Lys Leu Leu Glu Leu Lys Lys Lys
        35                  40                  45

Leu Xaa Glu Gln Xaa Xaa His Leu Xaa Xaa Leu Asp Xaa His Ile Asp
    50                  55                  60

Glu Ile Thr Lys Xaa Gln Gly Gly Glu Gln Asn
65                  70                  75


<210> SEQ ID NO 112
<211> LENGTH: 72
<212> TYPE: DNA
<213> ORGANISM: Hordeum vulgare
<220> FEATURE:
<221> NAME/KEY: misc_feature
<222> LOCATION: (1)...(72)
<223> OTHER INFORMATION: Barley alpha amylase signal peptide coding
      sequence

<400> SEQUENCE: 112

atggccaaca agcacctgtc cctctccctc ttcctcgtgc tcctcggcct ctccgcctcc     60

ctcgcctccg ga                                                         72


<210> SEQ ID NO 113
<211> LENGTH: 24
<212> TYPE: PRT
<213> ORGANISM: Hordeum vulgare

<400> SEQUENCE: 113

Met Ala Asn Lys His Leu Ser Leu Ser Leu Phe Leu Val Leu Leu Gly
 1               5                  10                  15

Leu Ser Ala Ser Leu Ala Ser Gly
            20


<210> SEQ ID NO 114
<211> LENGTH: 4
<212> TYPE: PRT
<213> ORGANISM: Artificial Sequence
<220> FEATURE:
<223> OTHER INFORMATION: Consensus sequence

<400> SEQUENCE: 114

Lys Asp Glu Leu
 1
```

-continued

```
<210> SEQ ID NO 115
<211> LENGTH: 6
<212> TYPE: PRT
<213> ORGANISM: Artificial Sequence
<220> FEATURE:
<223> OTHER INFORMATION: Consensus sequence

<400> SEQUENCE: 115

Ser Glu Lys Asp Glu Leu
 1               5


<210> SEQ ID NO 116
<211> LENGTH: 4
<212> TYPE: PRT
<213> ORGANISM: Artificial Sequence
<220> FEATURE:
<223> OTHER INFORMATION: Consensus sequence

<400> SEQUENCE: 116

His Asp Glu Leu
 1


<210> SEQ ID NO 117
<211> LENGTH: 4
<212> TYPE: PRT
<213> ORGANISM: Artificial Sequence
<220> FEATURE:
<223> OTHER INFORMATION: Consensus sequence

<400> SEQUENCE: 117

His Asp Glu Phe
 1
```